(12) United States Patent
Baker et al.

(10) Patent No.: US 10,328,058 B2
(45) Date of Patent: Jun. 25, 2019

(54) TREATING ATHEROSCLEROSIS BY REMOVING SENESCENT FOAM CELL MACROPHAGES FROM ATHEROSCLEROTIC PLAQUES

(71) Applicants: Mayo Foundation for Medical Education and Research, Rochester, MN (US); Unity Biotechnology, Inc., Brisbane, CA (US); Buck Institute for Research on Aging, Novato, CA (US)

(72) Inventors: Darren J. Baker, Rochester, MN (US); Marco Demaria, Groningen (NL); Albert Davalos, San Rafael, CA (US); Bennett G. Childs, Rochester, MN (US); Jan M. A. van Deursen, Rochester, MN (US); James L. Kirkland, Rochester, MN (US); Tamar Tchkonia, Rochester, MN (US); Yi Zhu, Rochester, MN (US); Nathaniel David, Brisbane, CA (US); Remi-Martin Laberge, San Francisco, CA (US); Judith Campisi, Berkeley, CA (US)

(73) Assignees: Mayo Foundation for Medical Education and Research, Rochester, MN (US); Unity Biotechnology, Inc., Brisbane, CA (US); Buck Institute for Research on Aging, Novato, CA (US)

( * ) Notice: Subject to any disclaimer, the term of this patent is extended or adjusted under 35 U.S.C. 154(b) by 0 days.

(21) Appl. No.: 15/792,593

(22) Filed: Oct. 24, 2017

(65) Prior Publication Data
US 2018/0104222 A1 Apr. 19, 2018

Related U.S. Application Data

(63) Continuation-in-part of application No. 15/114,762, filed as application No. PCT/US2015/013387 on Jan. 28, 2015, now Pat. No. 9,993,472.

(60) Provisional application No. 61/932,704, filed on Jan. 28, 2014, provisional application No. 61/932,711, filed on Jan. 28, 2014, provisional application No. 61/979,911, filed on Apr. 15, 2014, provisional application No. 62/002,709, filed on May 23, 2014, provisional application No. 62/042,708, filed on Aug. 27, 2014, provisional application No. 62/044,664, filed on Sep. 2, 2014, provisional application No. 62/057,820, filed on Sep. 30, 2014, provisional
(Continued)

(51) Int. Cl.
| | | |
|---|---|---|
| A61P 9/10 | (2006.01) |
| A61K 31/496 | (2006.01) |
| A61K 31/4178 | (2006.01) |
| A61K 31/404 | (2006.01) |
| A61K 31/428 | (2006.01) |
| A61K 31/4375 | (2006.01) |
| A61K 31/5377 | (2006.01) |
| A61K 9/00 | (2006.01) |
| A61K 31/4164 | (2006.01) |
| A61K 45/06 | (2006.01) |
| A61K 47/36 | (2006.01) |
| C12N 5/00 | (2006.01) |

(52) U.S. Cl.
CPC ........ *A61K 31/4178* (2013.01); *A61K 9/0019* (2013.01); *A61K 31/404* (2013.01); *A61K 31/4164* (2013.01); *A61K 31/428* (2013.01); *A61K 31/4375* (2013.01); *A61K 31/496* (2013.01); *A61K 31/5377* (2013.01); *A61P 9/10* (2018.01); *A61K 45/06* (2013.01); *A61K 47/36* (2013.01); *C12N 5/0081* (2013.01); *C12N 2501/999* (2013.01)

(58) Field of Classification Search
CPC ..... A61P 9/10; A61K 31/4175; A61K 31/496; A61K 31/4178
See application file for complete search history.

(56) References Cited

U.S. PATENT DOCUMENTS

| | | |
|---|---|---|
| 6,617,346 B1 | 9/2003 | Kong et al. |
| 6,734,302 B2 | 5/2004 | Kong et al. |

(Continued)

FOREIGN PATENT DOCUMENTS

| | | | | |
|---|---|---|---|---|
| KR | 10-2012-0118596 A | * | 7/2012 | ........... A61K 31/497 |
| KR | 20130139512 A | | 12/2013 | |

(Continued)

OTHER PUBLICATIONS

Machine translation of Kim (KR '596), retrieved from translate.google.com (Sep. 2018). (Year: 2012).*

(Continued)

*Primary Examiner* — Theodore R. West
(74) *Attorney, Agent, or Firm* — Michael Schiff; Wilson Sonsini Goodrich & Rosati

(57) ABSTRACT

Foamy macrophages with senescence markers accumulate in the subendothelial space at the onset of atherosclerosis where they drive pathology by increasing expression of key atherogenic and inflammatory cytokines and chemokines. In advanced lesions, senescent cells promote features of plaque instability, including elastic fiber degradation and fibrous cap thinning, by heightening metalloprotease production. This invention provides methods and materials for treating arthritis by removing senescent cells in or around atherosclerotic plaques, thereby stabilizing the plaques, inhibiting rupture of the plaques and pathological sequelae that manifest as coronary artery disease.

12 Claims, 37 Drawing Sheets

Related U.S. Application Data application No. 62/057,825, filed on Sep. 30, 2014, provisional application No. 62/057,828, filed on Sep. 30, 2014, provisional application No. 62/061,627, filed on Oct. 8, 2014, provisional application No. 62/061,629, filed on Oct. 8, 2014, provisional application No. 62/412,223, filed on Oct. 24, 2016, provisional application No. 62/412,605, filed on Oct. 25, 2016.

(56) References Cited

U.S. PATENT DOCUMENTS

| | | |
|---|---|---|
| 7,482,134 B2 | 1/2009 | Jang et al. |
| 7,705,007 B2 | 4/2010 | Fotouhi et al. |
| 7,767,684 B2 | 8/2010 | Bruncko et al. |
| 7,842,681 B2 | 11/2010 | Elmore et al. |
| 7,851,626 B2 | 12/2010 | Ding et al. |
| 7,893,278 B2 | 2/2011 | Haley et al. |
| 8,114,893 B2 | 2/2012 | Baell et al. |
| 8,168,645 B2 | 5/2012 | Baell et al. |
| 8,168,784 B2 | 5/2012 | Franczyk, II et al. |
| 8,343,967 B2 | 1/2013 | Ding et al. |
| 8,426,422 B2 | 4/2013 | Hexamer et al. |
| 8,563,735 B2 | 10/2013 | Bruncko et al. |
| 8,586,754 B2 | 11/2013 | Bruncko et al. |
| 8,691,184 B2 | 4/2014 | Wang et al. |
| 9,018,381 B2 | 4/2015 | Diebold et al. |
| 9,248,140 B2 | 2/2016 | Diebold et al. |
| 9,266,860 B2 | 2/2016 | Guy et al. |
| 9,630,990 B2 | 4/2017 | Shetty et al. |
| 2002/0054915 A1 | 5/2002 | Goldenheim et al. |
| 2002/0197602 A1 | 12/2002 | Burmer et al. |
| 2003/0157028 A1 | 8/2003 | Lewis et al. |
| 2005/0019865 A1 | 1/2005 | Kihm et al. |
| 2005/0181076 A1 | 8/2005 | Ziegler |
| 2005/0282803 A1 | 12/2005 | Haley et al. |
| 2006/0122150 A1 | 6/2006 | Argentieri et al. |
| 2006/0182781 A1 | 8/2006 | Hughes et al. |
| 2007/0129416 A1 | 6/2007 | Ding et al. |
| 2007/0292475 A1 | 12/2007 | Campbell et al. |
| 2008/0221132 A1 | 9/2008 | Cai et al. |
| 2008/0234362 A1 | 9/2008 | Chandler |
| 2009/0105319 A1 | 4/2009 | Pellecchia et al. |
| 2010/0016218 A1 | 1/2010 | Lichter et al. |
| 2010/0087436 A1 | 4/2010 | Bardwell et al. |
| 2010/0093648 A1 | 4/2010 | Cruz |
| 2010/0292200 A1 | 11/2010 | Kile et al. |
| 2010/0310504 A1 | 12/2010 | Lowe et al. |
| 2011/0212909 A1 | 9/2011 | Wen et al. |
| 2011/0218206 A1 | 9/2011 | Chan |
| 2012/0028925 A1 | 2/2012 | Tao et al. |
| 2012/0035134 A1 | 2/2012 | Diebold et al. |
| 2012/0108590 A1 | 5/2012 | Birtalan et al. |
| 2012/0115880 A1 | 5/2012 | Dyer et al. |
| 2012/0129853 A1 | 5/2012 | Elmore et al. |
| 2012/0156134 A1 | 6/2012 | Squires |
| 2012/0183534 A1 | 7/2012 | Gruber |
| 2012/0276093 A1 | 11/2012 | Ballinari et al. |
| 2012/0277210 A1 | 11/2012 | Catron et al. |
| 2012/0283269 A1 | 11/2012 | Blagosklonny et al. |
| 2013/0096121 A1 | 4/2013 | Wang et al. |
| 2013/0149314 A1 | 6/2013 | Bullerdiek et al. |
| 2013/0225603 A1 | 8/2013 | Chavala et al. |
| 2013/0267534 A1 | 10/2013 | Bruncko et al. |
| 2013/0287763 A1 | 10/2013 | Sathyanarayanan et al. |
| 2013/0302283 A1 | 11/2013 | Kihm |
| 2013/0317043 A1 | 11/2013 | Wagner et al. |
| 2014/0005190 A1 | 1/2014 | Baell et al. |
| 2014/0017341 A1 | 1/2014 | Gourlaouen |
| 2014/0018302 A1 | 1/2014 | Walensky et al. |
| 2014/0073640 A1 | 3/2014 | Judd et al. |
| 2014/0134163 A1 | 5/2014 | Errico et al. |
| 2014/0220111 A1 | 8/2014 | Hayes et al. |
| 2014/0275082 A1 | 9/2014 | Tao et al. |
| 2014/0328893 A1 | 11/2014 | Adnot |
| 2015/0126573 A1 | 5/2015 | Boczkowski et al. |
| 2015/0140036 A1 | 5/2015 | Mannick et al. |
| 2015/0231136 A1 | 8/2015 | Chavala et al. |
| 2016/0022720 A1 | 1/2016 | Jordan |
| 2016/0122758 A1 | 5/2016 | Krizhanovsky et al. |
| 2017/0056421 A1 | 3/2017 | Zhou et al. |
| 2017/0119789 A1 | 5/2017 | Campisi et al. |
| 2017/0196857 A1 | 7/2017 | Laberge et al. |
| 2017/0196858 A1 | 7/2017 | Laberge et al. |
| 2017/0198253 A1 | 7/2017 | Laberge et al. |
| 2017/0209435 A1 | 7/2017 | Laberge et al. |
| 2017/0348307 A1 | 12/2017 | Laberge et al. |

FOREIGN PATENT DOCUMENTS

| | | |
|---|---|---|
| WO | WO-03028443 A1 | 4/2003 |
| WO | WO-03051359 A1 | 6/2003 |
| WO | WO-2006018632 A2 | 2/2006 |
| WO | WO-2006039704 A2 | 4/2006 |
| WO | WO-2008113131 A1 | 9/2008 |
| WO | WO-2008125487 A1 | 10/2008 |
| WO | WO-2009039553 A1 | 4/2009 |
| WO | WO-2009105234 A2 | 8/2009 |
| WO | WO-2009151069 A1 | 12/2009 |
| WO | WO-2010080478 A1 | 7/2010 |
| WO | WO-2010148447 A1 | 12/2010 |
| WO | WO-2011068560 A1 | 6/2011 |
| WO | WO-2014186878 A1 | 11/2014 |
| WO | WO-2015051252 A1 | 4/2015 |
| WO | WO-2015066442 A1 | 5/2015 |
| WO | WO-2015116735 A1 | 8/2015 |
| WO | WO-2015116740 A1 | 8/2015 |
| WO | WO-2015181526 A1 | 12/2015 |

OTHER PUBLICATIONS

Hashimoto et al., "Inhibition of MDM2 attenuates neointimal hyperplasia via suppression of vascular proliferation and inflammation," Cardiovascular Research (2011) 91, 711-19. (Year: 2011).*

Ihling et al., "Co-Expression of p53 and MDM2 in Human Atherosclerosis: Implications for the Regulation of Cellularity of Atherosclerotic Lesion," Journal of Pathology, vol. 185: 303-12 (1998) (Year: 1998).*

Bhattacharya, S. et al. Age-Related Susceptibility to Apoptosis in Human Retinal Pigment Epithelial Cells is Triggered by Disruption of p53-Mdm2 Association. Investigative Ophthalmology & Visual Science, 53(13):8350-8366 (Dec. 2012).

Co-pending U.S. Appl. No. 15/950,965, filed Apr. 11, 2018.

Co-pending U.S. Appl. No. 15/955,542, filed Apr. 17, 2018.

Co-pending U.S. Appl. No. 15/981,696, filed May 16, 2018.

Faber, C. et al. Age-related Macular Degeneration is Associated with Increased Proportion of CD56+ T Cells in Peripheral Blood. Ophthalmology, 120(11):2310-2316 (Nov. 2013).

Jakubsick, Claudia et. al. Human Pulmonary Fibroblasts Exhibit Altered Interleukin-4 and Interleukin-13 Receptor Subunit Expression in Idiopathic Interstitial Pneumonia. Am J Pathol. Jun. 2004; 164(6): 1989-2001.

Miyazaki, M. et al. Discovery of novel dihydroimidazothiazole derivatives as p53-MDM2 protein-protein interaction inhibitors: synthesis, biological evaluation and structure-activity relationships. Bioorg Med Chem Lett. Oct. 15, 2012;22(20):6338-42. Epub Aug. 30, 2012.

Miyazaki, M. et al. Lead optimization of novel p53-MDM2 interaction inhibitors possessing dihydroimidazothiazole scaffold. Bioorg Med Chem Lett. Feb. 1, 2013;23(3):728-32. Epub Dec. 1, 2012.

No Author. IDASANUTLIN CAS Registry File (retrieved Jan. 2018). (2018).

No Author. NAVITOCLAX, Retrieved from CAS Registry Jan. 2018. (2018).

No Author. Form S-1 Registration Statement as Filed with the Securities and Exchange Commission on Apr. 23, 2018, pp. 1-243.

U.S. Appl. No. 15/114,762 Final Office Action dated Feb. 5, 2018.

U.S. Appl. No. 15/455,630 Non-Final Office Action dated May 22, 2018.

(56) References Cited

OTHER PUBLICATIONS

U.S. Appl. No. 15/455,684 First Action Interview Office Action Summary dated Apr. 12, 2018.
U.S. Appl. No. 15/647,688 First Action Interview Pilot Program Pre-Interview Communication dated Feb. 6, 2018.
U.S. Appl. No. 15/827,539 First Action Interview Program Pre-Interview Communication dated Feb. 7, 2018.
U.S. Appl. No. 15/955,542 First Action Interview Pilot Program Pre-Interview Communication, dated Jun. 13, 2018.
Uthman, et al. Intra-articular therapy in osteoarthritis. Postgrad Med. J. 79:449-453 (2003). 0.
Zhu, X. et al. Peripheral T Cell Functions Correlate with the Severity of Chronic Obstructive Pulmonary Disease. J. Immunol. 182(5):3270-3277 (Mar. 1, 2009). 0.
Anderson, et al. Why is Osteoarthritis an Age-Related Disease? Best Pract Res Clin Rheumatol. Feb. 2010; 24(1): 15.
Arya, et al. Nutlin-3, the small-molecule inhibitor of MDM2, promotes senescence and radiosensitises laryngeal carcinoma cells harbouring wild-type p53. Br J Cancer. Jul. 13, 2010;103(2):186-95. doi: 10.1038/sj.bjc.6605739. Epub Jun. 29, 2010.
Bajwa, et al. Inhibitors of the anti-apoptotic Bcl-2 proteins: a patent review. Expert Opin Ther Pat. Jan. 2012;22(1):37-55. doi: 10.1517/13543776.2012.644274. Epub Dec. 23, 2011.
Baker, et al. Clearance of p16Ink4a-positive senescent cells delays ageing-associated disorders. Nature 479(7372):232-236 (2011).
Barak, et al. mdm2 expression is induced by wild type p53 activity. EMBO J. Feb. 1993;12(2):461-8.
Brenkman, et al. Mdm2 induces mono-ubiquitination of FOXO4. PLoS One. Jul. 30, 2008;3(7):e2819. doi: 10.1371/journal.pone.0002819.
Campisi, et al. Cell senescence: role in aging and age-related diseases. Interdiscip Top Gerontol. 2014;39:45-61. doi: 10.1159/000358899. Epub May 13, 2014.
Campisi, J. Cellular senescence as a tumor-suppressor mechanism. Trends Cell Biol. Nov. 2001;11(11):S27-31.
Campisi, J. Cellular senescence: putting the paradoxes in perspective. Curr Opin Genet Dev. Feb. 2011;21(1):107-12. doi: 10.1016/j.gde.2010.10.005. Epub Nov. 17, 2010.
Campisi, J. Senescent cells, tumor suppression, and organismal aging: good citizens, bad neighbors. Cell. Feb. 25, 2005;120(4):513-22.
Caruso, et al. Apoptotic-like tumor cells and apoptotic neutrophils in mitochondrion-rich gastric adenocarcinomas: a comparative study with light and electron microscopy between these two forms of cell death. Rare Tumors. Jun. 7, 2013;5(2):68-71. doi: 10.4081/rt.2013.e18. Print Apr. 15, 2013.
Chang, et al. Clearance of senescent cells by ABT263 rejuvenates aged hematopoietic stem cells in mice. Nat Med. Dec. 14, 2015. doi: 10.1038/nm.4010.
Co-pending U.S. Appl. No. 15/481,129, filed Apr. 6, 2017.
Coppe, et al. A Human-Like Senescence-Associated Secretory Phenotype is Conserved in Mouse Cells Dependent on Physiological Oxygen. PLoS One 5:e9188 (2010).
Coppe, et al. Senescence-associated secretory phenotypes reveal cell-nonautonomous functions of oncogenic RAS and the p53 tumor suppressor. PLoS Biol. Dec. 2, 2008;6(12):2853-68. doi: 10.1371/journal.pbio.0060301.
Doroshevskaya, et al. Apoptosis Regulator Proteins: Basis for the Development of Innovation Strategies for the Treatment of Rheumatoid Arthritis in Patients of Different Age. Bulletin of Experimental Biology and Medicine. Jan. 2014, vol. 156, Issue 3, pp. 377-380.
Efeyan, et al. Induction of p53-dependent senescence by the MDM2 antagonist nutlin-3a in mouse cells of fibroblast origin. Cancer Res. Aug. 1, 2007;67(15):7350-7.
Extended European Search Report and Search Opinion dated Aug. 28, 2017 for European Patent Application No. EP15743068.7.
First Action Interview Pilot Program Pre-Interview Communication dated May 16, 2017 for U.S. Appl. No. 15/455,575.

Freund, et al. p38MAPK is a novel DNA damage response-independent regulator of the senescence-associated secretory phenotype. EMBO J. Apr. 20, 2011;30(8):1536-48. doi: 10.1038/emboj.2011.69. Epub Mar. 11, 2011.
Gagarina, et al. SirT1 enhances survival of human osteoarthritic chondrocytes by repressing protein tyrosine phosphatase 1B and activating the insulin-like growth factor receptor pathway. Arthritis Rheum. May 2010;62(5):1383-92.
Golstein, et al. Cell death by necrosis: towards a molecular definition. Trends in Biochemical Sciences. vol. 32, Issue 1, p. 37-43, Jan. 2007.
Guan, et al. Imidazoline derivatives: a patent review (2006—present). Expert Opin Ther Pat. Nov. 2012;22(11):1353-65. doi: 10.1517/13543776.2012.727397. Epub Sep. 24, 2012.
Hashimoto, et al. Role of p53 in human chondrocyte apoptosis in response to shear strain. Arthritis Rheum. Aug. 2009;60(8):2340-9.
Haupt, et al. Mdm2 promotes the rapid degradation of p53. Nature. May 15, 1997;387(6630):296-9.
Holford, et al. Pharmacokinetics & Pharmacodynamics: Dose Selection & the Time Course of Drug Action. From Basic & Clinical Pharmacology, 7th Ed.. 1989. Edited by Katzung, B. Appleton & Lange (Stamford, Connecticut). pp. 34-49.
Honda, et al. Oncoprotein MDM2 is a ubiquitin ligase E3 for tumor suppressor p53. FEBS Lett. Dec. 22, 1997;420(1):25-7.
Huang, et al. Reduced transcriptional activity in the p53 pathway of senescent cells revealed by the MDM2 antagonist nutlin-3. Aging (Albany NY). Oct. 2009; 1(10): 845-854. Published online Sep. 25, 2009. doi: 10.18632/aging.100091.
International Preliminary Report on Patentability dated Aug. 2, 2016 for International PCT Patent Application No. PCT/US2015/013376.
International Preliminary Report on Patentability dated Aug. 2, 2016 for International PCT Patent Application No. PCT/US2015/013387.
Jeon, et al. Local clearance of senescent cells attenuates the development of post-traumatic osteoarthritis and creates a pro-regenerative environment. Nat Med. Jun. 2017;23(6):775-781. doi: 10.1038/nm.4324. Epub Apr. 24, 2017.
Juven, et al. Wild type p53 can mediate sequence-specific transactivation of an internal promoter within the mdm2 gene. Oncogene. Dec. 1993;8(12):3411-6.
Kerr, et al. Apoptosis: a basic biological phenomenon with wide-ranging implications in tissue kinetics. Br J Cancer. Aug. 1972;26(4):239-57.
Kroemer, et al. Classification of cell death: recommendations of the Nomenclature Committee on Cell Death 2009. Cell Death Differ. Jan. 2009; 16(1): 3-11.
Kubbutat, et al. Regulation of p53 stability by Mdm2. Nature. May 15, 1997;387(6630):299-303.
Laberge, et al. Glucocorticoids suppress selected components of the senescence-associated secretory phenotype. Aging Cell 11(4):569-578, 2012.
Laberge, et al. Mitochondrial DNA damage induces apoptosis in senescent cells. Cell Death Dis. Jul. 18, 2013;4:e727. doi: 10.1038/cddis.2013.199.
Lahav, Galit. Oscillations by the p53-Mdm2 feedback loop. Adv Exp Med Biol. 2008;641:28-38.
Leist, et al. Four deaths and a funeral: from caspases to alternative mechanisms. Nat Rev Mol Cell Biol. Aug. 2001;2(8):589-98.
Lessene; et al., Structure-guided design of a selective BCL-X(L) inhibitor., Jun. 2013, 9(6), 390-7.
Loeser, Richard F. Aging and Osteoarthritis: The Role of Chondrocyte Senescence and Aging Changes in the Cartilage Matrix. Osteoarthritis Cartilage. Aug. 2009; 17(8): 971-979. Published online Mar. 12, 2009. doi: 10.1016/j.joca.2009.03.002.
Manfredi, James. The Mdm2-p53 relationship evolves: Mdm2 swings both ways as an oncogene and a tumor suppressor. Genes Dev. Aug. 1, 2010;24(15):1580-9. doi: 10.1101/gad.1941710.
Martin, et al. Chondrocyte senescence, joint loading and osteoarthritis. Clin Orthop Relat Res. Oct. 2004;(427 Suppl):S96-103.
Momand, et al. The mdm-2 oncogene product forms a complex with the p53 protein and inhibits p53-mediated transactivation. Cell. Jun. 26, 1992;69(7):1237-45.

(56) References Cited

OTHER PUBLICATIONS

Notice of Allowance dated Aug. 3, 2017 and corresponding allowed claims for U.S. Appl. No. 15/467,129.
Notice of Allowance dated Aug. 18, 2017 and corresponding allowed claims for U.S. Appl. No. 15/455,575.
Office Communication dated Jul. 21, 2017 for U.S. Appl. No. 15/467,129.
Office Communication dated Sep. 14, 2017 for U.S. Appl. No. 15/114,762.
Office Communication dated Sep. 27, 2017 for U.S. Appl. No. 15/481,129.
Oliner, et al. Oncoprotein MDM2 conceals the activation domain of tumour suppressor p53. Nature. Apr. 29, 1993;362(6423):857-60.
Perry, et al. The mdm-2 gene is induced in response to UV light in a p53-dependent manner. Proc Natl Acad Sci U S A. Dec. 15, 1993;90(24):11623-7.
Prieur, et al. Cellular senescence in vivo: a barrier to tumorigenesis. Curr Opin Cell Biol. Apr. 2008;20(2):150-5. doi: 10.1016/j.ceb.2008.01.007. Epub Mar. 18, 2008.
Rodier, et al. Persistent DNA damage signalling triggers senescence-associated inflammatory cytokine secretion. Nat Cell Biol. Aug. 2009;11(8):973-9. doi: 10.1038/ncb1909. Epub Jul. 13, 2009.
SĄczewski, et al. Imidazoline Scaffold in Medicinal Chemistry: A Patent Review (2012-2015). Expert Opin Ther Pat 26 (9), 1031-1048. Jul. 20, 2016.
Shangary, et al. Temporal activation of p53 by a specific MDM2 inhibitor is selectively toxic to tumors and leads to complete tumor growth inhibition. Proc Natl Acad Sci U S A. Mar. 11, 2008;105(10):3933-8. doi: 10.1073/pnas.0708917105. Epub Mar. 3, 2008.
Taranto, et al. Detection of the p53 regulator murine double-minute protein 2 in rheumatoid arthritis. J Rheumatol. Mar. 2005;32(3):424-9.
Thomasova, et al. p53-Independent Roles of MDM2 in NF-κB Signaling: Implications for Cancer Therapy, Wound Healing, and Autoimmune Diseases. Neoplasia. Dec. 2012; 14(12): 1097-1101.
Tovar, et al. MDM2 small-molecule antagonist RG7112 activates p53 signaling and regresses human tumors in preclinical cancer models. Cancer Res. Apr. 15, 2013;73(8):2587-97. doi: 10.1158/0008-5472.CAN-12-2807. Epub Feb. 11, 2013.
UAMS News Bureau. UAMS Research Findings Show Radiation, Aging Effects Can Be Cleared with Drug; Findings Published in Nature Medicine. www.uamshealth.com/news. Dec. 14, 2015. 2 pages.
Uraoka, et al. Loss of bcl-2 during the senescence exacerbates the impaired angiogenic functions in endothelial cells by deteriorating the mitochondrial redox state. Hypertension. Aug. 2011;58(2):254-63. doi: 10.1161/HYPERTENSIONAHA.111.176701. Epub Jul. 5, 2011.
Van Deursen, Jan M. The role of senescent cells in ageing. Nature. May 22, 2014;509(7501):439-46. doi: 10.1038/nature13193.
Vassilev, et al. In vivo activation of the p53 pathway by small-molecule antagonists of MDM2. Science. Feb. 6, 2004;303(5659):844-8. Epub Jan. 2, 2004.
Wang. Senescent human fibroblasts resist programmed cell death, and failure to suppress bcl2 is involved. Cancer Res. Jun. 1, 1995;55(11):2284-92.
Zauli, et al. Dasatinib plus Nutlin-3 shows synergistic antileukemic activity in both p53 wild-type and p53 mutated B chronic lymphocytic leukemias by inhibiting the Akt pathway. Clin Cancer Res. Feb. 15, 2011;17(4):762-70. doi: 10.1158/1078-0432.CCR-10-2572. Epub Nov. 24, 2010.
Zhang, et al. MDM2 Promotes Rheumatoid Arthritis via Activation of MAPK and NF-κB. Int Immunopharmacol 30, 69-73. Dec. 2, 2015.
Zhao, et al. Small molecule inhibitors of MDM2-p53 and MDMX-p53 interactions as new cancer therapeutics. BioDiscovery, 8. 2013; 8(4).15 pages.
Zhu, et al. Identification of a novel senolytic agent, navitoclax, targeting the Bcl-2 family of anti-apoptotic factors. Aging Cell. Jun. 2016;15(3):428-35. doi: 10.1111/acel.12445. Epub Mar. 18, 2016.
Co-pending U.S. Appl. No. 15/827,539, filed Nov. 30, 2017.
Gannon et al., Mdm2-p53 signaling regulates epidermal stem cell senescence and premature aging phenotypes in mouse skin. Developmental Biology, 353:1-9, 2011.
Ianitti, et al. Intra-articular injections for the treatment of osteoarthritis: focus on the clinical use of hyaluronic acid. Drugs R D. 2011;11(1):13-27.
Office Action dated May 17, 2017 for U.S. Appl. No. 15/069,769.
U.S. Appl. No. 15/455,630 Non-Final Office Action dated Nov. 28, 2017.
U.S. Appl. No. 15/481,129 First Action Interview dated Nov. 20, 2017.
U.S. Appl. No. 15/455,684 First Action Interview Pilot Program, Pre-Interview Communication, dated Dec. 15, 2017.

\* cited by examiner

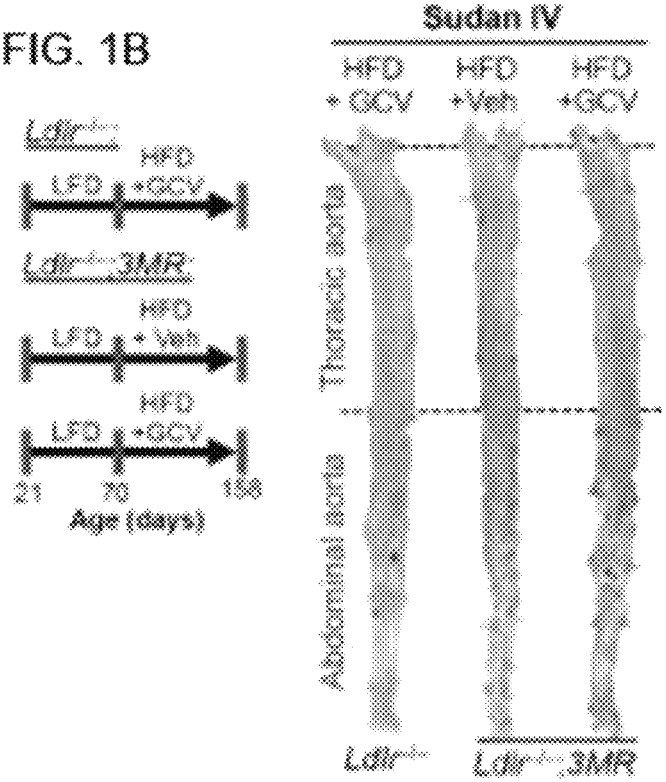

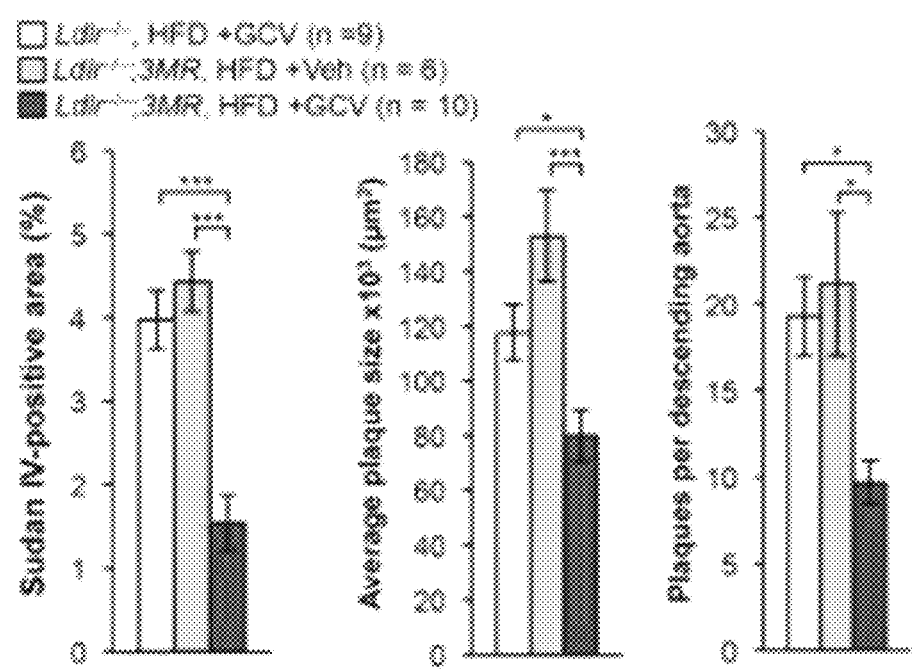

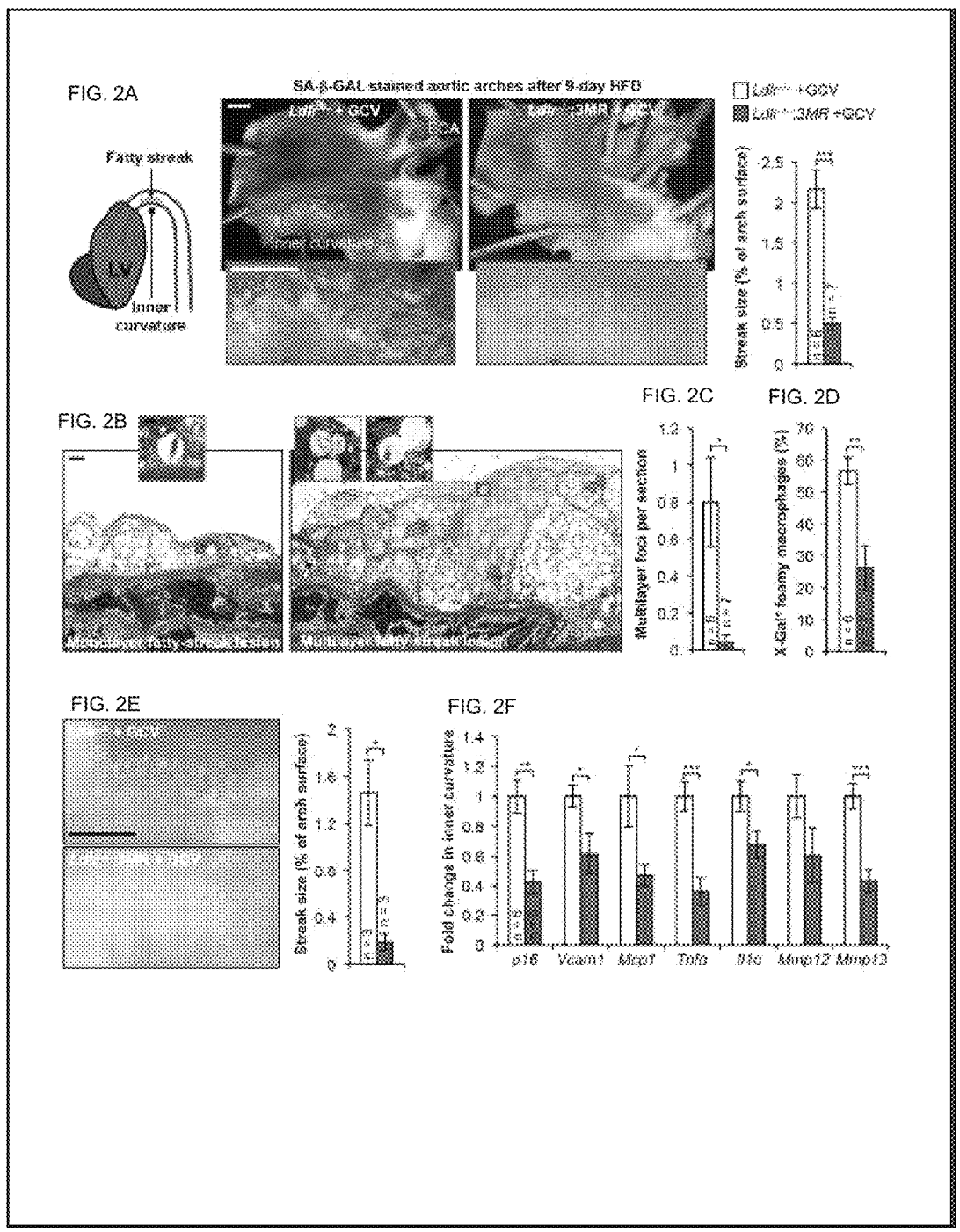

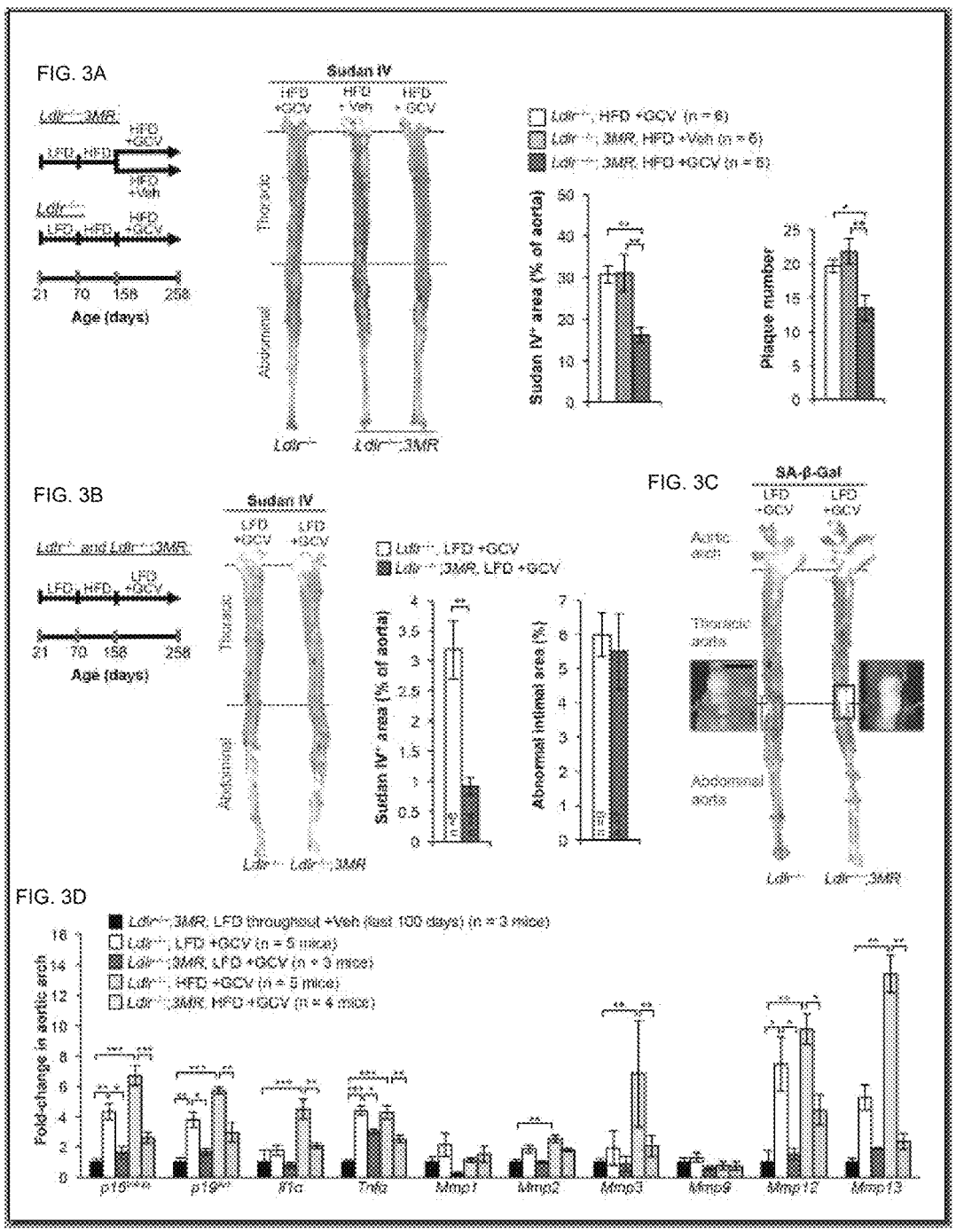

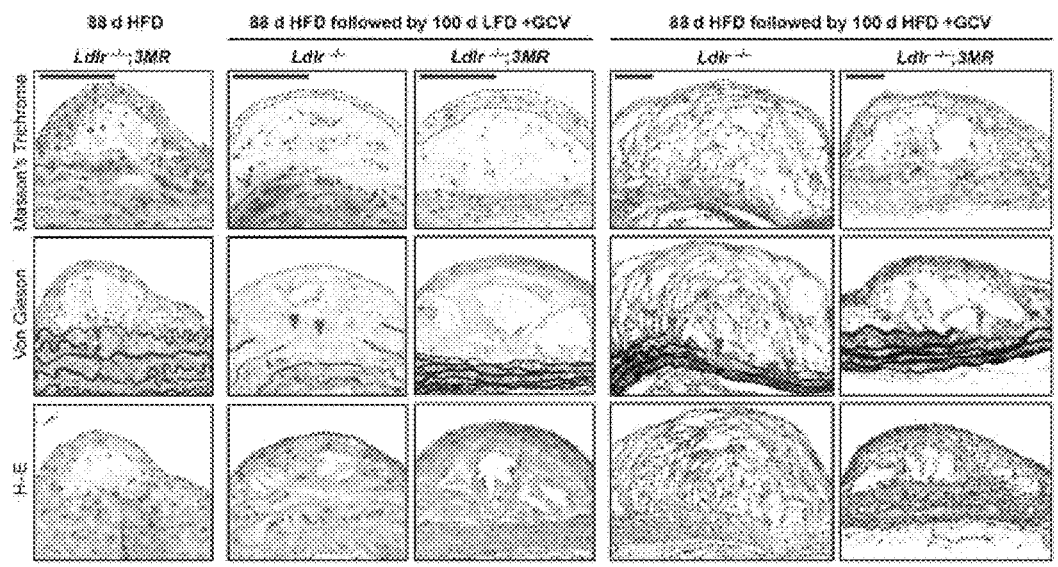
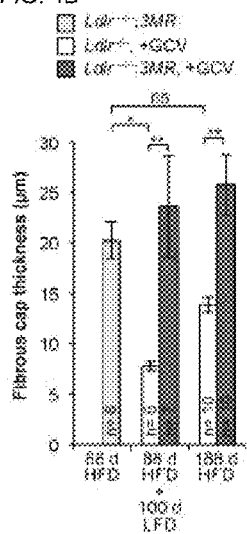
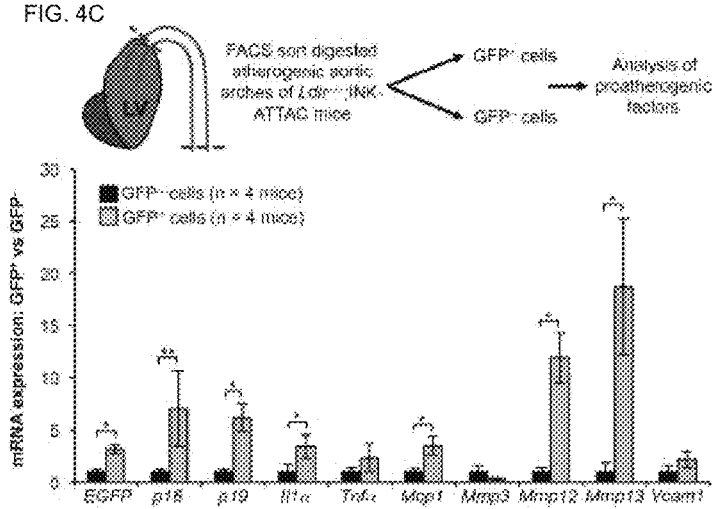

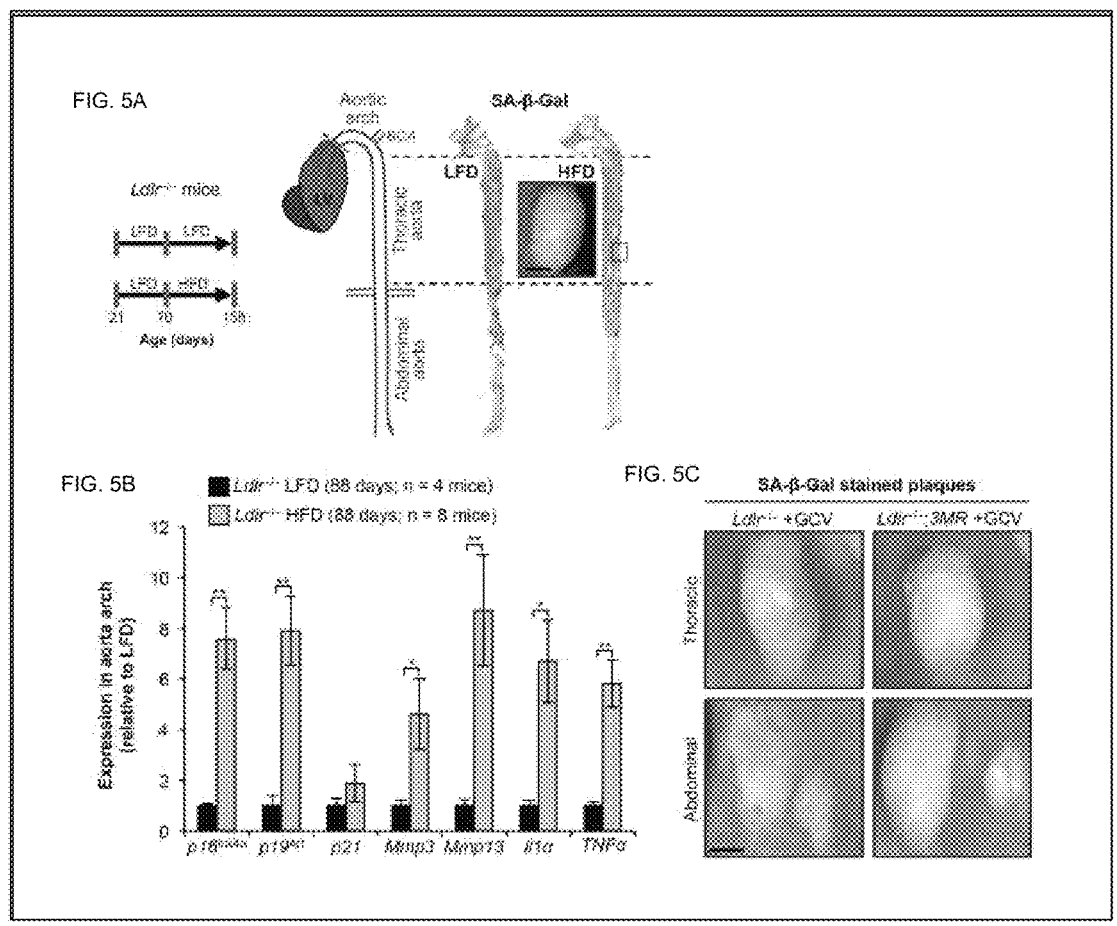
Senescent cells accumulate in atherosclerotic plaques and are cleared by p16-3MR.

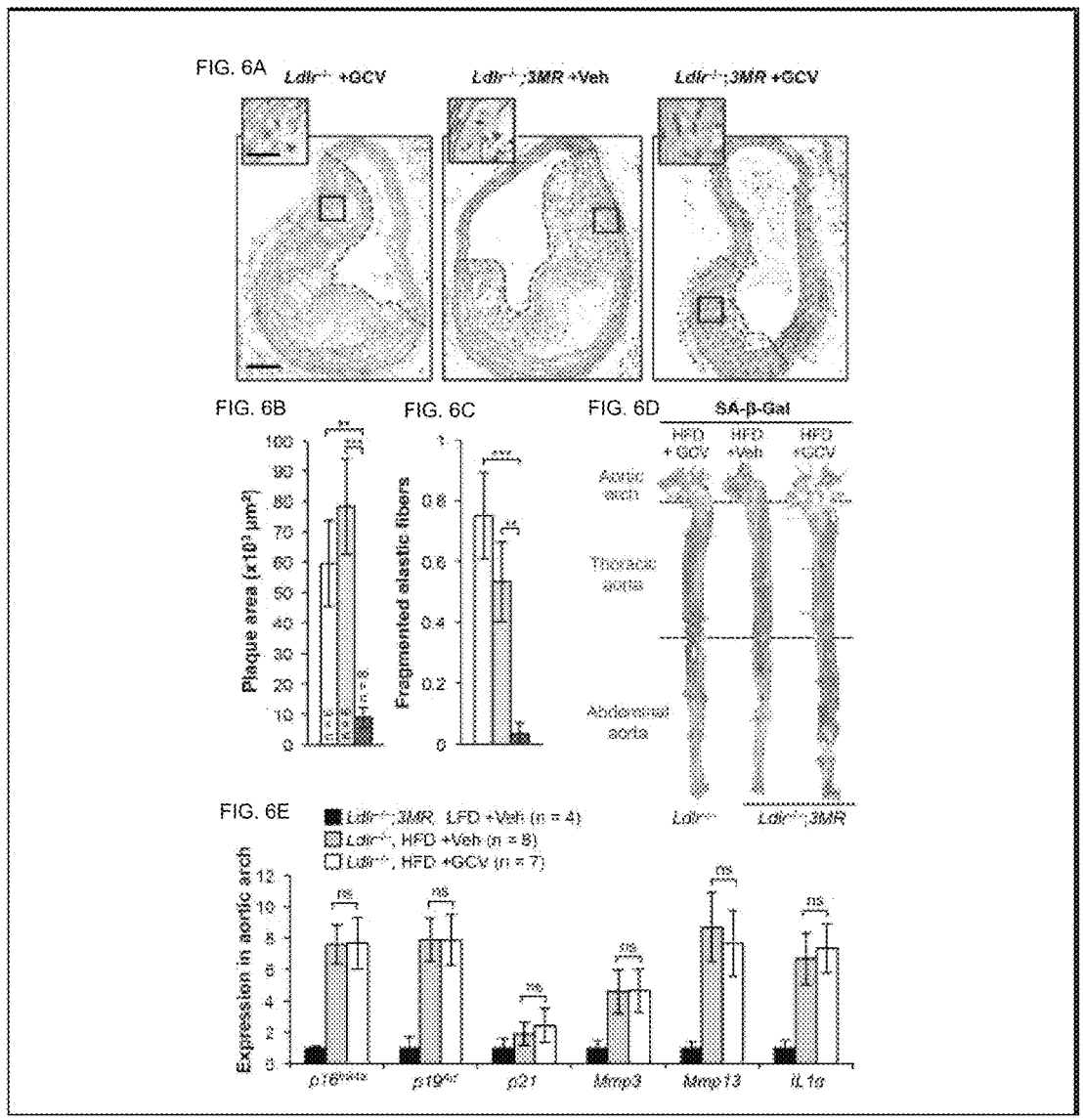
Senescent cell clearance is athero-protective in the brachiocephalic artery.

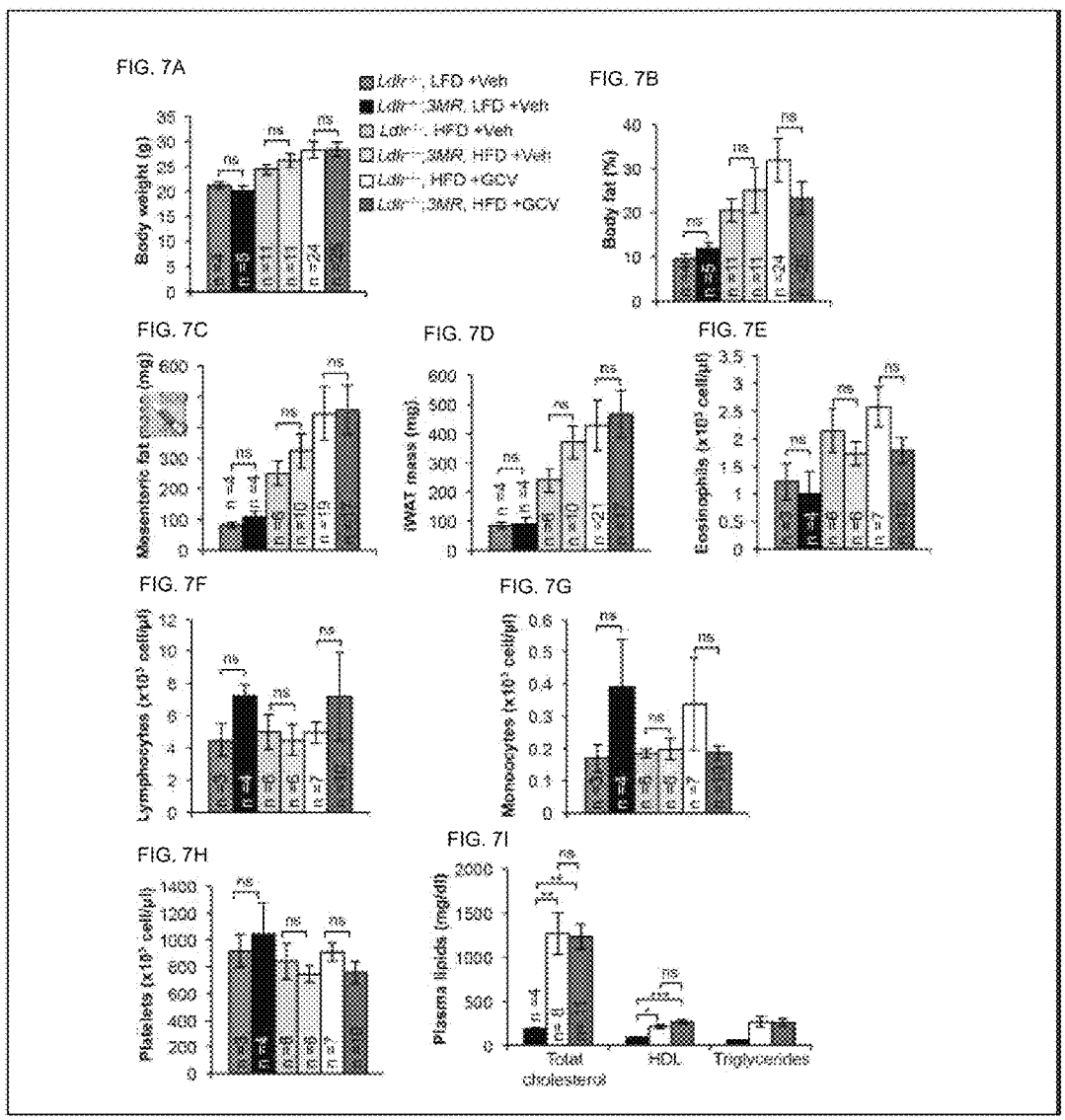
Parameters that modulate atherosclerosis are not impacted by $16^{Ink4a}+$ cell killing or GCV.

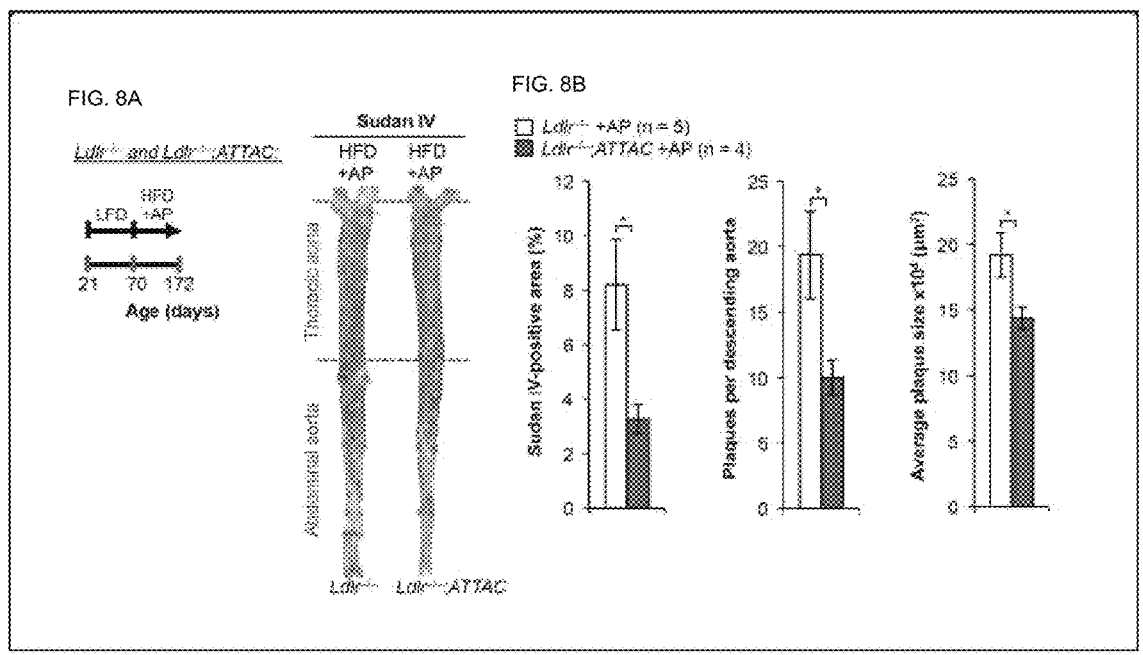
*INK_ATTAC*-mediated senescent cell killing blunts atherogenesis.

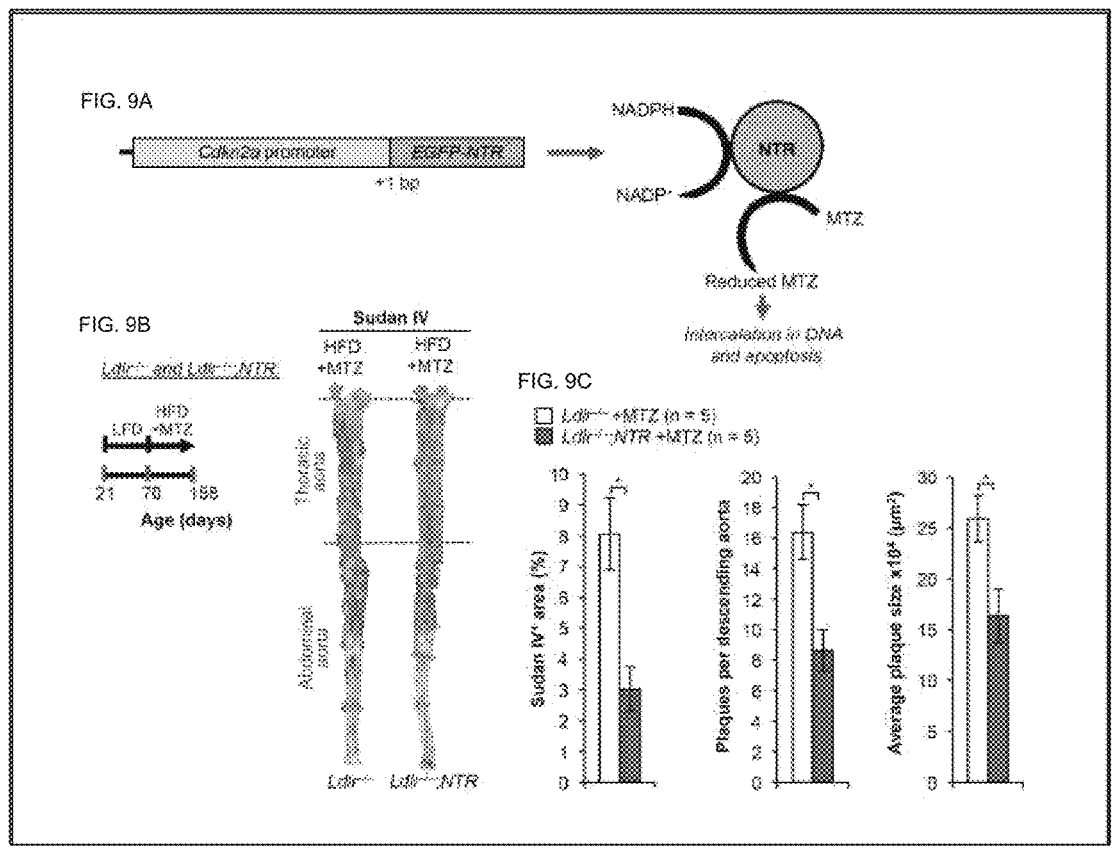
Senescent cell killing by *INK-NTR* attenuates plaque initiation and growth

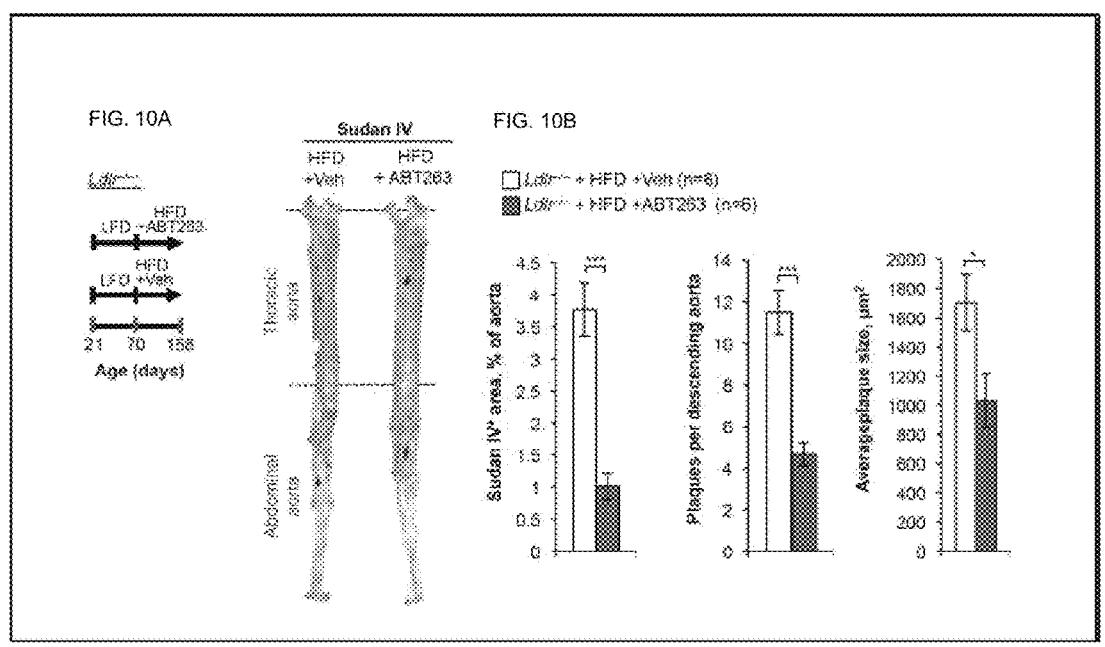
ABT263-mediated senescent cell clearance inhibits atherogenesis.

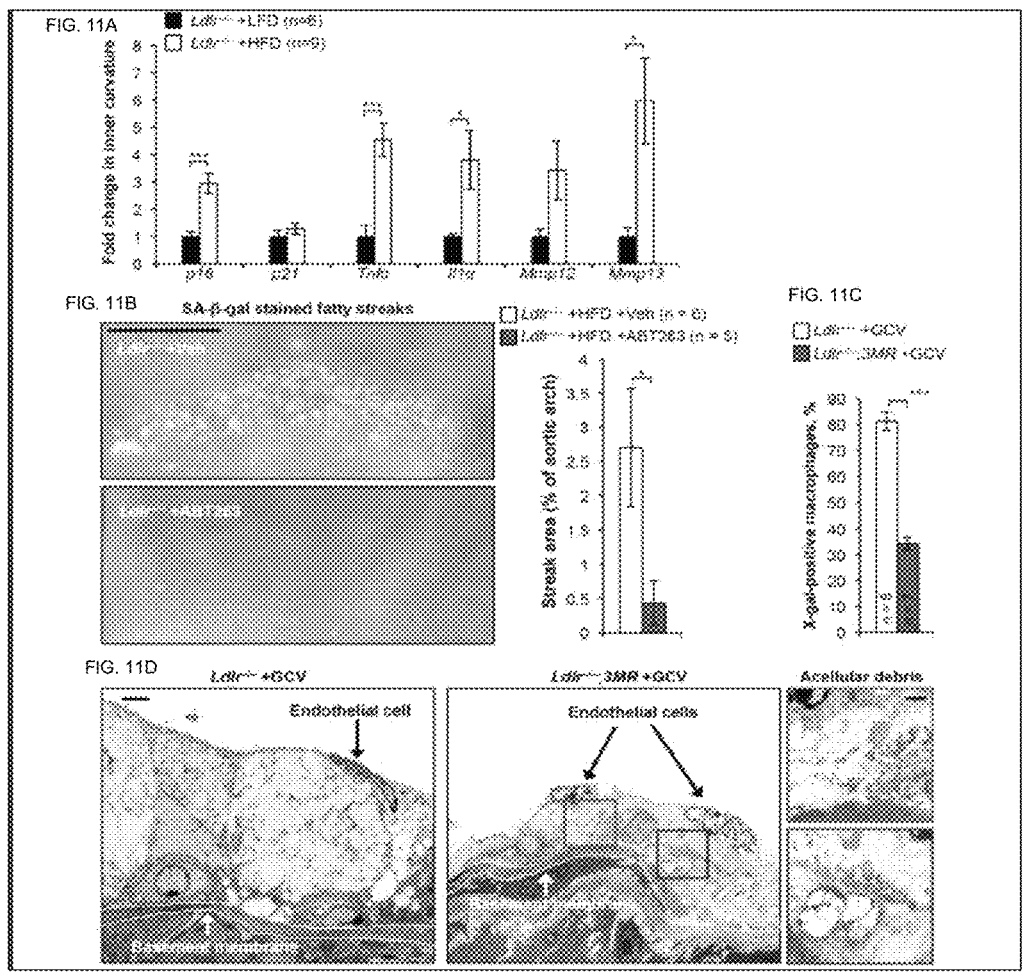
Transgenic and pharmacological elimination of senescent cells inhibits fatty streak formation.

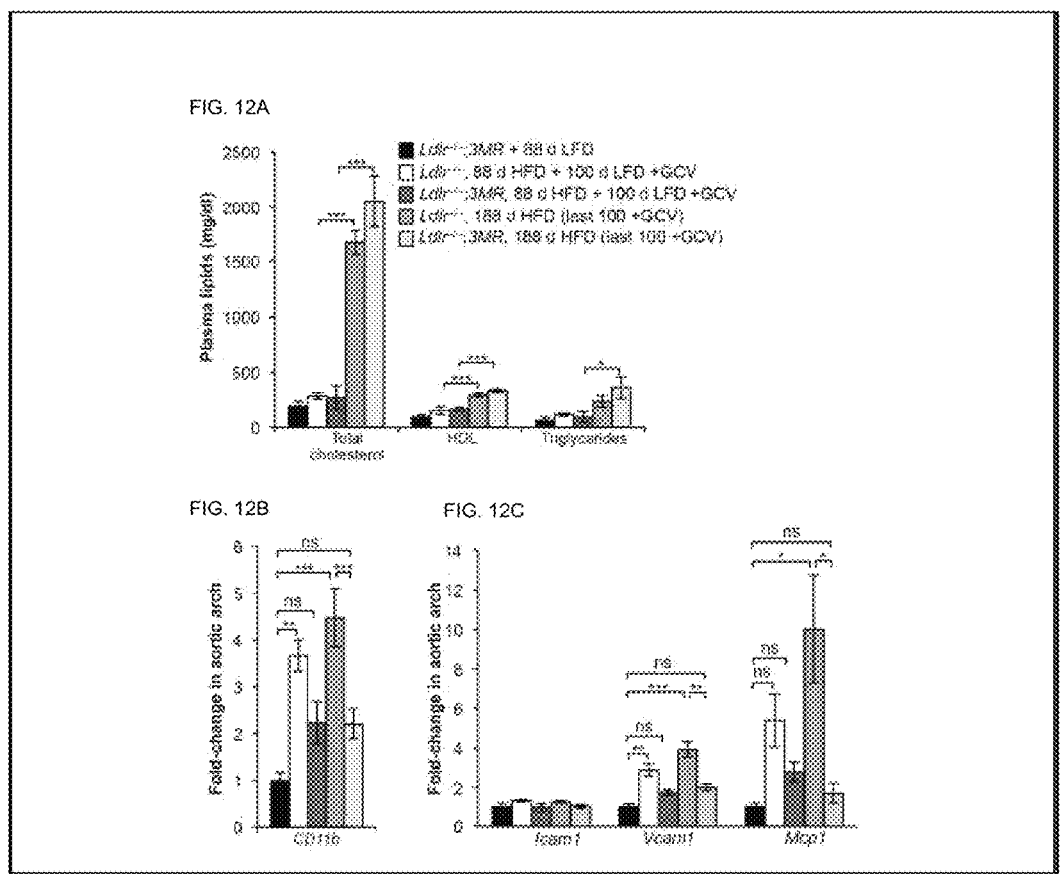
Senescent cell killing in advanced plaques reduces monocyte chemotactic factors without impacting plasma lipids.

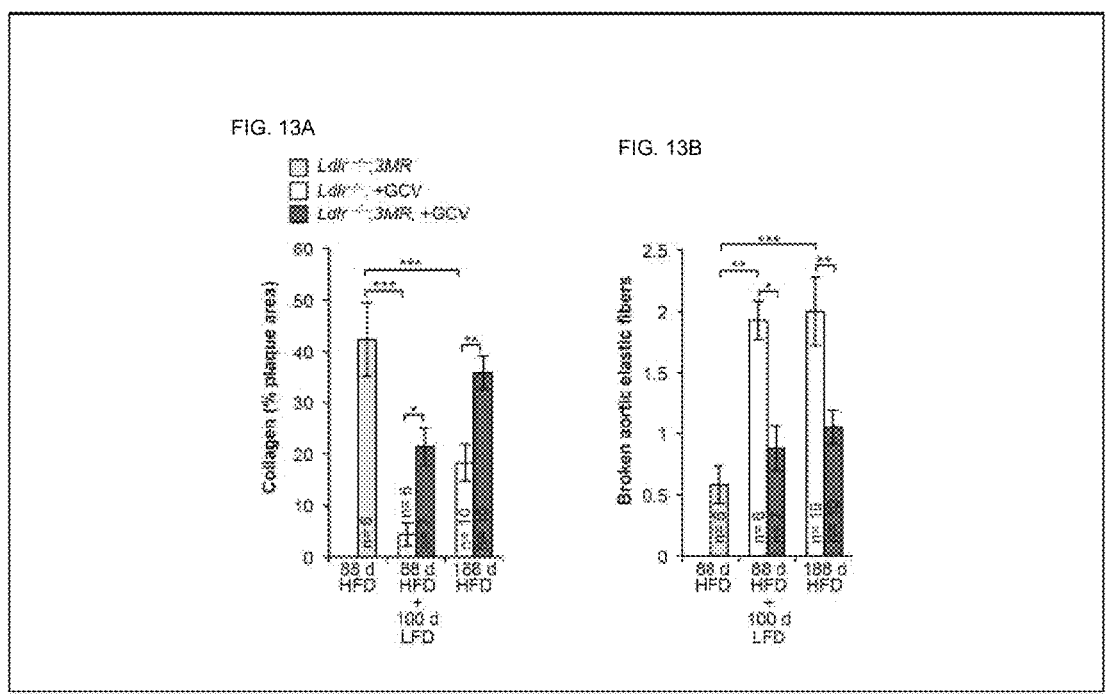
Senescent cells reduce collagen and elastin content in advanced plaques.

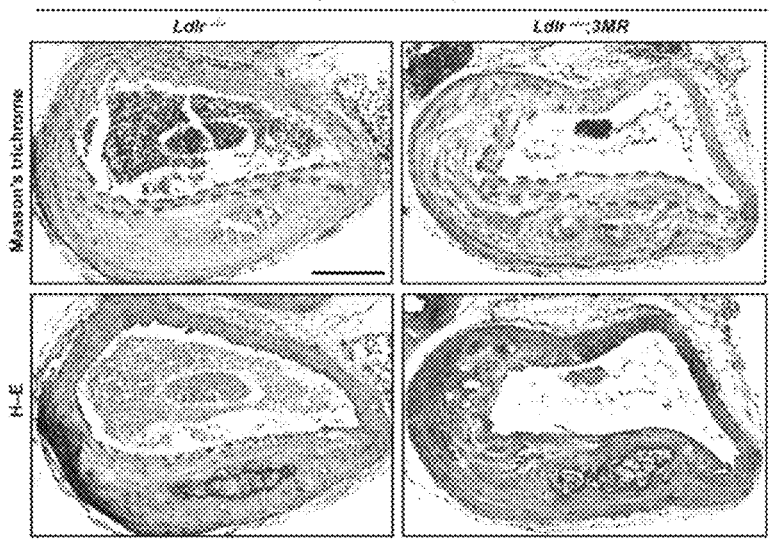
FIG. 14A
FIG. 14B
FIG. 14C
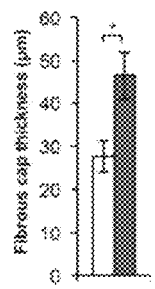
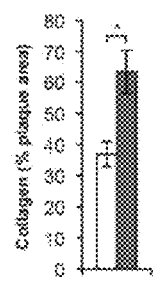
Senescent cell clearance increases fibrous cap thickness and collagen content in brachiocephalic artery plaques.

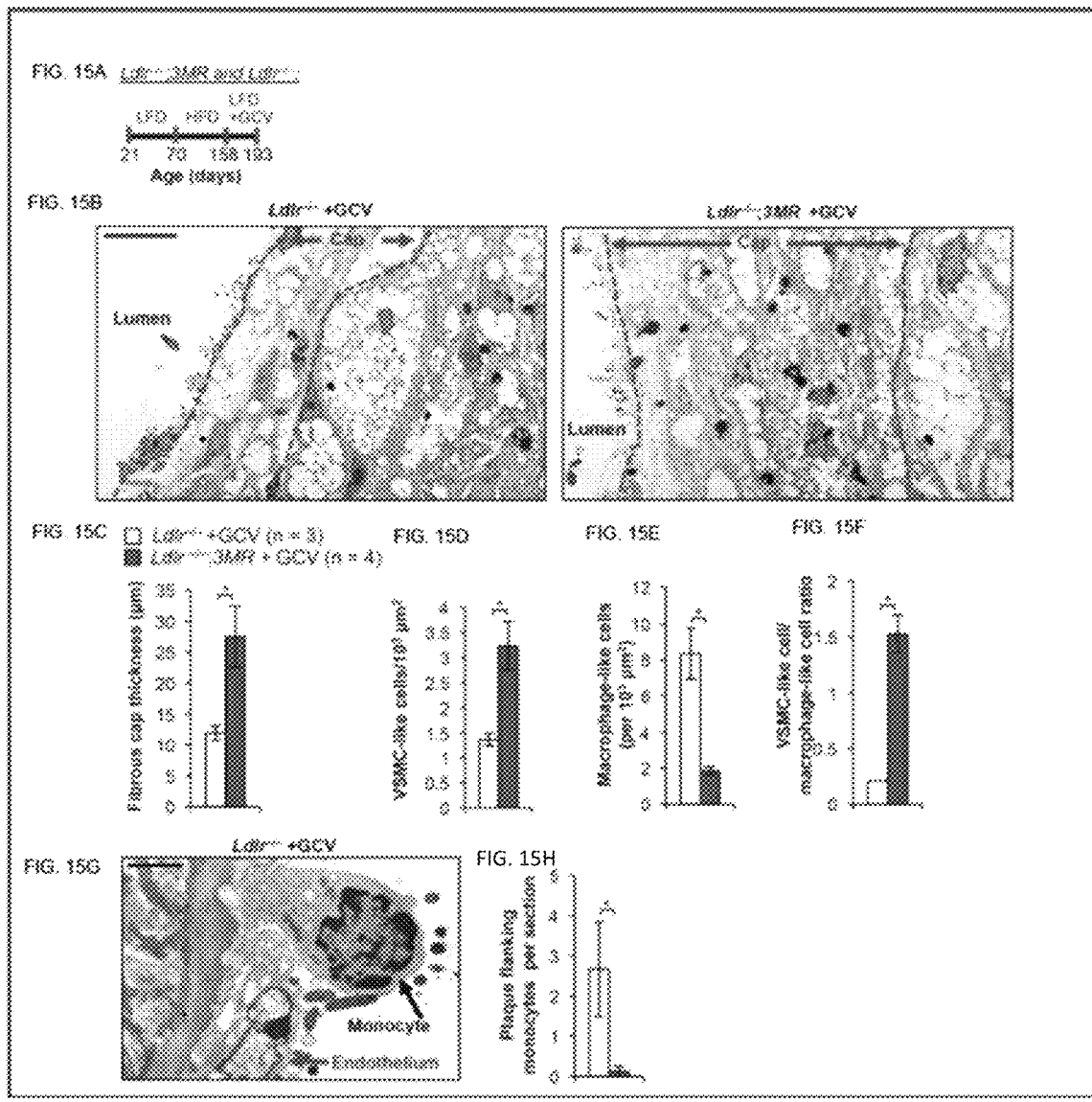
Established plaques are stabilized by short-term senescent cell removal.

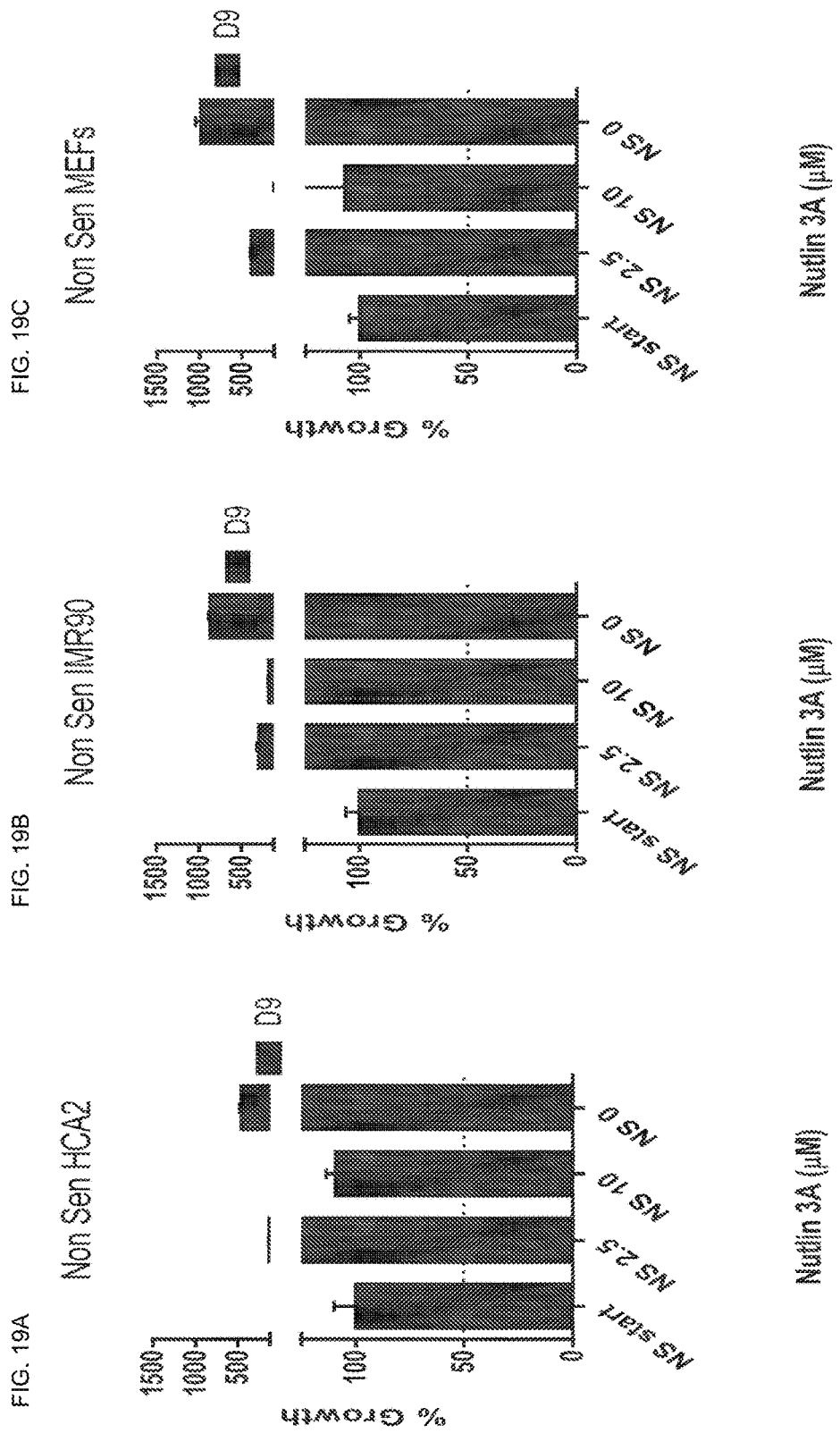

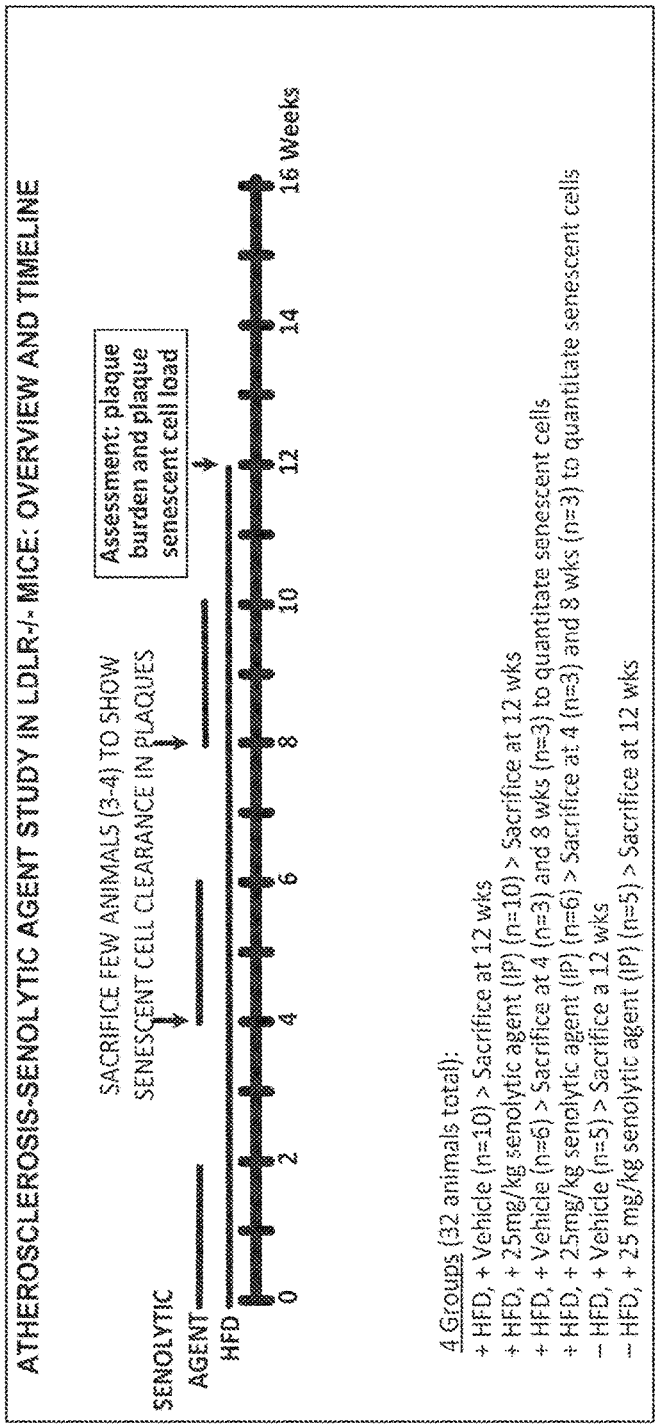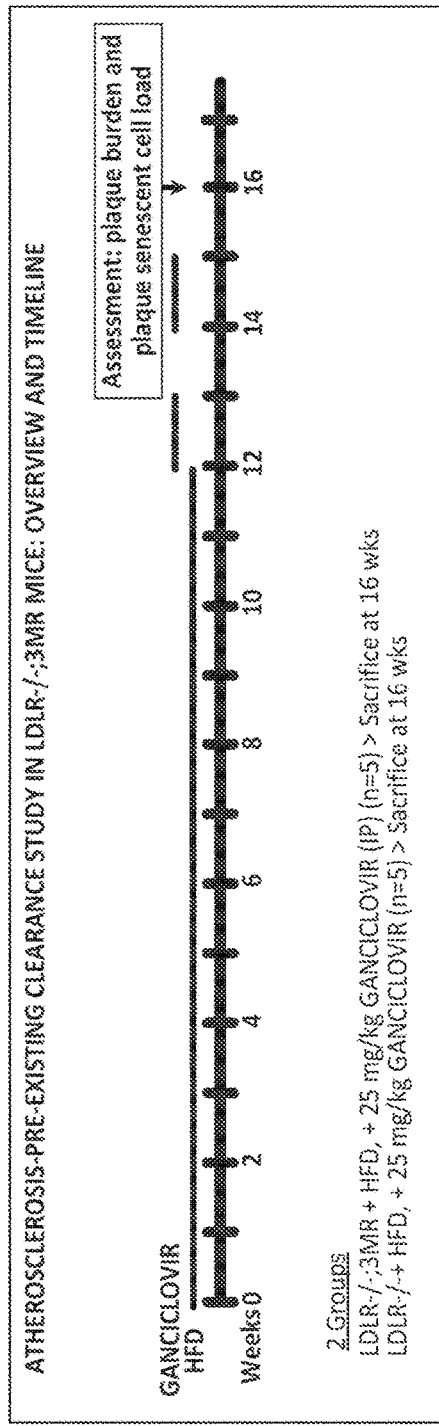
FIG. 21A
FIG. 21B

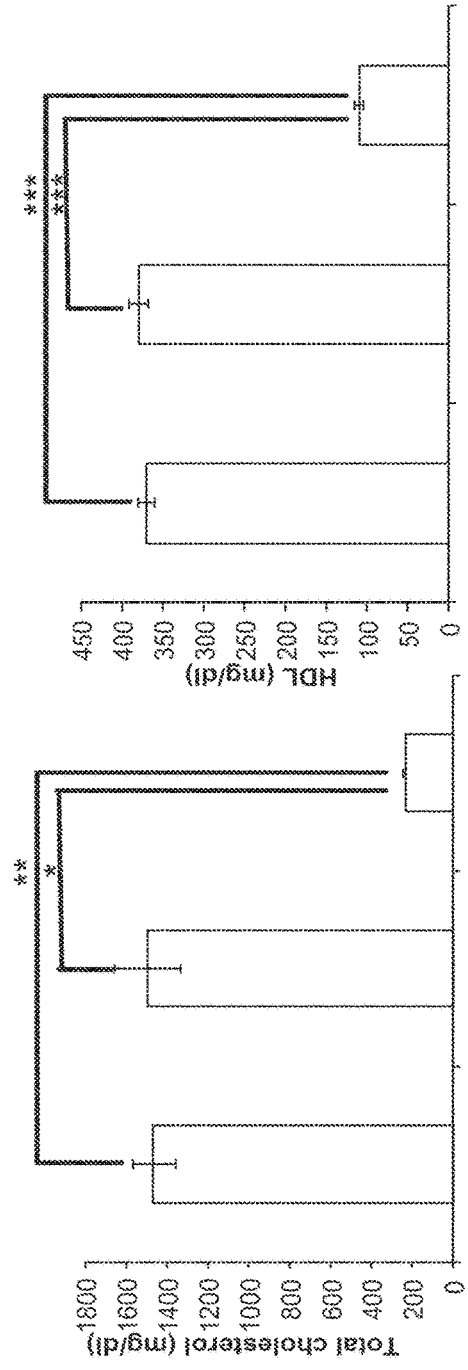
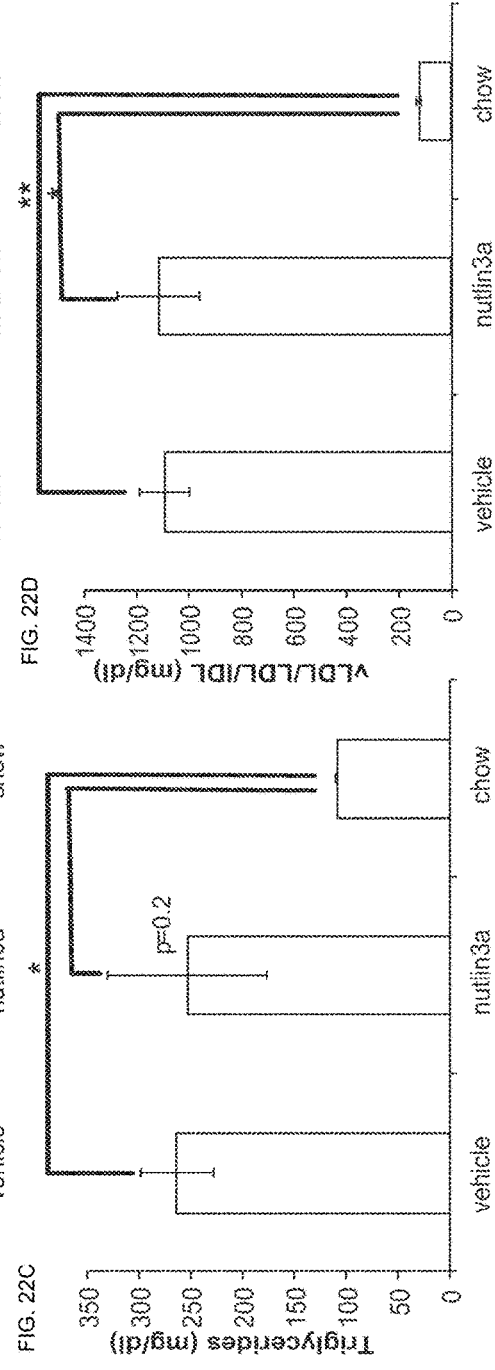
FIG. 22A
FIG. 22B
FIG. 22C
FIG. 22D

| Group | | IL6 | mmp1 | mmp3 | mmp13 | pai1 | p21 | igfbp2 | il1a | il1b |
|---|---|---|---|---|---|---|---|---|---|---|
| hi-fat+nutlin3a | versus hi-fat + vehicle | 0.055 | 0.632 | 0.448 | 0.064 | 0.129 | 0.902 | 0.158 | 0.041 | 0.379 |
| | versus chow + vehicle | 0.532 | 0.664 | 0.348 | 0.270 | 0.005 | 0.238 | 0.244 | 0.505 | 0.290 |
| hi-fat+vehicle | versus chow + vehicle | 0.077 | 0.878 | 0.455 | 0.914 | 0.575 | 0.072 | 0.279 | 0.193 | 0.241 |

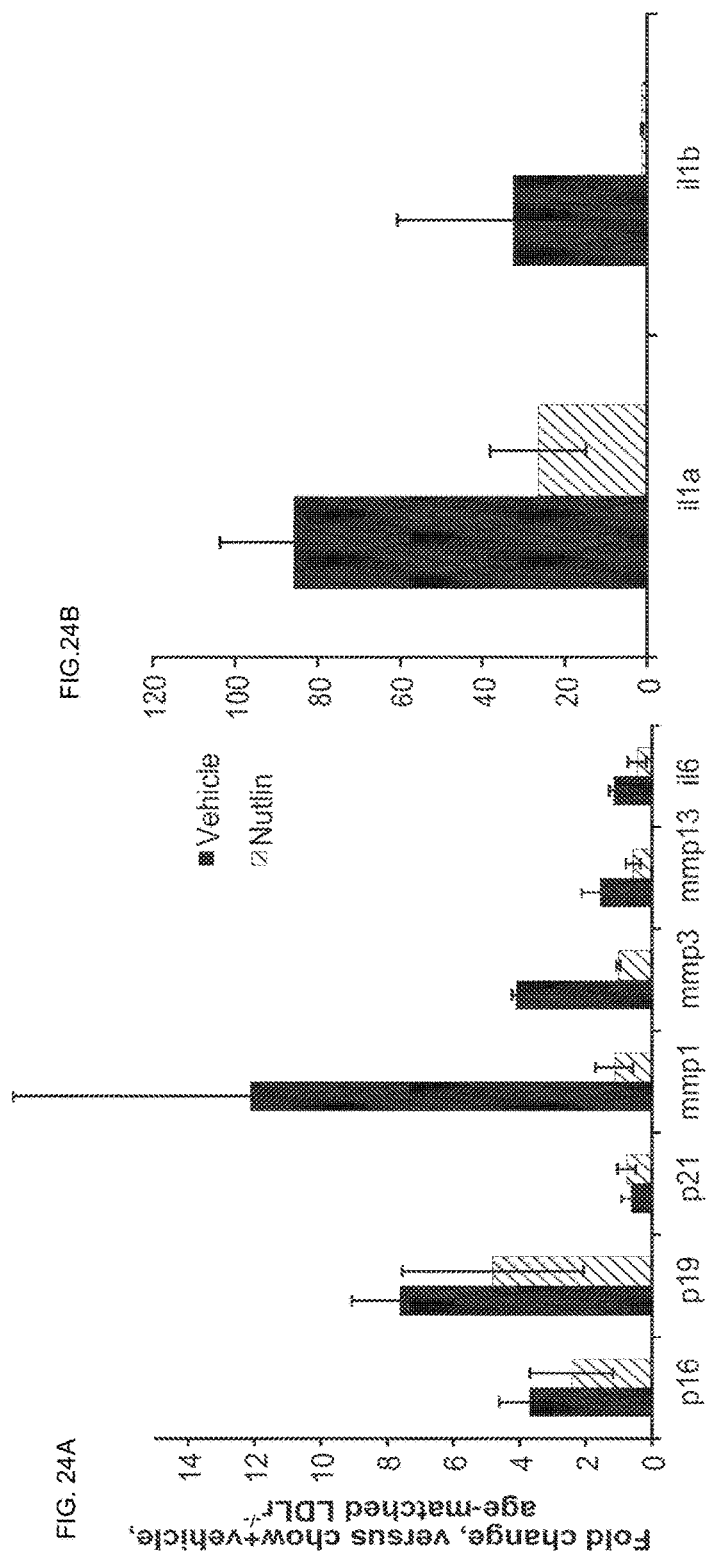
FIG. 24A
FIG. 24B
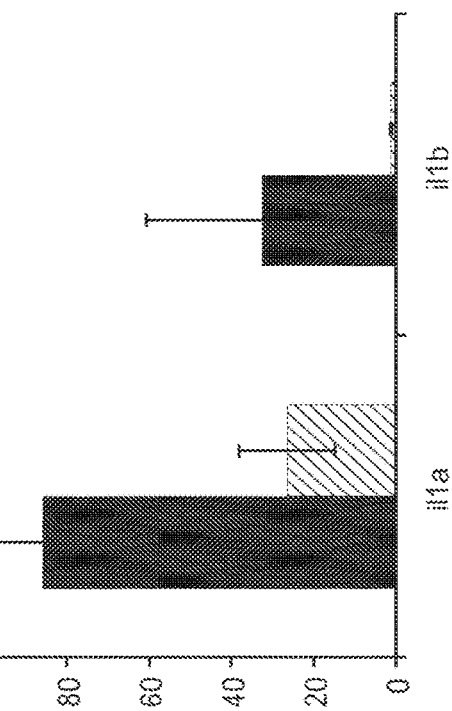
FIG. 24C

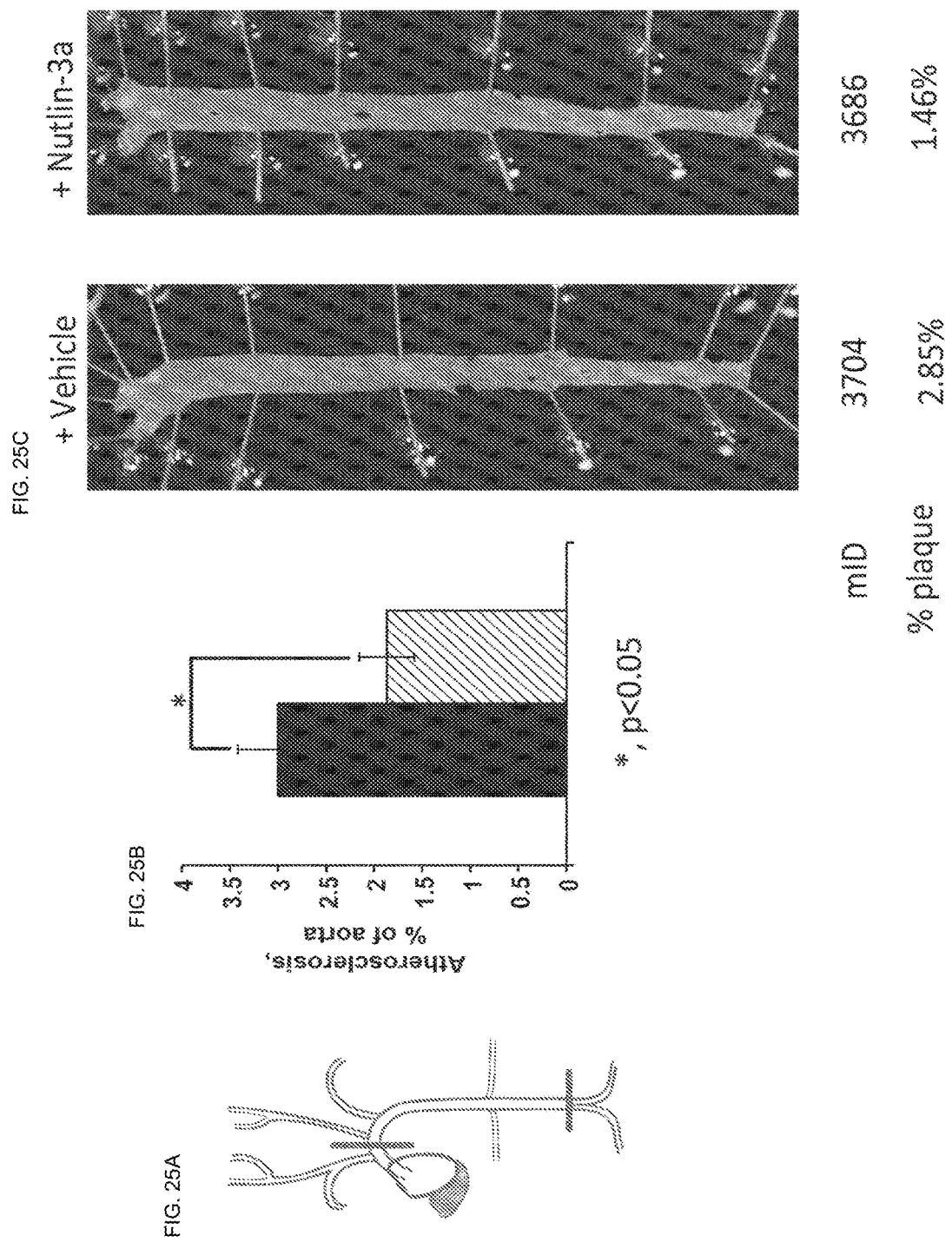

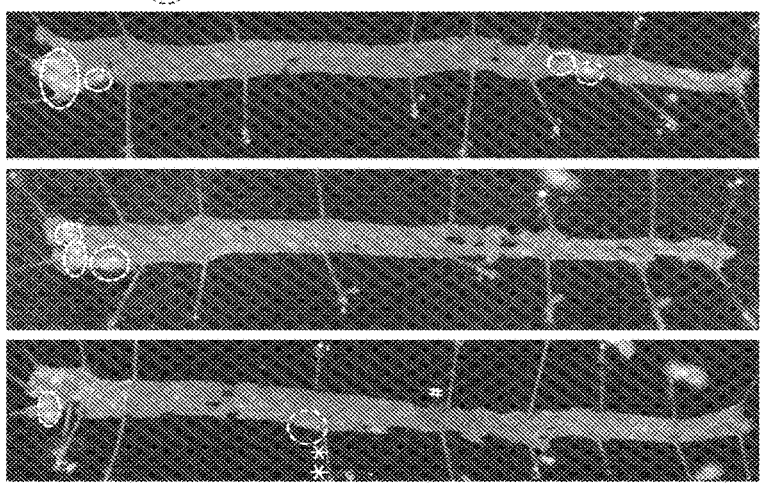
FIG. 31A LDLr-/- descending aortas
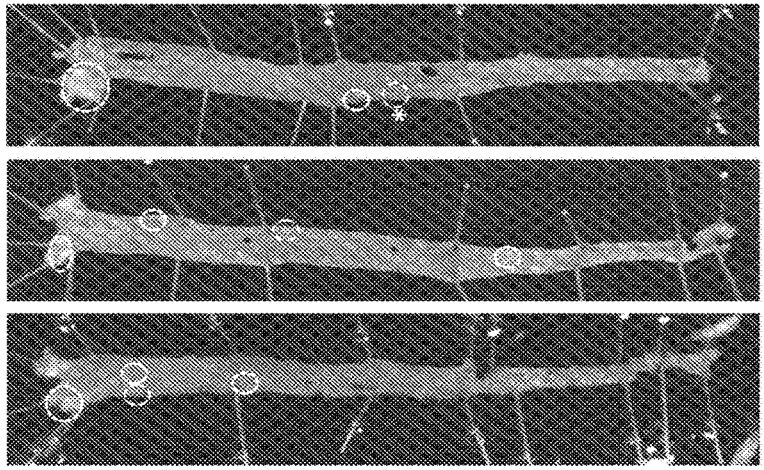
FIG. 31C LDLr-/- descending aortas
⊙ Plaques that were harvested are marked with dashed circles
\# marks fat on outside of aorta
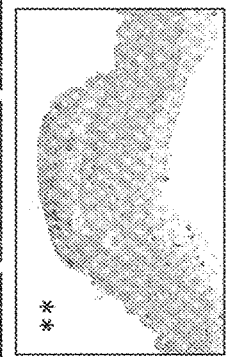
FIG. 31B "lipid pockets"
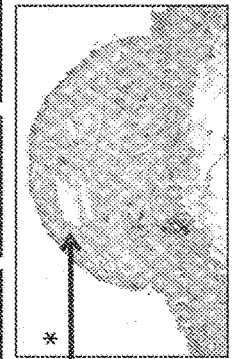
FIG. 31D

TREATING ATHEROSCLEROSIS BY REMOVING SENESCENT FOAM CELL MACROPHAGES FROM ATHEROSCLEROTIC PLAQUES

CROSS-REFERENCE TO RELATED APPLICATIONS

This application is a continuation-in-part of U.S. patent application Ser. No. 15/114,762 (pending), filed Jul. 27, 2016, which is the U.S. National Stage of PCT/US2015/013387, which claims the priority benefit of provisional applications 61/932,704, filed Jan. 28, 2014; 61/932,711, filed Jan. 28, 2014; 61/979,911, filed Apr. 15, 2014; 62/002,709, filed May 23, 2014; 62/042,708, filed Aug. 27, 2014, 62/044,664, filed Sep. 2, 2014; 62/057,820, filed Sep. 30, 2014; 62/057,825, filed Sep. 30, 2014; 62/057,828, filed Sep. 30, 2014; 62/061,627, filed Oct. 8, 2014; and 62/061,629, filed Oct. 8, 2014. This application also claims priority to provisional applications 62/412,223, filed Oct. 24, 2016 and 62/412,605, filed Oct. 25, 2016. The aforelisted applications are all hereby incorporated herein by reference in their entirety for all purposes, including but not limited to the preparation and use of senolytic agents to treat atherosclerosis.

STATEMENT OF FEDERALLY SPONSORED RESEARCH

This invention was made with government support under Grant No. AG009909, AG017242, AG41122 and AG046061 awarded by the National Institutes of Health. The government has certain rights in this invention.

BACKGROUND

Atherosclerosis is a primary risk factor for adverse events resulting from cardiovascular disease, such as strokes and heart attacks. SA-β-GAL positive cells have been identified in established atherosclerotic lesions (plaques). Clearance of these cells reduces plaque growth and promotes plaque stability.

INCORPORATION BY REFERENCE

Aspects of this work were disclosed previously in U.S. patent application Ser. No. 15/114,762, published as US 2016/0339019 A1, of which this application is a continuation-in-part. A related academic publication by B. G. Childs et al. appeared in Science 354(6311):472-477, 2016. These and all other publications, patents, and patent applications mentioned in this specification are herein incorporated by reference in their entirety for all purposes, to the same extent as if each individual publication, patent, or patent application was specifically and individually indicated to be incorporated by reference.

BRIEF DESCRIPTION OF THE DRAWINGS

FIG. 1A-D p16$^{Ink4a}$-positive senescent cells drive formation of atherosclerotic plaques. The left of FIG. 1A shows examples of three types of senescent cells observed by Gal-EM in plaques of Ldlr$^{-/-}$ mice on a HFD for 88 days. Cell outlines are traced in dashed green. Endothelial-like cells are elongated and adjacent to the lumen. VSMC-like cells are elongated spindle shaped cells or irregularly shaped cells ramified cells. Macrophage-like cells are highly vacuolated, circular cells. On the right FIG. 1A shows senescent cell quantification in plaques with and without clearance. FIG. 1B illustrates experimental design for testing the effect of senescent cell clearance on atherogenesis (left), and Sudan IV-stained descending aortas (not including the arch) (right). FIG. 1C illustrates quantification of total descending aorta plaque burden, number, and lesion size. FIG. 1D illustrates analysis by qRT-PCR of senescence markers in aortic arches of indicated genotypes and treatments. Treatment in FIG. 1B and FIG. 1D: 5 mg/kg GCV or PBS daily for 5 days followed by 14 days off on a repeating cycle for 88 days. Scale bars: 2 μm (FIG. 1A) and 500 nm (FIG. 1A, insets). Bar graphs represent mean±SEM. *P<0.05; P<0.01; *, P<0.001 (unpaired two-tailed t-tests with Welch's correction).

FIG. 2A-F Intimal senescent foamy macrophages form during early atherogenesis and foster production of proatherogenic factors. FIG. 2A, Schematic of inner curvature (left) with examples of SA-β-Gal stained 9-day fatty streaks with and without senescent cell clearance and quantification (middle) and measurements of streak size (right). Treatment, 25 mg/kg GCV 1× daily. FIG. 2B, TEM images of Ldlr$^{-/-}$ mice after 9-day HFD feeding showing fatty streak foci with X-Gal-positive foam cell macrophages (artificial coloring articulates cell boundaries in the multilayer). FIG. 2C, Quantification of multilayer foci in day-9 fatty streaks with and without senescent cells. FIG. 2D, Quantification of foam cell macrophages with X-Gal crystal-containing vesicles without and with clearance. FIG. 2E, Left, representative SA-β-Gal stained 12-day fatty streaks without and with GCV treatment for the last 3 days (25 mg/kg GCV 3× daily). Right, quantification of lesion burden. FIG. 2F, qRT-PCR analysis of senescence marker expression in fatty streaks collected from Ldlr$^{-/-}$ and Ldlr$^{-/-}$;3MR mice on a 12-day HFD and treated with GCV for the last 3 days. Scale bars: 1 mm (FIG. 2A, FIG. 2E); 2 μm (FIG. 2B) and 500 nm (FIG. 2B, insets) Bar graphs represent mean±SEM. *P<0.05; P<0.01; *P<0.001 (unpaired two tailed t-tests with Welch's correction).

FIG. 3A-D Removal of p16$^{Ink4a+}$ cells in established plaques perturbs the proatherogenic microenvironment. FIG. 3A, Left, experimental design for testing the effect of senescent cell clearance on established plaques. Middle, Sudan W-stained descending aortas (not including the arch). Right, quantification of Sudan IV$^+$ areas and plaque number. FIG. 3B, Left, experimental design for LFD switching. Middle, Sudan IV-stained descending aortas (not including the arch). Right, quantification of Sudan IV$^+$ and abnormal intimal areas. FIG. 3C, SA-β-Gal staining of whole aortas (experimental design as in FIG. 3B). Insets correlate to color-matched boxes on low-power view. FIG. 3D, qRT-PCR for senescence markers in aortic arches from indicated cohorts. Aortic arches from Ldlr$^{-/-}$;3MR females fed LFD until 258 days of age and treated with Veh for the last 100 days were used to assess baseline expression levels. Treatments in FIGS. 3A-D, 5 mg/kg GCV (or Veh) daily for 5 days followed by 14 days off on a repeating cycle for 100 days. Bar graphs represent mean±SEM. *P<0.05; P<0.01; *P<0.001 (FIG. 3A and FIG. 3B, ANOVA with Sidak's post-hoc correction for familywise error; FIG. 3D, unpaired two-tailed t-test with Welch's correction).

FIG. 4A-C Senescent cells promote plaque instability by elevating metalloprotease production. FIG. 4A, Representative sections from descending aorta plaques of mice with the indicated genotypes, treatments, diets and histological stainings. Red dashed lines trace the fibrous cap and red arrowheads indicated ruptured aortic elastic fibers. FIG. 4B, Quantification of fibrous cap thickness in plaques from FIG. 4A. FIG. 4C: top, experimental overview, bottom, qRT-PCR analysis of senescence markers in GFP⁺ and GFP⁻ cells. Bar graphs represent mean±SEM. *P<0.05; P<0.01; *P<0.001 (FIG. 4B, ANOVA with Sidak's post-hoc correction for familywise error; FIG. 4C, unpaired two-tailed t-test with Welch's correction).

FIG. 5A-C Senescent cells accumulate in atherosclerotic plaques and are cleared by p16-3MR. FIG. 5A, Scheme of plaque induction protocol as well as schematic of heart and aorta alongside SA-β-Gal-stained aortas. LV, left ventricle; BCA, brachiocephalic artery. Inset corresponds to boxed region on low-power view. FIG. 5B, Senescence marker expression in aortic arches from $Ldlr^{-/-}$ mice fed a HFD for 88 days versus LFD-fed controls. C, SA-β-Gal-stained descending aorta plaques from $Ldlr^{-/-}$ and $Ldlr^{-/-}$;3MR mice fed HFD for 88 days, followed by 5 weeks of LFD and GCV treatment. Scale bars: 100 μm (FIG. 5A, inset) and 500 μm (FIG. 5C) Bar graphs represent mean±SEM. *, P<0.05; P<0.01; *P<0.001 (unpaired t-test with Welch's correction).

FIG. 6A-E Senescent cell clearance is athero-protective in the brachiocephalic artery. FIG. 6A, Representative sections of plaque in brachiocephalic arteries. Plaque is traced with red dashed lines which, for clarity, extend through the vascular wall although plaque is only measured above the most superficial elastic fiber. Arrowheads in insets indicate broken elastic fibers. FIG. 6B, Quantification of average cross-sectional area of plaque in brachiocephalic arteries. FIG. 6C, Quantification of fragmented aortic elastic fibers from brachiocephalic plaques in FIG. 6A. FIG. 6D, SA-β-Gal staining of whole aortas undergoing senescent cell clearance compared to controls. Scale bars, 100 μm (FIG. 6A) and 20 μm (FIG. 6A, insets). Bar graphs represent mean+SEM. *, P<0.05; P<0.01; *P<0.001 (unpaired t-test with Welch's correction). FIG. 6E, Senescence marker expression in aortic arches from $Ldlr^{-/-}$ mice fed a HFD and an HFD+GCV.versus LFD-fed controls.

FIG. 7A-I Parameters that modulate atherosclerosis are not impacted by $16^{Ink4a+}$ cell killing or GCV. FIG. 7A, Total body weight of mice with indicated diets, treatments, and genotypes enrolled in constitutive $p16^{Ink4a+}$ cell clearance study. FIG. 7B, Body fat percentage measured by MRI. FIG. 7C, Mesentric fat mass measurements. FIG. 7D, Inguinal white adipose tissue (iWAT) mass measurements. FIGS. 7E-H. Circulating cell counts for eosinophils (FIG. 7E), lymphocytes (FIG. 7F), monocytes (FIG. 7G), and platelets (FIG. 7H) as measured by Hemavet blood analyzer. FIG. 7I, Plasma lipid profile. Bar graphs represent mean+SEM. *P<0.05; P<0.01; *P<0.001 (ANOVA with Sidak's post-hoc correction for familywise error).

FIG. 8A-B INK_ATTAC-mediated senescent cell killing blunts atherogenesis. A, sudan IV-stained descending aortas of the indicated mice. Experimental design: $Ldlr^{-/-}$ female with or without the INK-ATTAC transgene were fed a LFD between 21 and 70 days of age and then switched to a HFD until aortas were dissected and analyzed at 172 days of age. AP20187 (AP) treatment (twice weekly) was started when animals were switched to a HFD. FIG. 8B, Quantification of Sudan IV⁺ area, plaque number, and individual plaque size in mice from FIG. 8A. Bar graphs represent mean+SEM. *P<0.05 (unpaired two-tailed t-tests with Welch's correction).

FIG. 9A-C Senescent cell killing by INK-NTR attenuates plaque initiation and growth. FIG. 9A, Schematic of the INK-NTR transgene. FIG. 9B, Experimental design and Sudan IV-stained whole aortas. $Ldlr^{-/-}$ females with or without the INK-NTR transgene were fed a LFD between 21 and 70 days of age and then switched to a HFD and given ad libitum access to drinking water containing metronidazole until aortas were dissected and analyzed at 158 days of age. FIG. 9C, Quantification of total Sudan IV⁺ area, plaque number, and individual plaque size in mice from FIG. 9B. Bar graphs represent mean+SEM. *P<0.05 (unpaired two-tailed t-tests with Welch's correction).

FIG. 10A-B ABT263-mediated senescent cell clearance inhibits atherogenesis. FIG. 10A, Experimental design and representative Sudan-IV-stained descending aortas from $Ldlr^{-/-}$ mice fed a HFD for 88 days and treated with either vehicle or ABT263. FIG. 10B, Total plaque burden, plaque number, and individual plaque size in mice from FIG. 10A. Bar graphs represent mean+SEM. *, P<0.05; ***P<0.001 (unpaired t-test with Welch's correction).

FIG. 11A-D Transgenic and pharmacological elimination of senescent cells inhibits fatty streak formation. FIG. 11A, qRT-PCR analysis of senescence markers, monocyte chemotactic factors, cytokines, and proteases in the inner curvature of the aortic arch of $Ldlr^{-/-}$ mice fed LFD or HFD for 9 days. FIG. 11B, Left, SA-β-Gal stained fatty streaks from $Ldlr^{-/-}$ mice fed a HFD for 9 days with either vehicle or ABT263 treatment. Right, quantification of fatty streak burden in the aortic arch. FIG. 11C, Quantification of percentage of X-Gal-positive foam cell macrophages in inner curvatures from $Ldlr^{-/-}$ or $Ldlr^{-/-}$;3MR mice with 9-day fatty streaks treated with GCV for 3 days. FIG. 11D, Representative TEM images of plaques from $Ldlr^{-/-}$ or $Ldlr^{-/-}$;3MR mice with 9-day fatty streaks treated with GCV for 3 days. Basement membrane is traced in dashed white line for clarity, and subendothelial contents are false-colored in red. In the $Ldlr^{-/-}$ panel, individual macrophage foam cells are different shades of red. In the $Ldlr^{-/-}$;3MR, insets demonstrate the diffuse acellular debris retained in the subendothelium following three days of senescent cell killing. Scale bars: 1 mm (FIG. 11B), 2 μm (FIG. 11D), 500 nm and (FIG. 11D, inset). Bar graphs represent mean±SEM. *, P<0.05; ***P<0.001 (unpaired t-test with Welch's correction).

FIG. 12A-C Senescent cell killing in advanced plaques reduces monocyte chemotactic factors without impacting plasma lipids. FIG. 12A, Lipid profile from mice fed a LFD or HFD for the indicated durations, genotypes, and drug treatments. FIG. 12B, qRT-PCR analysis of CD11b expression in aortic arches with advanced plaques from FIG. 12A. FIG. 12C, qRT-PCR analysis of monocyte chemotactic factors in aortic arches with advanced plaques, with and without senescent cell clearance. Bar graphs represent mean±SEM. *P<0.05; P<0.01; *P<0.001 (ANOVA with Sidak's post-hoc correction for familywise error).

FIG. 13A-B Senescent cells reduce collagen and elastin content in advanced plaques. FIG. 13A, Quantification of collagen (blue colored regions) in paraffin sections of advanced plaques stained with Masson's trichrome. FIG. 13B, Quantification of aortic elastic fibers underlying the plaque neointima with one or more interruptions.

FIG. 14A-C Senescent cell clearance increases fibrous cap thickness and collagen content in brachiocephalic artery plaques. FIG. 14A, Representative images of brachiocephalic artery plaques. A, Representative images of brachiocephalic artery plaques from $Ldlr^{-/-}$ or $Ldlr^{-/-}$;3MR mice given the indicated diets or treatments and stained with Masson's trichrome (top) or HE (bottom). FIG. 14B, Quantification of fibrous cap thickness from mice in FIG. 14A. FIG. 14C, Quantification of blue-stained collagen in advanced plaques from A visualized using Masson's trichrome. Bar graphs represent mean±SEM. *, P<0.05 (unpaired t-test with Welch's correction).

FIG. 15A-H Established plaques are stabilized by short-term senescent cell removal. FIG. 15A, Schematic showing the design of the short-term senescent cell killing experiment. FIG. 15B, Examples of fibrous caps (indicated between red dashed lines) from plaques undergoing high-intensity clearance. FIG. 15C-E, Quantification of fibrous cap thickness (FIG. 15C), VSMC-like cell density (FIG. 15D), and macrophage-like cell density (FIG. 15E) in plaques. FIG. 15F, Calculation of the VSMC- to macrophage-like cell ratio in plaques. FIG. 15G, Representative image of a monocyte bound to endothelium adjacent to a plaque. FIG. 15H, Quantification of adherent monocytes in plaque sections from FIG. 15B. Scale bar, 10 μm (FIG. 15B) and 2 μm (FIG. 15G). Bar graphs represent mean±SEM. *P<0.05 (unpaired two-tailed t-tests with Welch's correction).

FIG. 17A illustrates effect of Nutlin-3a at 0, 2.5 or 10 μM after 9 days of treatment (D9) on irradiated (IR) senescent foreskin fibroblasts (Sen(IR)HCA2). FIG. 17B shows percent survival of irradiated BJ cells (Sen(IR)BJ) treated with Nutlin 3a at the concentrations shown. FIG. 17C shows percent survival of irradiated lung fibroblasts (Sen(IR)IMR90)), and FIG. 17D shows percent survival of irradiated mouse embryonic fibroblasts (MEFs) treated with Nutlin-3a.

FIG. 18A shows the effect of Nutlin-3a on doxorubicin-treated (Doxo) senescent foreskin fibroblasts (HCA2). FIG. 18B illustrates the effect of Nutlin-3a on doxorubicin treated (Doxo) senescent aortic endothelial cells (Endo Aort) (FIG. 18B).

FIGS. 19A-C show percent growth of non-senescent fibroblasts treated with Nutlin-3a. Cells were treated with Nutlin-3a for 9 days and percent growth determined (D9). Nutlin-3a was non-toxic to non-senescent foreskin fibroblasts (Non Sen HCA2) as shown in FIG. 19A, non-toxic to non-senescent lung fibroblasts (Non Sen IMR90) as shown in FIG. 19B, and non-toxic to non-senescent lung mouse embryonic fibroblasts (Non Sen MEFs) as shown in FIG. 19C.

FIG. 20A and FIG. 20B show that Nutlin-3a is non-toxic to non-senescent aortic endothelial (Non Sen Endo Aort) cells and to non-senescent pre-adipocytes (Non Sen Pread), respectively.

FIGS. 21A-B illustrate schematics of two atherosclerosis animal model studies in LDLR$^{-/-}$ transgenic mice fed a high fat diet (HFD). The study illustrated in FIG. 21A assesses the extent to which clearance of senescent cells from plaques in LDLR−/− mice with a senolytic agent (e.g., Nutlin-3A) reduces plaque load. The study illustrated in FIG. 21B assesses the extent to which ganciclovir-based clearance of senescent cells from LDLR−/−/3MR double transgenic mice improves pre-existing atherogenic disease.

FIGS. 22A-D depict graphs of the plasma lipid levels in LDLR−/− mice fed a HFD after one treatment cycle of Nutlin-3A or vehicle. FIG. 22A shows total cholesterol levels in vehicle or Nutlin-3A treated LDLR−/− mice compared to LDLR−/− fed a non-HFD. FIG. 22B shows HDL levels in vehicle or Nutlin-3A treated LDLR−/− mice compared to LDLR−/− fed a non-HFD. FIG. 22C shows triglyceride levels in vehicle or Nutlin-3A treated LDLR−/− mice compared to LDLR−/− fed a non-HFD. FIG. 22D shows vLDL/LDL/IDL levels in vehicle or Nutlin-3A treated LDLR−/− mice compared to LDLR−/− fed a non-HFD.

FIG. 23A illustrates the aortic arch (boxed). FIGS. 23B-C show expression levels of SASP factors and senescence markers, normalized to GAPDH and expressed as fold change vs. non-HFD, vehicle-treated, age-matched LDLR−/− mice. FIG. 23D shows the data from FIGS. 45B-C in numerical form.

FIGS. 24A-C illustrate RT-PCR analysis of SASP factors and senescence markers in aortic arches of LDLR−/− mice fed a HFD after two treatment cycles of Nutlin-3A or vehicle. FIGS. 24A-B expression levels of SASP factors and senescence markers, normalized to GAPDH and expressed as fold change vs. non-HFD, vehicle-treated, age-matched LDLR−/− mice. FIG. 24C shows the data from FIGS. 24A-B in numerical form.

FIGS. 25A-C illustrate staining analysis for aortic plaques in LDLR−/− mice fed a HFD after three treatment cycles of Nutlin-3A or vehicle. FIG. 25A illustrates the aorta. FIG. 25B shows the % of the aorta covered in plaques. FIG. 25C shows Sudan IV staining of the aorta to visualize the plaques and the area covered by the lipid plaque was expressed as a percentage of the total surface area of the aorta in each sample.

FIGS. 30A-B show Sudan IV staining of the aorta to visualize the plaques in LDLR−/− control mice and LDLR−/−/3MR mice, respectively. FIG. 30C shows the % of the aorta covered in plaques as measured by area of Sudan IV staining.

FIGS. 31A-D illustrate plaque morphology analysis in LDLR−/−/3MR double transgenic mice and LDLR−/− control mice fed a HFD after a 100 day treatment period with ganciclovir. FIGS. 31A and C show Sudan IV staining of the aorta to visualize the plaques in LDLR−/− control mice and LDLR−/−/3MR mice, respectively. Plaques that are circled were harvested and cut into cross-sections and stained with to characterize the general architecture of the atherosclerotic plaques (FIGS. 31B and D). "#" marks fat located on the outside of the aorta.

DETAILED DESCRIPTION OF THE INVENTION

Figure 1A:
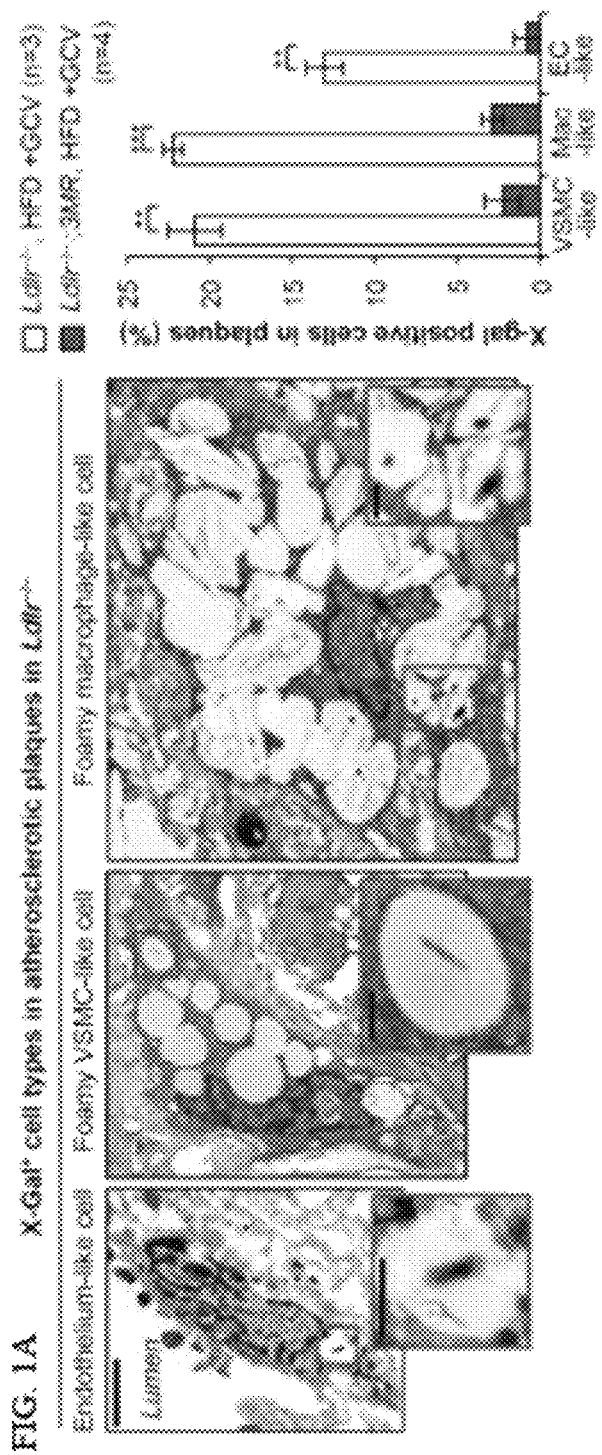

This disclosure provides methods and materials for treating senescence-associated cardiovascular disease that is associated with or caused by arteriosclerosis (i.e., hardening of the arteries).

Atherosclerosis is characterized by patchy intimal plaques (atheromas) that encroach on the lumen of medium-sized and large arteries; the plaques contain lipids, inflammatory cells, smooth muscle cells, and connective tissue. Atherosclerosis can affect large and medium-sized arteries, including the coronary, carotid, and cerebral arteries, the aorta and its branches, and major arteries of the extremities. Atherosclerosis is characterized by patchy intimal plaques (atheromas) that encroach on the lumen of medium-sized and large arteries; the plaques contain lipids, inflammatory cells, smooth muscle cells, and connective tissue.

Methods are provided for inhibiting the formation of atherosclerotic plaques (or reducing, diminishing, causing decrease in formation of atherosclerotic plaques) by administering a senolytic agent. In other embodiments, methods are provided for reducing (decreasing, diminishing) the amount (i.e., level) of plaque. Reduction in the amount of plaque in a blood vessel (e.g., artery) may be determined, for example, by a decrease in surface area of the plaque, or by a decrease in the extent or degree (e.g., percent) of occlusion of a blood vessel (e.g., artery), which can be determined by angiography or other visualizing methods used in the cardiovascular art. Also provided herein are methods for increasing the stability (or improving, promoting, enhancing stability) of atherosclerotic plaques that are present in one or more blood vessels (e.g., one or more arteries) of a subject, which methods comprise administering to the subject any one of the senolytic agents described herein.

Atherosclerosis is often referred to as a "hardening" or furring of the arteries and is caused by the formation of multiple atheromatous plaques within the arteries. Atherosclerosis (also called arteriosclerotic vascular disease or ASVD herein and in the art) is a form of arteriosclerosis in which an artery wall thickens. Symptoms develop when growth or rupture of the plaque reduces or obstructs blood flow; and the symptoms may vary depending on which artery is affected. Atherosclerotic plaques may be stable or unstable. Stable plaques regress, remain static, or grow slowly, sometimes over several decades, until they may cause stenosis or occlusion. Unstable plaques are vulnerable to spontaneous erosion, fissure, or rupture, causing acute thrombosis, occlusion, and infarction long before they cause hemodynamically significant stenosis. Most clinical events result from unstable plaques, which do not appear severe on angiography; thus, plaque stabilization may be a way to reduce morbidity and mortality. Plaque rupture or erosion can lead to major cardiovascular events such as acute coronary syndrome and stroke (see, e.g., Du et al., BMC Cardiovascular Disorders 14:83 (2014); Grimm et al., Journal of Cardiovascular Magnetic Resonance 14:80 (2012)). Disrupted plaques were found to have a greater content of lipid, macrophages, and had a thinner fibrous cap than intact plaques (see, e.g., Felton et al., Arteriosclerosis, Thrombosis, and Vascular Biology 17:1337-45 (1997)).

Atherosclerosis is a syndrome affecting arterial blood vessels due in significant part to a chronic inflammatory response of white blood cells in the walls of arteries. This is promoted by low-density lipoproteins (LDL, plasma proteins that carry cholesterol and triglycerides) in the absence of adequate removal of fats and cholesterol from macrophages by functional high-density lipoproteins (HDL). The earliest visible lesion of atherosclerosis is the "fatty streak," which is an accumulation of lipid-laden foam cells in the intimal layer of the artery. The hallmark of atherosclerosis is atherosclerotic plaque, which is an evolution of the fatty streak and has three major components: lipids (e.g., cholesterol and triglycerides); inflammatory cells and smooth muscle cells; and a connective tissue matrix that may contain thrombi in various stages of organization and calcium deposits.

Within the outer-most and oldest plaque, calcium and other crystallized components (e.g., microcalcification) from dead cells can be found. Microcalcification and properties related thereto are also thought to contribute to plaque instability by increasing plaque stress (see, e.g., Bluestein et al., J. Biomech. 41(5):1111-18 (2008); Cilla et al., Journal of Engineering in Medicine 227:588-99 (2013)). Fatty streaks reduce the elasticity of the artery walls, but may not affect blood flow for years because the artery muscular wall accommodates by enlarging at the locations of plaque. Lipid-rich atheromas are at increased risk for plaque rupture and thrombosis (see, e.g., Felton et al., supra; Fuster et al., J. Am. Coll. Cardiol. 46:1209-18 (2005)). Reports have found that of all plaque components, the lipid core exhibits the highest thrombogenic activity (see, e.g., Fernandez-Ortiz et al., J. Am. Coll. Cardiol. 23:1562-69 (1994)). Within major arteries in advanced disease, the wall stiffening may also eventually increase pulse pressure.

A vulnerable plaque that may lead to a thrombotic event (stroke or MI) and is sometimes described as a large, soft lipid pool covered by a thin fibrous cap (see, e.g., Li et al., Stroke 37:1195-99 (2006); Trivedi et al., Neuroradiology 46:738-43 (2004)). An advanced characteristic feature of advance atherosclerotic plaque is irregular thickening of the arterial intima by inflammatory cells, extracellular lipid (atheroma) and fibrous tissue (sclerosis) (see, e.g., Newby et al., Cardiovasc. Res. 345-60 (1999)). Fibrous cap formation is believe to occur from the migration and proliferation of vascular smooth muscle cells and from matrix deposition (see, e.g., Ross, Nature 362:801-809 (1993); Sullivan et al., J. Angiology at dx.doi.org/10.1155/2013/592815 (2013)). A thin fibrous cap contributes instability of the plaque and to increased risk for rupture (see, e.g., Li et al., supra).

Both pro-inflammatory macrophages (M1) and anti-inflammatory macrophages (M2) can be found in arteriosclerotic plaque. The contribution of both types to plaque instability is a subject of active investigation, with results suggesting that an increased level of the M1 type versus the M2 type correlates with increased instability of plaque (see, e.g., Medbury et al., Int. Angiol. 32:74-84 (2013); Lee et al., Am. J. Clin. Pathol. 139:317-22 (2013); Martinet et al., Cir. Res. 751-53 (2007)).

Generally, diagnosis of atherosclerosis and other cardiovascular disease is based on symptoms (e.g., chest pain or pressure (angina), numbness or weakness in arms or legs, difficulty speaking or slurred speech, drooping muscles in face, leg pain, high blood pressure, kidney failure and/or erectile dysfunction), medical history, and/or physical examination of a patient. Diagnosis may be confirmed by angiography, ultrasonography, or other imaging tests. Subjects at risk of developing cardiovascular disease include those having any one or more of predisposing factors, such as a family history of cardiovascular disease and those having other risk factors (i.e., predisposing factors) such as high blood pressure, dyslipidemia, high cholesterol, diabetes, obesity and cigarette smoking, sedentary lifestyle, and hypertension. In a certain embodiment, the cardiovascular disease that is a senescence cell associated disease/disorder is atherosclerosis.

The methods of the invention include administering to a subject in need thereof a therapeutically-effective amount of a small molecule senolytic agent that selectively kills senescent cells over non-senescent cells; wherein the senescence-associated disease or disorder is not a cancer, wherein the senolytic agent is administered in at least two treatment cycles, wherein each treatment cycle independently comprises a treatment course of from 1 day to 3 months followed by a non-treatment interval of at least 2 weeks; provided that if the senolytic agent is an MDM2 inhibitor, the MDM2 inhibitor is administered as a monotherapy, and each treatment course is at least 5 days long during which the MDM2 inhibitor is administered on at least 5 days. In certain embodiments, the senolytic agent is selected from an MDM2 inhibitor; an inhibitor of one or more Bcl-2 anti-apoptotic protein family members wherein the inhibitor inhibits at least Bcl-xL; and an Akt specific inhibitor. In a specific embodiment, the MDM2 inhibitor is a cis-imidazoline compound, a spiro-oxindole compound, or a benzodiazepine compound. In a specific embodiment, the cis-imidazoline compound is a nutlin compound. In a specific embodiment, the senolytic agent is an MDM2 inhibitor and is Nutlin-3a or RG-1172. In a specific embodiment, the nutlin compound is Nutlin-3a.

In a specific embodiment, the cis-imidazoline compound is RG-7112, RG7388, RO5503781, or is a dihydroimidazothiazole compound. In a specific embodiment, the dihydroimidazothiazole compound is DS-3032b. In a specific embodiment, the MDM2 inhibitor is a spiro-oxindole compound selected from MI-63, MI-126, MI-122, MI-142, MI-147, MI-18, MI-219, MI-220, MI-221, MI-773, and 3-(4-chlorophenyl)-3-((1-(hydroxymethyl)cyclopropyl)methoxy)-2-(4-nitrobenzyl)isoindolin-1-one. In a specific embodiment, the MDM2 inhibitor is Serdemetan; a piperidinone compound; CGM097; or an MDM2 inhibitor that also inhibits MDMX and which is selected from RO-2443 and RO-5963.

In a specific embodiment, the piperidinone compound is AM-8553. In a specific embodiment, the inhibitor of one or more Bcl-2 anti-apoptotic protein family members is a Bcl-2/Bcl-xL inhibitor; a Bcl-2/Bcl-xL/Bcl-w inhibitor; or a Bcl-xL selective inhibitor. In a specific embodiment, the senolytic agent is an inhibitor of one or more Bcl-2 anti-apoptotic protein family members wherein the inhibitor inhibits at least Bcl-xL and is selected from ABT-263, ABT-737, WEHI-539, and A-1155463. In a specific embodiment, the Bcl-xL selective inhibitor is a benzothiazole-hydrazone compound, an aminopyridine compound, a benzimidazole compound, a tetrahydroquinolin compound, or a phenoxyl compound. In a specific embodiment, the benzothiazole-hydrazone compound is a WEHI-539. In a specific embodiment, the inhibitor of the one or more Bcl-2 anti-apoptotic protein family members is A-1155463, ABT-263, or ABT-737. In a specific embodiment, the Akt inhibitor is MK-2206.

A pharmaceutical composition may be delivered to a subject in need thereof by any one of several routes known to a person skilled in the art. By way of non-limiting example, the composition may be delivered orally, intravenously, intraperitoneally, by infusion (e.g., a bolus infusion), subcutaneously, enteral, rectal, intranasal, by inhalation, buccal, sublingual, intramuscular, transdermal, intradermal, topically, intraocular, vaginal, rectal, or by intracranial injection, or any combination thereof. In certain particular embodiments, administration of a dose, as described above, is via intravenous, intraperitoneal, directly into the target tissue or organ, or subcutaneous route. In certain embodiments, a delivery method includes drug-coated or permeated stents for which the drug is the senolytic agent. Formulations suitable for such delivery methods are described in greater detail herein.

A senolytic agent (which may be combined with at least one pharmaceutically acceptable excipient to form a pharmaceutical composition) can be administered directly to the target tissue or organ comprising senescent cells that contribute to manifestation of the disease or disorder. Methods are provided herein for treating a cardiovascular disease or disorder associated with arteriosclerosis, such as atherosclerosis by administering directly into an artery. In another particular embodiment, a senolytic agent (which may be combined with at least one pharmaceutically acceptable excipient to form a pharmaceutical composition) for treating a senescent-associated pulmonary disease or disorder may be administered by inhalation, intranasally, by intubation, or intracheally, for example, to provide the senolytic agent more directly to the affected pulmonary tissue. By way of another non-limiting example, the senolytic agent (or pharmaceutical composition comprising the senolytic agent) may be delivered directly to the eye either by injection (e.g., intraocular or intravitreal) or by conjunctival application underneath an eyelid of a cream, ointment, gel, or eye drops. In more particular embodiments, the senolytic agent or pharmaceutical composition comprising the senolytic agent may be formulated as a timed release (also called sustained release, controlled release) composition or may be administered as a bolus infusion.

A pharmaceutical composition (e.g., for oral administration or for injection, infusion, subcutaneous delivery, intramuscular delivery, intraperitoneal delivery or other method) may be in the form of a liquid. A liquid pharmaceutical composition may include, for example, one or more of the following: a sterile diluent such as water, saline solution, preferably physiological saline, Ringer's solution, isotonic sodium chloride, fixed oils that may serve as the solvent or suspending medium, polyethylene glycols, glycerin, propylene glycol or other solvents; antibacterial agents; antioxidants; chelating agents; buffers and agents for the adjustment of tonicity such as sodium chloride or dextrose. A parenteral composition can be enclosed in ampoules, disposable syringes or multiple dose vials made of glass or plastic. The use of physiological saline is preferred, and an injectable pharmaceutical composition is preferably sterile. In another embodiment, for treatment of an ophthalmological condition or disease, a liquid pharmaceutical composition may be applied to the eye in the form of eye drops. A liquid pharmaceutical composition may be delivered orally.

In certain embodiments of a method described herein for treating a cardiovascular disease associated with or caused by arteriosclerosis, one or more senolytic agents may be delivered directly into a blood vessel (e.g., an artery) via a stent. In a particular embodiment, a stent is used for delivering a senolytic agent to an atherosclerotic blood vessel (an artery). A stent is typically a tubular metallic device, which has thin-metal screen-like scaffold, and which is inserted in a compressed form and then expanded at the target site. Stents are intended to provide long-term support for the expanded vessel. Several methods are described in the art for preparing drug-coated and drug-embedded stents. For example, a senolytic agent may be incorporated into polymeric layers applied to a stent. A single type of polymer may be used, and one or more layers of the senolytic agent permeated polymer may be applied to a bare metal stent to form the senolytic agent-coated stent. The senolytic agent may also be incorporated into pores in the metal stent itself, which may also be referred to herein as a senolytic agent-permeated stent or senolytic agent-embedded stent.

A senolytic agent may be formulated within liposomes and applied to a stent; in other particular embodiments, for example, when the senolytic agent is ABT-263, the ABT-263 is not formulated in liposome. Placement of stents in an atherosclerotic artery is performed by a person skilled in the medical art. A senolytic agent-coated or -embedded stent not only expands the affected blood vessel (e.g., an artery) but also may be effective for one or more of (1) reducing the amount of plaque, (2) inhibiting formation of plaque, and (3) increasing stability of plaque (e.g., by decreasing lipid content of the plaque; and/or causing an increase in fibrous cap thickness), particularly with respect to plaque proximal to the agent coated or agent embedded stent.

Kits with unit doses of one or more of the agents described herein, usually in oral or injectable doses, are provided. Such kits may include a container containing the unit dose, an informational package insert describing the use and attendant benefits of the drugs in treating the senescent cell associated disease, and optionally an appliance or device for delivery of the composition.

Empirical Observations that Support this Invention

Using low-density lipoprotein knockout (LDLr−/−) mice on a high-fat diet as a model for human atherosclerosis, it is seen that that senescent foamy macrophages populate the subendothelial space within days after induction of hypercholesterolemia (FIG. 2A and FIG. 2B). Clearance of senescent cells from early stage lesions using genetic (p16-3MR+ ganciclovir; FIGS. 2C-E) or pharmacological (ABT263; FIG. 11B) approaches, resulted in near complete lesion regression (FIG. 11D).

Mechanistically, senescent cells in early lesions are the main drivers of VMAC1 and MCP1 expression, two key monocyte recruitment factors that drive plaque growth by escalating foamy macrophage accumulation in the subendothelial space (FIG. 2F). Purification of senescent cells from atherogenic plaques reveals that senescent cells express both VCAM1 and MCP1, the latter in high abundance (FIG. 4C).

Thus, the elimination of senescent cells inhibits the growth of atherogenic lesions by blunting recruitment of circulating monocytes.

Additionally, senescent cells from mature plaques produce high levels of two matrix metalloproteinases, MMP12 and MMP13, that digest the fibrous cap that provides mature plaques with stability, thereby preventing plaque rupture, a major determining factor in the catastrophic consequences of atherosclerotic diseases, such as acute heart attacks and strokes (FIG. 4C). These findings explain why clearance of senescent cells from advanced plaques preserves plaque stability (fibrous cap thickness and elastic fiber integrity) (FIG. 4A, 4B).

$p16^{Ink4a}$-positive senescent foam cells accumulate throughout atherogenesis, where they are causally implicated in the formation of fatty streaks and their progression to large, vulnerable plaques by enhancing monocyte recruitment factors, inflammation, and matrix metalloprotease production. Atherosclerosis initiates when oxidized lipoprotein infiltrates the subendothelial space of arteries, often due to aberrantly elevated levels of apolipoprotein B-containing lipoproteins in the blood (1). Chemotactic signals arising from activated endothelium and vascular smooth muscle attract circulating monocytes that develop into lipid-loaded foamy macrophages, a subset of which adopt a proinflammatory phenotype through a mechanism that is not fully understood (2). The proinflammatory signals lead to additional rounds of monocyte recruitment and accumulation of other inflammatory cells including T and B cells, dendritic cells and mast cells, allowing initial lesions, often termed fatty streaks, to increase in size and develop into plaques (3). Plaque stability, rather than absolute size determines whether atherosclerosis is clinically silent or pathogenic because unstable plaques can rupture and produce vessel-occluding thrombosis and end-organ damage (4). Stable plaques have a relatively thick fibrous cap consisting largely of vascular smooth muscle cells (VSMCs) and extracellular matrix components, partitioning soluble clotting factors in the blood from thrombogenic molecules in the plaque (5). In advanced disease, plaques destabilize when elevated local matrix metalloprotease production degrades the fibrous cap, increasing the risk of lesion rupture and subsequent thrombosis.

Advanced plaques contain cells with markers of senescence, a stress response that entails a permanent growth arrest coupled to the robust secretion of numerous biologically active molecules, referred to as the senescence-associated secretory phenotype (SASP). The senescence markers include elevated senescence-associated β-galactosidase (SA-β Gal) activity and $p16^{Ink4a}$, p53 and p21 expression (6, 7). Human plaques contain cells with shortened telomeres, which predisposes cells to undergo senescence (10). Consistent with a proatherogenic role of senescence is the observation that expression of a loss-of-function telomere binding protein (Trf2) in VSMCs accelerates plaque growth in the $ApoE^{-/-}$ mouse model of atherosclerosis, although evidence for increased in vivo senescence was not provided (10). On the other hand, mice lacking core components of senescence pathways, such as p53, p21 or $p19^{Arf}$ (9, 11-13), show accelerated atherosclerosis, implying a protective role for senescence. Studies showing that human and mouse polymorphisms that reduce expression of $p16^{Ink4a}$ and p14/$19^{Arf}$ correlate with increased atheroma risk support this conclusion (9, 14, 15).

In the development of this invention, the role of naturally occurring senescent cells at different stages of atherogenesis was examined using genetic and pharmacological methods of eliminating such cells.

First, it was verified that senescent cells accumulate in Ldl-receptor knockout ($Ldlr^{-/-}$) mice, a model of atherogenesis. To this end, 10-week-old Ldlr$^{-/-}$ mice were fed a high-fat diet (HFD) for 88 days. Indeed, SA-β-Gal staining occurred in atherosclerotic lesions but not in the normal adjacent vasculature or aortas of low-fat diet (LFD)-fed Ldlr$^{-/-}$ mice (FIG. 5A). In addition, plaque-rich aortic arches had elevated transcript levels of p16$^{Ink4a}$, p19$^{Arf}$ and various canonical SASP components, including the matrix metalloproteases Mmp$^3$ and Mmp$^{13}$ and the inflammatory cytokines Il1α and Tnfα (FIG. 5B). To eliminate senescent cells from plaques p16-3MR mice (16) were used, a transgenic model that expresses the herpes simplex virus thymidine kinase (HSV-TK) under the control of the Cdkn2a promoter and kills p16$^{Ink4a}$-positive senescent cells upon administration of ganciclovir (GCV). Plaques of Ldlr$^{-/-}$; 3MR mice fed a HFD for 88 days and then treated short term with GCV had low SA-β-Gal activity compared to those of Ldlr$^{-/-}$ mice (FIG. 5C), indicating efficient clearance of senescent cells. Examination of the plaques by transmission electron microscopy (TEM) revealed that three morphologically distinct cell types produced X-Gal crystals: elongated, vacuolated cells located in the endothelial layer, spindly foam cells with histological properties of VSMCs, and large foamy cells resembling lipid-loaded macrophages (FIG. 1A). These cells were referred to as endothelial-, foamy VSMC- and foamy macrophage-like cells, respectively, because cells polymorphisms that reduce expression of p16$^{Ink4a}$ and p14/19$^{Arf}$ correlate with increased atheroma risk support this conclusion (9, 14, 15).

The role of naturally occurring senescent cells at different stages of atherogenesis was examined using genetic and pharmacological methods of eliminating senescent cells. First, it was verified that senescent cells accumulate in Ldl-receptor knockout (Ldlr$^{-/-}$) mice, a model of atherogenesis. To this end, 10-week-old Ldlr$^{-/-}$ mice were fed a high-fat diet (HFD) for 88 days. Indeed, SA-β-Gal staining occurred in atherosclerotic lesions but not in the normal adjacent vasculature or aortas of low-fat diet (LFD)-fed Ldlr$^{-/-}$ mice (FIG. 5A). In addition, plaque-rich aortic arches had elevated transcript levels of p16$^{Ink4a}$, p19$^{Arf}$ and various canonical SASP components, including the matrix metalloproteases Mmp3 and Mmp13 and the inflammatory cytokines Il1α and Tnfα (FIG. 5B). To eliminate senescent cells from plaques p16-3MR mice (16) were used, which is a transgenic model that expresses the herpes simplex virus thymidine kinase (HSV-TK) under the control of the Cdkn2a promoter and kills p16$^{Ink4a}$-positive senescent cells upon administration of ganciclovir (GCV). Plaques of Ldlr$^{-/-}$; 3MR mice fed a HFD for 88 days and then treated short term with GCV had low SA-β-Gal activity compared to those of Ldlr$^{-/-}$ mice (FIG. 5C), indicating efficient clearance of senescent cells. Examination of the plaques by transmission electron microscopy (TEM) revealed that three morphologically distinct cell types produced X-Gal crystals: elongated, vacuolated cells located in the endothelial layer, spindly foam cells with histological properties of VSMCs, and large foamy cells resembling lipid-loaded macrophages (FIG. 1A). These cells were referred to as endothelial-, foamy VSMC- and foamy macrophage-like cells, respectively, because cells within plaques change shape and lineage markers, precluding accurate assessment of cell origin (2). All three senescent cell types were efficiently eliminated by GCV (FIG. 1A).

Figure 1D:
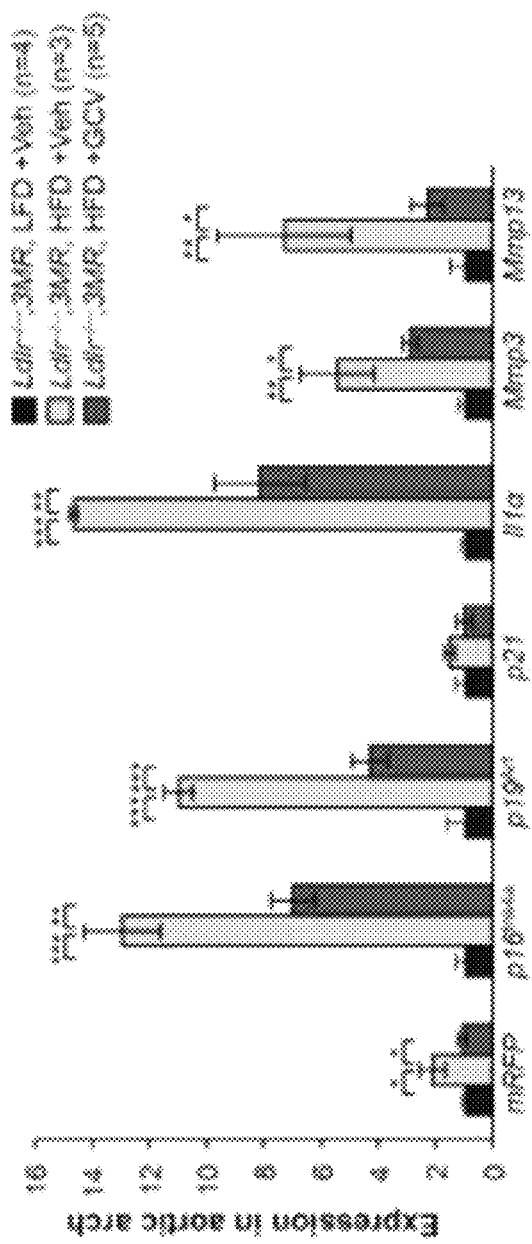

To assess the impact senescent cells have on plaque development, 10-week-old Ldlr$^{-/-}$;3MR mice were placed on a HFD for 88 days and simultaneously treated them with GCV or vehicle during this period (FIG. 1B) to intermittently remove p16$^{Ink4a}$-positive cells. Ldlr$^{-/-}$ mice on a HFD treated with GCV were included to control for potential effects of GCV independent of 3MR expression. En face staining of descending aortas with Sudan IV revealed that plaque burden was 60% lower in GCV-treated Ldlr$^{-/-}$;3MR mice than in vehicle-treated Ldlr$^{-/-}$;3MR or GCV-treated Ldlr$^{-/-}$ mice owing to decreases in both plaque number and size (FIG. 1C). Similarly, GCV-treated Ldlr$^{-/-}$;3MR mice showed reduced plaque burden and destruction of aortic elastic fibers beneath the neointima in the brachiocephalic artery (FIG. 6A-C), a site that rapidly develops advanced atherosclerotic plaques (17). GCV treated Ldlr$^{-/-}$;3MR mice expressed lower amounts of p16$^{Ink4a}$ mRNA and other senescence marker mRNAs in aortic arches than vehicle-treated Ldlr$^{-/-}$;3MR mice, confirming that p16$^{Ink4a+}$ senescent cells were efficiently cleared by GCV (FIG. 1D). Importantly, 3MR expression, as measured by qRT-PCR analysis of mRFP transcripts, increased in HFD fed mice, but remained at baseline levels with GCV treatment. Complementary en face SA-β-Gal staining of aortas confirmed that p16$^{Ink4a}$-positive senescent cells were effectively cleared (FIG. 6D). GCV treatment of Ldlr$^{-/-}$ mice did not alter SA-β-Gal staining or other senescence markers (FIG. 6D, E). GCV-treated Ldlr$^{-/-}$ and Ldlr$^{-/-}$;3MR mice did not differ in body weight, fat mass, and fat deposit weight (FIG. 7A-D). Circulating monocytes, lymphocytes, platelets, and neutrophils, all of which are involved in atherogenesis, were unaffected (FIG. 7E-H). Atherogenic lipids in the blood of GCV treated Ldlr$^{-/-}$ and Ldlr$^{-/-}$;3MR mice and vehicle-treated Ldlr$^{-/-}$;3MR mice were all highly elevated compared to LFD-fed controls, with no differences between the distinct HFD-fed cohorts (FIG. 7I). Thus, the athero-protective effect in GCV-treated Ldlr$^{-/-}$;3MR mice is due to the killing of p16$^{Ink4a+}$ senescent cells rather than changes in feeding habits, blood lipids or circulating immunocytes. Importantly, reductions in plaque burden, number and size observed with p16-3MR were reproducible with two independent transgenic systems designed to kill p16$^{Ink4a}$-positive senescent cells through distinct mechanisms, INK-ATTAC (FIG. 8) (18, 19) and INK-NTR (FIG. 9), as well as the senolytic drug ABT263 (FIG. 10) (20).

To investigate how senescent cells drive plaque initiation and growth, focus was placed on atherogenesis onset at lesion-prone sites of the vasculature (21). After just nine days on an atherogenic diet, Ldlr$^{-/-}$ mice had overtly detectable fatty streak lesions solely in the inner curvature of the aortic arch (FIG. 2A). Surprisingly, these early lesions were highly positive for SA-β-Gal activity (FIG. 2A). By contrast, Ldlr$^{-/-}$ mice containing 3MR and treated daily with GCV during the 9-day HFD-feeding period had low SA-β-Gal-activity and much smaller fatty streaks (FIG. 2A). Histological examination by TEM of the SA-β-Gal-stained samples revealed that fatty streaks of HFD-fed Ldlr-/- mice consisted of foci of foam cell macrophages arranged in mono- or multilayers (FIG. 2B, C). The lesions had intact elastic fibers and no fibrous cap. X-Gal crystals were detectable exclusively in foam cell macrophages, irrespective of lesion size (FIG. 2B, D). Foam cell macrophages in foci of 9-day lesions of Ldlr$^{-/-}$;3MR mice receiving daily, high-dose GCV were rarely arranged in multilayers and had a much lower incidence of crystals (FIG. 2C, D). High SA-β-Gal activity in fatty streaks correlated with increased levels of p16$^{Ink4a}$ and various other senescence markers, including Mmp3, Mmp13, Il1α and Tnfα (FIG. 7A). Nine-day treatment of HFD fed Ldlr$^{-/-}$ mice with ABT263 confirmed that senolysis reduces atherogenesis onset (FIG. 11B).

To determine how senescent foamy macrophages contribute to early atherogenesis, 9-day fatty streaks were established in Ldlr$^{-/-}$ and Ldlr$^{-/-}$;3MR mice and then administered high-dose GCV for 3 days while continuing HFD feeding. Short-term clearance of senescent cells markedly reduced streak size and SA-β-Gal positivity (FIG. 2E). TEM showed that cleared foci were drastically remodeled, with acellular debris retained in the subendothelium and few foamy macrophages containing X-Gal crystals (FIG. 11C, D). qRT-PCR revealed a stark reduction in p16$^{Ink4a}$ and SASP components, including Mmp3, Mmp13, Il1α and Tnfα, as well as two key molecular drivers of monocyte recruitment, the chemokine Mcp1 and the leukocyte receptor Vcam1, whose expression is driven in part by Tnfα (FIG. 2F). These data suggests that subendothelial senescent foamy macrophages arising in early lesions enhance Tnfα-mediated Vcam1 expression as well as the Mcp1 gradient to perpetuate monocyte recruitment from the blood. Next, the role of senescent cells in the maturation of benign plaques to volatile lesions was examined. Although mouse models for atherosclerosis do not develop clinical symptoms associated with plaque ruptures, plaque maturation in these mice can be studied using surrogate markers of plaque instability, including fibrous cap thinning (22, 23), decreased collagen deposition, elastic fiber degradation and plaque calcification (24). To assess the effect of senescent cell clearance on the maturation of existing plaques, late-disease senescent cell clearance protocols were employed in which Ldlr$^{-/-}$ and Ldlr$^{-/-}$;3MR mice were placed on HFD for 88 days to create established plaques, followed by 100 days of GCV treatment. During GCV treatment, mice were fed a HFD or LFD to promote continued plaque advancement or stasis, respectively (FIG. 3A and FIG. 12A). Ldlr$^{-/-}$;3MR mice maintained on the HFD and receiving GCV showed attenuated disease progression, as evidenced by a lower plaque number and size compared to GCV-treated Ldlr$^{-/-}$ or vehicle treated Ldlr-/-; 3MR controls (FIG. 3A). While plaques of GCV-treated Ldlr$^{-/-}$3 MR mice on a LFD had markedly reduced Sudan IV staining compared to plaques of control mice, the lesion-covered aortic area did not change (FIG. 3B), even though 3MR-mediated senescent cell killing was confirmed by SA-β-Gal staining and qRT-PCR for senescence markers (FIG. 3C, D). Senescent cell clearance reduced expression of the inflammatory cytokines (FIG. 3D) and monocyte recruitment factors, irrespective of diet (FIG. 12B, C). Importantly, GCV treatment decreased expression of matrix metalloproteases linked to plaque destabilization, including Mmp3, Mmp12 and Mmp13 (25, 26) (FIG. 3D), suggesting that senescent cell elimination stabilizes the fibrous cap.

To investigate this and other features of plaque maturation, histopathology was conducted on plaques collected from the above cohorts. Descending aorta plaques of Ldlr$^{-/-}$ mice fed a HFD for 88 days showed reduced cap thickness, diminished collagen content by Masson's trichrome staining, and more disrupted aortic elastic fibers (by Voerhoff von Gieson-staining) when mice were left for an additional 100 days on HFD, compared to LFD (FIG. 4A, B and FIG. 13). In contrast, all these markers of plaque instability were decreased with clearance of p16$^{Ink4a+}$ cells regardless of diet during the 100-day GVC treatment period. Similarly, clearance of p16$^{Ink4a+}$ cells increased cap thickness and collagen content in brachiocephalic arteries from mice reverted to LFD (FIG. 14). These studies were extended by switching Ldlr$^{-/-}$;3MR and Ldlr$^{-/-}$ mice after 88 days of HFD feeding to a LFD with GVC injections for 35 days (FIG. 15A). In this experiment, senescent cell elimination preserved fibrous cap thickness (FIG. 15B, C). Furthermore, lesional foamy macrophage-like cell content was reduced while VSMC-like cell content increased (FIG. 15D, E), resulting in plaques with a higher VSMC-like/macrophage-like cell ratio, a marker for greater stability (FIG. 15F) (27). Numbers of circulating monocytes adhering to plaque-adjacent endothelium were substantially reduced upon clearance (FIG. 15G), supporting our conclusion from early fatty streak experiments that enhanced monocyte chemotaxis may partially explain the proatherogenic nature of senescent cells. These results strongly suggest that eliminating p16$^{Ink4a+}$ cells promotes plaque stability.

To further investigate the mechanism by which senescent cells drive atherogenesis, the possibility that senescent cells in plaques express proatherogenic factors was tested. Lesion bearing tissue from HFD-fed Ldlr$^{-/-}$;ATTAC mice was dissected and single cell suspensions were prepared. p16$^{Ink4a}$-dependent expression of GFP by ATTAC was exploited to collect GFP$^+$ senescent and GFP$^-$ non-senescent cell populations for analysis by qRT-PCR (FIG. 4C). Indeed, senescent cells expressed a broad spectrum of proatherogenic factors, including Il1α, Tnfα, Mmp3, Mmp12, and Mmp13, Mcp1 and Vcam1 (FIG. 4C). A subset of these factors was expressed at markedly elevated levels compared to non-senescent cells, including Il1α, Mmp12, Mmp13 and Mcp1.

Using both transgenic and pharmacological approaches to clear p16$^{Ink4a}$-positive cells without interfering with the senescence program, it was shown that senescent cells are uniformly deleterious throughout atherogenesis. Very early fatty streaks contain abundant senescent foam cell macrophages, which create an environment conducive to further lesion growth by upregulating inflammatory cytokines and monocyte chemotactic factors. Removing p16$^{Ink4a}$-positive foamy macrophages from fatty streaks led to marked lesion regression. In contrast, advanced plaques contain three morphologically distinct senescent cell types that not only drive lesion maturation through inflammation and monocyte chemotaxis, but also promote extracellular matrix degradation. While clearing senescent cells did not regress advanced lesions, it does arrest maladaptive plaque remodeling processes including fibrous cap thinning, a risk factor for plaque instability. Furthermore, senescent cells in lesions show heightened expression of key SASP factors and effectors of inflammation, monocyte chemotaxis, and proteolysis, including Il1α, Mcp1, Mmp12 and Mmp13. These data suggest that senescent cells can directly influence core proatherogenic processes through specific secreted factors. By comparison, other factors such as Mmp3, Tnfα, and Vcam1 are reduced with senescent cell clearance but not significantly enriched in p16$^{Ink4a}$-positive cells, implying that senescent cells also can influence the proatherogenic milieu indirectly. Collectively, our results show that senescent cells drive atherosclerosis at all stages through paracrine activity and raise the possibility that removal of these cells could contribute to therapeutically managing atherosclerosis.

Source Materials

C57BL/6 Ldlr-/- mice were purchased from the Jackson Laboratory (stock number 002207), crossed with previously described C57BL/6 3MR mice (15) to generate Ldlr+/-; 3MR mice, which were then bred to C57BL/6 Ldlr-/- mice to produce Ldlr-/-;3MR males. Female mice used in experiments were generated by breeding Ldlr-/-;3MR males to C57BL/6 Ldlr-/- females. Experimental mice contained a single copy of the 3MR transgene. INK-ATTAC transgenic mice on a C57BL/6 background were established as described (27). These mice contain 13 tandem copies of the INK-ATTAC transgene integrated into a single genomic locus (27). Breeding the INK-ATTAC transgene onto the Ldlr−/− background and experimental cohort production was performed as described for Ldlr−/−;3MR. Experimental mice were hemizygous for INK-ATTAC. INK-NTR mice were generated by replacing the FKBP-Casp8-IRES-EGFP segment of the INK-ATTAC transgene cassette with an EGFP-NTR fusion gene (NTR was amplified from *E. coli* BL21) (28). The transgene was injected into FVB fertilized eggs yielding 14 transgenic founders of which eight were bred onto a BubR1 progeroid background (29). BubR1H/H;INK-NTR and BubR1H/H littermates for each founder line were given ad libitum access to drinking water containing 4.5 g/l MTZ (Sigma-Aldrich) and 90 g/l sugar beginning at weaning age and were subsequently monitored for the time to onset of cataracts, kyphosis and lipodystrophy as described (18). Two transgenic lines markedly attenuate these features and one was selected for breeding to Ldlr−/− mice (line 18; these mice were of a FVBx129Sv/Ex C57BL/6 mixed genetic background). Experimental mice were generated by breeding Ldlr−/−;INK-NTR males to C57BL/6 Ldlr−/− females. Ldlr−/−;INK-NTR females used in experiments were hemizygous for INK-NTR and had been backcrossed to C57BL/6 for at least 3 generations.

Atherosclerosis Induction and Senescent Cell Clearance

To induce atherosclerosis, female mice were fed an atherogenic diet consisting of 42% calories from fat (Harlan-Teklad, TD.88137) starting from 10 weeks of age. Progression studies in FIG. 1 and FIG. 5-10 used 88 days (12.5 weeks) of HFD feeding prior to sacrifice, with the exception of FIG. 9, which used 102 days of HFD. For studies using the 3MR system, 5 mg/kg ganciclovir (GCV) in PBS was delivered intraperitoneally (IP) to Ldlr−/− controls and Ldlr−/−;3MR experimental mice once daily for 5 days, followed by 14 days off on a repeating cycle for the duration of the study. PBS-injected Ldlr−/−;3MR were also put on HFD as controls for transgene-insertion effects. For studies using metronidazole, Ldlr−/− controls and Ldlr−/−;NTR experimental mice were given ad libitum drinking water containing 4.5 g/l metronidazole (Sigma-Aldrich) and 90 g/l sugar. For studies using AP20187, Ldlr−/− controls and Ldlr−/−;ATTAC experimental mice were given 2 mg/kg AP20187 via IP injection twice-weekly as described (27) for the duration of the study.

To induce fatty streaks in FIG. 2 and FIG. 11, Ldlr−/− and Ldlr−/−;3MR mice were fed HFD for 9 days with once-daily injections of 25 mg/kg GCV in PBS (referred to as high-dose GCV in the main text) or 100 mg/kg ABT263 in vehicle (PBS with 15% DMSO/7% Tween-20). To regress fatty streaks, mice were pre-fed HFD for 9 days, followed by a further 3 days of HFD with 25 mg/kg GCV in PBS delivered 3× daily.

Late-stage progression in FIG. 3-4 and FIG. 12-10 was studied by feeding HFD to Ldlr−/− and Ldlr−/−;3MR mice for 188 days, where treating (PBS vehicle or 5 mg/kg GCV) during the last 100 days on a 5 days on, 14 days off cycle. Late-stage regression in FIG. 3-4 and FIG. 12-10 was studied used 88 days of HFD followed by a switch back to non-atherogenic standard irradiated pelleted chow diet (LabDiet #5053, 13.205% calories from fat) with vehicle or GCV treatment as above. Non-atherosclerotic controls were fed this same non-atherogenic diet lifelong and treated with PBS vehicle for the last 100 days of the study.

Blood Profiling

Prior to sacrifice, blood was collected by retro-orbital puncture using heparinized capillary tubes. Gross hematology for circulating cells was assessed by analyzing EDTA-treated whole blood using a Hemavet 950 (Drew Scientific Inc., Miami Lakes, Fla., USA). Plasma was prepared by EDTA treating whole blood followed by centrifugation at 4° C. for 15 min at 3500 g. Lipid analysis was performed by the Mayo Clinic Immunochemical Core Laboratory (ICL) using high-performance liquid chromatography (HPLC).

SA-β-Gal Staining and Gal-EM

SA-3-Gal staining on mouse aortas was performed using a kit according to the manufacturer's instructions (Cell Signaling). Whole mouse aortas were excised and stored in PBS on ice until fixation. Aortas were fixed for 15 min at RT, washed twice in PBS, and developed in staining solution for 12 h at 37° C. Electron microscopy on SA-β-Gal-stained plaques (Gal-EM) was performed as described (27). Briefly, following SA-β-Gal staining, plaques were post-fixed in Trump's fixative for 4 h at RT, followed by standard EM processing (dehydration through xylene-alcohol series, followed by osmium tetroxide staining and embedding in Epon resin). For quantification of SA-β-Gal-positive cells in FIG. 1, two non-adjacent thin sections were analyzed per descending aorta plaque, with cells bearing one or more cuboidal or needle-shaped X-Gal crystals considered to be X-Gal+. Foamy macrophage-like cells, VSMC-like cells, endothelial-like cells, and adherent monocytes were identified morphologically. Briefly, cells with roughly circular shape and the entire cytoplasm occupied with vacuoles are considered macrophage-like.

Spindle-shaped or highly ramified cells with electron-dense, largely unvacuolated cytoplasm rich in Golgi/endoplasmic reticulum are considered vascular smooth muscle-like cells. Cells localized to the plaque surface with elongated nuclei and long, thin cytoplasm are considered endothelium. These morphological assessments fully disregard cellular origin given cell-type interconversion prevalent in lesions, and thus describe cells as '-like' in order to capture broad phenotypic categories. For quantification of plaque histological parameters in FIG. 14, one or more thin sections were analyzed per descending aorta plaque. Cap thickness was measured at 15 equally dispersed sites per section on 600× magnification TEM images using ImageJ. VSMC-like and macrophage-like cell content were analyzed on these same sections by manually counting all such cells at 1500× magnification and normalizing to plaque cross-sectional area. Adherent monocytes, which were only found on endothelium adjacent to plaques, were counted in two non-adjacent sections for each plaque and are presented without normalization to endothelial cell numbers because quantity of adjacent vessel wall was approximately equal between groups.

En Face Staining for Plaques

Whole aortas were dissected clean of adventitial fat, opened, and pinned flat in 4% paraformaldehyde (PFA) for 12 h at RT as previously described (30). Staining was conducted by washing pinned aortas for 5 min with 70% ethanol, incubating in Sudan IV working solution (0.5% Sudan IV in 1:1 acetone:ethanol) for 5 min, followed by differentiating three times for 30 sec with 80% ethanol. For all experiments, control and experimental aortas were stained simultaneously. Quantification of total Sudan IV+ area was done using ImageJ and plaques were counted at 40× magnification.

Flow Cytometry

Lesion bearing aortic arches and abdominal aortas from Ldlr−/−;ATTAC and Ldlr−/− fed a HFD for 6 months were isolated into ice-cold PBS and washed three times, before being finely minced in Hank's balanced salt solution (HBSS) with 1 mg/ml Liberase™ (Roche Life Science). Samples were incubated at 37° C. for 1 hr with inversion every ten min, and 10× trituration through a fire-polished glass pipette at 30 min and the end of digestion to disrupt the tissue. Samples were passed over a 70 μm nylon cell strainer and the filter was rinsed with 2 ml HBSS with 5% normal goat serum (NGS) to collect cells, which were pelleted at 300 g for 4 min at 4° C. and resuspended in 0.75 ml HBSS with 5% NGS. Samples were stored on ice until flow sorting. Gating against autofluorescence in the GFP channel was accomplished using Ldlr-/- lesional cells as a negative control. Cells were sorted on a FACS Aria 5 (non-sterile, 4° C.) directly into RNeasy Microkit lysis buffer (RLT with 1% β-mercaptoethanol). Samples were stored on ice until RNA isolation according to the manufacturer's protocol, after which RNA was stored at -80° C.

Quantitative Real Time PCR

Total RNA was extracted from ground aortic arches as described (27) or from flow-sorted cells as described above. cDNA was prepared using Superscript III first-strand cDNA synthesis kits according to manufacturer's protocol. qRT-PCR was performed using Sybr Green (Life Technologies) according to manufacturer's recommendations and expression of target genes was normalized to individual sample GAPDH levels. Primers used to amplify $p16^{Ink4a}$, p19Arf, p21, Mmp3, Mmp13, Il1α, Tnfα and mRFP transcripts were previously described (15, 27).

Histological Assessment of Plaques

Individual descending aorta plaques or intact brachiocephalic arteries were processed following a 12-h RT fixation in 4% PFA or 10% neutral buffered formaldehyde, respectively. All sections were 5 μm thick. For descending aorta plaques, at least 2 plaque-bearing sections obtained 250 μm apart were scored for all parameters. For brachiocephalic arteries, scoring was performed on sections collected in unbiased fashion 200 μm apart beginning at the brachiocephalic root and ending at the bifurcation into the right common carotid and subclavian arteries. Routine H&E staining was used in conjunction with Masson's trichrome (Sigma-Aldrich) or Voerhoff von Gieson (Polyscientific R&D) stains to measure fibrous cap thickness and broken elastic fibers, respectively. The fibrous cap was defined as an eosinophilic, Alcian blue-positive structure overlaying the plaque core, with no more than one macrophage foam cell overlying or interpenetrating the cap. Fifteen equally dispersed measurements of cap thickness were taken for each plaque section. The percentage of collagen was measured using blue-stained area in Masson's trichrome, with the plaque cross sectional area measured only above elastic fiber closest to the lumen.

Statistical Analyses

Prism software was used to perform all statistical analyses. Student's two-tailed t-test with Welch's correction was applied to determine significance for all comparisons involving two groups only. For all experiments involving three or more groups, ANOVA was performed with compensation for multiple comparisons via Sidak familywise error rate correction. For consistency, in all graphs error bars represent standard error of the mean and significance is indicated by the scheme: *$P<0.05$; $P<0.01$; *, $P<0.001$. Biological 'n' is indicated directly on all graphs.

Senolytic Agents

Senolytic agents suitable for use in this invention include but are not limited to the compounds described in this section. Many senolytic agents share the characteristic that, at certain dosages, concentrations, or modes of delivery, the senolytic agents differentially or selectively kill or clear senescent cells in a mammal to which they are administered or in an in vitro assay.

A partial list is included below.

Small Molecules

Senolytic agents that may be used in the methods for treating or preventing a senescence-associated disease or disorder include small organic molecules. Small organic molecules (also called small molecules or small molecule compounds herein) typically have molecular weights less than 105 daltons, less than 104 daltons, or less than 103 daltons. In certain embodiments, a small molecule senolytic agent does not violate the following criteria more than once: (1) no more than 5 hydrogen bond donors (the total number of nitrogen-hydrogen and oxygen-hydrogen bonds); (2) not more than 10 hydrogen bond acceptors (all nitrogen or oxygen atoms); (3) a molecular mass less than 500 daltons; (4) an octanol-water partition coefficient[5] log P not greater than 5.

MDM2 Inhibitors

In certain embodiments, the senolytic agent may be an MDM2 inhibitor. An MDM2 (murine double minute 2) inhibitor that may be used in the methods for selectively killing senescent cells and treating or preventing (i.e., reducing or decreasing the likelihood of occurrence or development of) a senescence-associated disease or disorder may be a small molecule compound that belongs to any one of the following classes of compounds, for example, a cis-imidazoline compound, a spiro-oxindole compound, a benzodiazepine compound, a piperidinone compound, a tryptamine compound, and CGM097, and related analogs. In certain embodiments, the MDM2 inhibitor is also capable of binding to and inhibiting an activity of MDMX (murine double minute X, which is also known as HDMX in humans). The human homolog of MDM2 is called HDM2 (human double minute 2) in the art. Therefore, when a subject treated by the methods described herein is a human subject, the compounds described herein as MDM2 inhibitors also inhibit binding of HDM2 to one or more of its ligands.

MDM2 is described in the art as an E3 ubiquitin ligase that can promote tumor formation by targeting tumor suppressor proteins, such as p53, for proteasomal degradation through the 26S proteasome (see, e.g., Haupt et al. *Nature* 387: 296-299 1997; Honda et al., *FEBS Lett* 420: 25-27 (1997); Kubbutat et al., *Nature* 387: 299-303 (1997)). MDM2 also affects p53 by directly binding to the N-terminal end of p53, which inhibits the transcriptional activation function of p53 (see, e.g., Momand et al., *Cell* 69: 1237-1245 (1992); Oliner et al., *Nature* 362: 857-860 (1993)). Mdm2 is in turn regulated by p53; p53 response elements are located in the promoter of the Mdm2 gene (see, e.g., Barak et al., *EMBO J* 12:461-68 (1993)); Juven et al., *Oncogene* 8:3411-16 (1993)); Perry et al., *Proc. Natl. Acad. Sci.* 90:11623-27 (1993)). The existence of this negative feedback loop between p53 and Mdm2 has been confirmed by single-cell studies (see, e.g., Lahav, *Exp. Med. Biol.* 641: 28-38 (2008)). See also Manfredi, *Genes & Development* 24:1580-89 (2010). Reports have described several activities and biological functions of MDM2.

These reported activities include the following: acts as a ubiquitin ligase E3 toward itself and ARRB1; permits nuclear export of p53; promotes proteasome-dependent ubiquitin-independent degradation of retinoblastoma RB1 protein; inhibits DAXX-mediated apoptosis by inducing its ubiquitination and degradation; component of TRIM28/KAP1-MDM2-p53 complex involved in stabilizing p53; component of TRIM28/KAP1-ERBB4-MDM2 complex that links growth factor and DNA damage response pathways; mediates ubiquitination and subsequent proteasome degradation of DYRK2 in the nucleus; ubiquitinates IGF1R and SNAI1 and promotes them to proteasomal degradation.

MDM2 has also been reported to induce mono-ubiquitination of the transcription factor FOXO4 (see, e.g., Brenkman et al., PLOS One 3(7):e2819, doi:10.1371/journal.pone.0002819). The MDM2 inhibitors described herein may disrupt the interaction between MDM2 and any one or more of the aforementioned cellular components.

In one embodiment, a compound useful for the methods described herein is a cis-imidazoline small molecule inhibitor. Cis-imidazoline compounds include those called nutlins in the art. Similar to other MDM2 inhibitors described herein, nutlins are cis-imidazoline small molecule inhibitors of the interaction between MDM2 and p53 (see Vassilev et al., Science 303 (5659): 844-48 (2004)). Exemplary cis-imidazolines compounds that may be used in the methods for selectively killing senescent cells and treating or preventing (i.e., reducing or decreasing the likelihood of occurrence or development of) a senescence-associated disease or disorder are described in U.S. Pat. Nos. 6,734,302; 6,617,346; 7,705,007 and in U.S. Patent Application Publication Nos. 2005/0282803; 2007/0129416; 2013/0225603. In certain embodiments, the methods described herein comprise use of a nutlin compound called Nutlin-1; or a nutlin compound called Nutlin-2; or a Nutlin compound called Nutlin-3 (see CAS Registry No. 675576-98-4 and No. 548472-68-0). The active enantiomer of Nutlin-3 (4-[[4S,5R)-4,5-bis(4-chlorophenyl)-4,5-dihydro-2-[4-methoxy-2-(1-methylethoxy)phenyl]-1H-imidazol-1-yl]carbonyl]-2-piperazinone) is called Nutlin-3a in the art. In certain embodiments, the methods described herein comprise use of Nutlin-3a for selectively killing senescent cells. Nutlin-3 is described in the art as a non-genotoxic activator of the p53 pathway, and the activation of p53 is controlled by the murine double minute 2 (MDM2) gene. The MDM2 protein is an E3 ubiquitin ligase and controls p53 half-life by way of ubiquitin-dependent degradation. Nutlin-3a has been investigated in pre-clinical studies (e.g., with respect to pediatric cancers) and clinical trials for treatment of certain cancers (e.g., retinoblastoma). To date in vitro and pre-clinical studies with Nutlin-3 have suggested that the compound has variable biological effects on the function of cells exposed to the compound. For example, Nutlin-3 reportedly increases the degree of apoptosis of cancer cells in hematological malignancies including B-cell malignancies (see, e.g., Zauli et al., Clin. Cancer Res. 17:762-70 (2011; online publication on Nov. 24, 2010) and references cited therein) and in combination with other chemotherapeutic drugs, such as dasatinib, the cytotoxic effect appears synergistic (see, e.g., Zauli et al., supra).

More generally, a family of MDM2 inhibitors that includes Nutlin-3 may be represented by Formula (I):

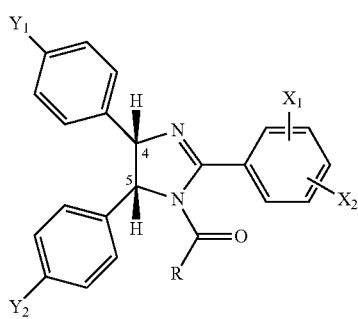

(I)

wherein R is selected from saturated and unsaturated 5- and 6-membered rings containing at least one hetero atom, wherein the hetero atom is selected from S, N and O and is optionally substituted with a group selected from lower alkyl, cycloalkyl, —C=O—$R_1$, hydroxy, lower alkyl substituted with hydroxy, lower alkyl substituted with lower alkoxy, lower alkyl substituted with —$NH_2$, lower alkyl substituted with —C=O—$R_1$, N-lower alkyl, —$SO_2CH_3$, =O and —$CH_2C$=$OCH_3$;

$R_1$ is selected from hydrogen, lower alkyl, —$NH_2$, —N-lower alkyl, lower alkyl substituted with hydroxy, lower alkyl substituted with —$NH_2$, and a 5- or 6-membered saturated ring containing at least one hetero atom selected from S, N and O;

$X_1$ and $X_2$ are each independently selected from hydrogen, lower alkoxy, —$CH_2OCH_3$, —$CH_2OCH_2CH_3$, —$OCH_2CF_3$, and —$OCH_2CH_2F$; and $Y_1$ and $Y_2$ are each independently selected from —Cl, —Br, —$NO_2$, —C≡N, and —C≡CH;

wherein the composition contains a formulation of the compound suitable for administration to subject who has atherosclerosis; and wherein the formulation of the composition and the amount of the compound in the unit dose configure the unit dose to be effective in treating the atherosclerosis by eliminating p16 positive senescent cells in or around atherosclerotic plaques in the subject, thereby stabilizing the plaques so as to reduce the risk that the plaques will rupture.

Another exemplary cis-imidazoline small molecule compound useful for selectively killing senescent cells is RG-7112 (Roche) (CAS No: 939981-39-2; IUPAC name: ((4S,5R)-2-(4-(tert-butyl)-2-ethoxyphenyl)-4,5-bis(4-chlorophenyl)-4,5-dimethyl-4,5-dihydro-1H-imidazol-1-yl)(4-(3-(methylsulfonyl)propyl)piperazin-1-yl)methanone. See U.S. Pat. No. 7,851,626; Tovar et al., Cancer Res. 72:2587-97 (2013).

The MDM2 inhibitor may be a cis-imidazoline compound called RG7338 (Roche) (IPUAC Name: 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoic acid) (CAS 1229705-06-9); Ding et al., J. Med. Chem. 56(14):5979-83. Doi: 10.1021/jm400487c. Epub 2013 Jul. 16; Zhao et al., J. Med. Chem. 56(13):5553-61 (2013) doi: 10.1021/jm4005708. Epub 2013 Jun. 20). Yet another exemplary nutlin compound is RO5503781. Other potent cis-imidazoline small molecule compounds include dihydroimidazothiazole compounds (e.g., DS-3032b; Daiichi Sankyo) described by Miyazaki, (see, e.g., Miyazaki et al., Bioorg. Med. Chem. Lett. 23(3):728-32 (2013) doi: 10.1016/j.bmcl.2012.11.091. Epub 2012 Dec. 1; Miyazaki et al., Bioorg. Med. Chem. Lett. 22(20):6338-42 (2012) doi: 10.1016/j.bmcl.2012.08.086. Epub 2012 Aug. 30; Intl Patent Appl. Publ. No. WO 2009/151069 (2009)).

Another cis-imidazoline compound that may be used in the methods described herein is a dihydroimidazothiazole compound. Alternatively, the MDM2 small molecule inhibitor is a spiro-oxindole compound. See, for example, compounds described in Ding et al., J. Am. Chem. Soc. 2005; 127:10130-31; Shangary et al., Proc Natl Acad Sci USA 2008; 105:3933-38; Shangary et al., Mol Cancer Ther 2008; 7:1533-42; Shangary et al., Mol Cancer Ther 2008; 7:1533-42; Hardcastle et al., Bioorg. Med. Chem. Lett. 15:1515-20 (2005); Hardcastle et al., J. Med. Chem. 49(21):6209-21 (2006); Watson et al., Bioorg. Med. Chem. Lett. 21(19): 5916-9 (2011) doi: 10.1016/j.bmcl.2011.07.084. Epub 2011 Aug. 9. Other examples of spiro-oxindole compounds that are MDM2 inhibitors are called in the art MI-63, MI-126; MI-122, MI-142, MI-147, MI-18, MI-219, MI-220, MI-221, and MI-773. Another specific spiro-oxindole compound is 3-(4-chlorophenyl)-3-((1-(hydroxymethyl)cyclopropyl)methoxy)-2-(4-nitrobenzyl)isoindolin-1-one. Another compound is called MI888 (see, e.g., Zhao et al., J. Med. Chem. 56(13):5553-61 (2013); Int'l Patent Appl. Publ. No. WO 2012/065022).

The MDM2 small molecule inhibitor may be a benzodiazepinedione (see, e.g., Grasberger et al., J Med Chem 2005; 48:909-12; Parks et al., Bioorg Med Chem Lett 2005; 15:765-70; Raboisson et al., Bioorg. Med. Chem. Lett. 15:1857-61 (2005); Koblish et al., Mol. Cancer Ther. 5:160-69 (2006)). Benzodiazepinedione compounds that may be used in the methods described herein include 1,4-benzodiazepin-2,5-dione compounds. Examples of benzodiazepinedione compounds include 5-[(3S)-3-(4-chlorophenyl)-4-[(R)-1-(4-chlorophenyl)ethyl]-2,5-dioxo-7-phenyl-1,4-diazepin-1-yl]valeric acid and 5-[(3S)-7-(2-bromophenyl)-3-(4-chlorophenyl)-4-[(R)-1-(4-chlorophenyl)ethyl]-2,5-dioxo-1,4-diazepin-1-yl]valeric acid (see, e.g., Raboisson et al., supra). Other benzodiazepinedione compounds are called in the art TDP521252 (IUPAC Name: 5-[(3S)-3-(4-chlorophenyl)-4-[(1R)-1-(4-chlorophenyl)ethyl]-7-ethynyl-2,5-dioxo-3H-1,4-benzodiazepin-1-yl]pentanoic acid) and TDP665759 (IUPAC Name: (3S)-4-[(1R)-1-(2-amino-4-chlorophenyl)ethyl]-3-(4-chlorophenyl)-7-iodo-1-[3-(4-methylpiperazin-1-yl)propyl]-3H-1,4-benzodiazepine-2,5-dione) (see, e.g., Parks et al., supra; Koblish et al., supra) (Johnson & Johnson, New Brunswick, N.J.).

In yet another embodiment, the MDM2 small molecule inhibitor is a terphenyl (see, e.g., Yin et al., Angew Chem Int Ed Engl 2005; 44:2704-707; Chen et al., Mol Cancer Ther 2005; 4:1019-25). In yet another specific embodiment, the MDM2 inhibitor that may be used in the methods described herein is a quilinol (see, e.g., Lu et al., J Med Chem 2006; 49:3759-62). In yet another certain embodiment, the MDM2 inhibitor is a chalcone (see, e.g., Stoll et al., Biochemistry 2001; 40:336-44). In yet another particular embodiment, the MDM2 inhibitor is a sulfonamide (e.g., NSC279287) (see, e.g., Galatin et al., J Med Chem 2004; 47:4163-65).

In other embodiments, a compound that may be used in the methods described herein is a tryptamine, such as serdemetan (JNJ-26854165; chemical name: N1-(2-(1H-indol-3-yl)ethyl)-N4-(pyridine-4-yl)benzene-1,4-diamine; CAS No. 881202-45-5) (Johnson & Johnson, New Brunswick, N.J.). Serdemetan is a tryptamine derivative that activates p53 and acts as a HDM2 ubiquitin ligase antagonist (see, e.g., Chargari et al., Cancer Lett. 312(2):209-18 (2011) doi: 10.1016/j.canlet.2011.08.011. Epub 2011 Aug. 22; Kojima et al., Mol. Cancer Ther. 9:2545-57 (2010); Yuan et al., J. Hematol. Oncol. 4:16 (2011)).

In other particular embodiments, MDM2 small molecule inhibitors that may be used in the methods described herein include those described in Rew et al., J. Med. Chem. 55:4936-54 (2012); Gonzalez-Lopez de Turiso et al., J. Med. Chem. 56:4053-70 (2013); Sun et al., J. Med. Chem. 57:1454-72 (2014); Gonzalez et al., J. Med. Chem. 2014 Mar. 4 [Epub ahead of print]; Gonzalez et al., J. Med. Chem. 2014 Mar. 6 [Epub ahead of print].

In still other embodiments, the MDM2 inhibitor is a piperidinone compound. An example of a potent MDM2 piperidinone inhibitor is AM-8553 ({(3R,5R,6S)-5-(3-Chlorophenyl)-6-(4-chlorophenyl)-1-[(2S,3S)-2-hydroxy-3-pentanyl]-3-methyl-2-oxo-3-piperidinyl}acetic acid; CAS No. 1352064-70-0) (Amgen, Thousand Oaks, Calif.).

In other particular embodiments, an MDM2 inhibitor that may be used in the methods described herein is a piperidine (Merck, Whitehouse Station, N.J.) (see, e.g., Int'l Patent Appl. Publ. No. WO 2011/046771). In other embodiments, an MDM2 inhibitor that may be used in the methods is an imidazole-indole compound (Novartis) (see, e.g., Int'l Patent Appl. Publ. No. WO 2008/119741). Examples of compounds that bind to MDM2 and to MDMX and that may be used in the methods described herein include RO-2443 and RO-5963 ((Z)-2-(4-((6-Chloro-7-methyl-1H-indol-3-yl)methylene)-2,5-dioxoimidazolidin-1-yl)-2-(3,4-difluorophenyl)-N-(1,3-dihydroxypropan-2-yl)acetamide) (see, e.g., Graves et al., Proc. Natl. Acad. Sci. USA 109:11788-93 (2012); see also, e.g., Zhao et al., 2013, BioDiscovery, supra). In another specific embodiment, an MDM2 inhibitor referred to in the art as CGM097 may be used in the methods described herein for selectively killing senescent cells and for treating a senescence-associated disease or disorder.

Inhibitors of Bcl-2 Anti-Apoptotic Family of Proteins

In certain embodiments, the senolytic agent may be an inhibitor of one or more proteins in the Bcl-2 family. In certain embodiments, the at least one senolytic agent is selected from an inhibitor of one or more Bcl-2 anti-apoptotic protein family members wherein the inhibitor inhibits at least Bcl-xL. Inhibitors of Bcl-2 anti-apoptotic family of proteins alter at least a cell survival pathway. Apoptosis activation may occur via an extrinsic pathway triggered by the activation of cell surface death receptors or an intrinsic pathway triggered by developmental cues and diverse intracellular stresses. This intrinsic pathway, also known as the stress pathway or mitochondrial pathway, is primarily regulated by the Bcl-2 family, a class of key regulators of caspase activation consisting of anti-apoptotic (pro-survival) proteins having BH1-BH4 domains (Bcl-2 (i.e., the Bcl-2 protein member of the Bcl-2 anti-apoptotic protein family), Bcl-xL, Bcl-w, A1, MCL-1, and Bcl-B); pro-apoptotic proteins having BH1, BH2, and BH3 domains (BAX, BAK, and BOK); and pro-apoptotic BH3-only proteins (BIK, BAD, BID, BIM, BMF, HRK, NOXA, and PUMA) (see, e.g., Cory et al., Nature Reviews Cancer 2:647-56 (2002); Cory et al., Cancer Cell 8:5-6 (2005); Adams et al., Oncogene 26:1324-1337 (2007)). Bcl-2 anti-apoptotic proteins block activation of pro-apoptotic multi-domain proteins BAX and BAK (see, e.g., Adams et al., Oncogene 26:1324-37 (2007)).

It is hypothesized that BH3-only proteins unleashed by intracellular stress signals bind to anti-apoptotic Bcl-2 like proteins via a BH3 "ligand" to a "receptor" BH3 binding groove formed by BH1-3 regions on anti-apoptotic proteins, thereby neutralizing the anti-apoptotic proteins (see, e.g., Letai et al., Cancer Cell 2:183-92 (2002); Adams et al., Oncogene, supra). BAX and BAK can then form oligomers in mitochondrial membranes, leading to membrane permeabilization, release of cytochrome C, caspase activation, and ultimately apoptosis (see, e.g., Adams et al., Oncogene, supra).

As used herein and unless otherwise stated, a Bcl-2 family member that is inhibited by the agents described herein is a pro-survival (anti-apoptotic) family member. The senolytic agents used in the methods described herein inhibit one or more functions of the Bcl-2 anti-apoptotic protein, Bcl-xL (which may also be written herein and in the art as Bcl-xL, Bcl-XL, Bcl-xl, or Bcl-XL). In certain embodiments, in addition to inhibiting Bcl-xL function, the inhibitor may also interact with and/or inhibit one or more functions of Bcl-2 (i.e., Bcl-xL/Bcl-2 inhibitors). In yet another certain embodiment, senolytic agents used in the methods described herein are classified as inhibitors of each of Bcl-xL and Bcl-w (i.e., Bcl-xL/Bcl-w inhibitors). In still another specific embodiment, senolytic agents used in the methods described herein that inhibit Bcl-xL may also interact with and inhibit one or more functions of each of Bcl-2 (i.e., the Bcl-2 protein) and Bcl-w (i.e., Bcl-xL/Bcl-2/Bcl-w inhibitors), thereby causing selective killing of senescent cells. In certain embodiments, a Bcl-2 anti-apoptotic protein inhibitor interferes with the interaction between the Bcl-2 anti-apoptotic protein family member (which includes at least Bcl-xL) and one or more ligands or receptors to which the Bcl-2 anti-apoptotic protein family member would bind in the absence of the inhibitor. In other particular embodiments, an inhibitor of one or more Bcl-2 anti-apoptotic protein family members wherein the inhibitor inhibits at least Bcl-xL specifically binds only to one or more of Bcl-xL, Bcl-2, Bcl-w and not to other Bcl-2 anti-apoptotic Bcl-2 family members, such as Mcl-1 and Bcl-2A1.

In still another embodiment, the senolytic agent used in the methods described herein is a Bcl-xL selective inhibitor and inhibits one or more functions of Bcl-xL. Such senolytic agents that are Bcl-xL selective inhibitors do not inhibit the function of one or more other Bcl-2 anti-apoptotic proteins in a biologically or statistically significant manner. Bcl-xL may also be called Bcl-2L1, Bcl-2-like 1, Bcl-X, Bcl-2L, Bcl-xL, or Bcl-X herein and in the art. In one embodiment, Bcl-xL selective inhibitors alter (e.g., reduce, inhibit, decrease, suppress) one or more functions of Bcl-xL but do not significantly inhibit one or more functions of other proteins in the Bcl-2 anti-apoptotic protein family (e.g., Bcl-2 or Bcl-w). In certain embodiments, a Bcl-xL selective inhibitor interferes with the interaction between Bcl-xL and one or more ligands or receptors to which Bcl-xL would bind in the absence of the inhibitor. In certain particular embodiments, a senolytic agent that inhibits one or more of the functions of Bcl-xL selectively binds to human Bcl-xL but not to other proteins in the Bcl-2 family, which effects selective killing of senescent cells.

Bcl-xL is an anti-apoptotic member of the Bcl-2 protein family. Bcl-xL also plays an important role in the crosstalk between autophagy and apoptosis (see, e.g., Zhou et al., FEBS J. 278:403-13 (2011)). Bcl-xL also appears to play a role in bioenergetic metabolism, including mitochondrial ATP production, Ca2+ fluxes, and protein acetylation, as well as on several other cellular and organismal processes such as mitosis, platelet aggregation, and synaptic efficiency (see, e.g., Michels et al., International Journal of Cell Biology, vol. 2013, Article ID 705294, 10 pages, 2013. doi:10.1155/2013/705294). In certain embodiments, the Bcl-xL inhibitors described herein may disrupt the interaction between Bcl-xL and any one or more of the aforementioned BH3-only proteins to promote apoptosis in cells.

In certain embodiments, a Bcl-xL inhibitor is a selective inhibitor, meaning, that it preferentially binds to Bcl-xL over other anti-apoptotic Bcl-2 family members (e.g., Bcl-2, MCL-1, Bcl-w, Bcl-b, and BFL-1/A1).

Methods for measuring binding affinity of a Bcl-xL inhibitor for Bcl-2 family proteins are known in the art. By way of example, binding affinity of a Bcl-xL inhibitor may be determined using a competition fluorescence polarization assay in which a fluorescent BAK BH3 domain peptide is incubated with Bcl-xL protein (or other Bcl-2 family protein) in the presence or absence of increasing concentrations of the Bcl-XL inhibitor as previously described (see, e.g., U.S. Patent Publication 20140005190; Park et al., Cancer Res. 73:5485-96 (2013); Wang et al., Proc. Natl. Acad. Sci USA 97:7124-9 (2000); Zhang et al., Anal. Biochem. 307: 70-5 (2002); Bruncko et al., J. Med. Chem. 50:641-62 (2007)). Percent inhibition may be determined by the equation: $1-[(mP$ value of well-negative control)/range)]×100%. Inhibitory constant (Ki) value is determined by the formula: $Ki=[I]50/([L]50/Kd+[P]0/Kd+1)$ as described in Bruncko et al., J. Med. Chem. 50:641-62 (2007) (see, also, Wang, FEBS Lett. 360:111-114 (1995)).

Agents (e.g., Bcl-xL selective inhibitors, Bcl-xL/Bcl-2 inhibitors, Bcl-xL/Bcl-2/Bcl-w inhibitors, Bcl-xL/Bcl-w inhibitors) used in the methods described herein that selectively kill senescent cells include, by way of example, a small molecule.

In particular embodiments, the Bcl-xL inhibitor is a small molecule compound that belongs to any one of the following classes of compounds, for example, a benzothiazole-hydrazone compound, aminopyridine compound, benzimidazole compound, tetrahydroquinoline compound, and phenoxyl compound and related analogs.

In one embodiment, a Bcl-xL selective inhibitor useful for the methods described herein is a benzothiazole-hydrazone small molecule inhibitor. Benzothiazole-hydrazone compounds include WEHI-539 (5-[3-[4-(aminomethyl)phenoxy]propyl]-2-[(8E)-8-(1,3-benzothiazol-2-ylhydrazinylidene)-6,7-dihydro-5H-naphthalen-2-yl]-1,3-thiazole-4-carboxylic acid), a BH3 peptide mimetic that selectively targets Bcl-xL (see, e.g., Lessene et al., Nature Chemical Biology 9:390-397 (2013)). In certain embodiments, the methods described herein comprise use of WEHI-539 for selectively killing senescent cells.

In other embodiments, the Bcl-xL selective inhibitor is an aminopyridine compound. An aminopyridine compound that may be used as a selective Bcl-xL inhibitor is BXI-61 (3-[(9-amino-7-ethoxyacridin-3-yl)diazenyl]pyridine-2,6-diamine) (see, e.g., Park et al., Cancer Res. 73:5485-96 (2013); U.S. Patent Publ. No. 2009-0118135). In certain embodiments, the methods described herein comprise use of BXI-61 for selectively killing senescent cells.

In still other embodiments, the Bcl-xL selective inhibitor that may be used in the methods described herein is a benzimidazole compound. An example of a benzimidazole compound that may be used as a selective Bcl-XL inhibitor is BXI-72 (2'-(4-Hydroxyphenyl)-5-(4-methyl-1-piperazinyl)-2,5'-bi(1H-benzimidazole) trihydrochloride) (see, e.g., Park et al., supra). In certain embodiments, the methods described herein comprise use of BXI-72 for selectively killing senescent cells.

In yet another embodiment, the Bcl-xL selective inhibitor is a tetrahydroquinoline compound (see, e.g., U.S. Patent Publ. No. 2014-0005190). Examples of tetrahydroquinoline compounds that may be used as selective Bcl-xL inhibitors are shown in Table 1 of U.S. Patent Publ. No. 2014-0005190 and described therein. Other inhibitors described therein may inhibit other Bcl-2 family members (e.g., Bcl-2) in addition to Bcl-xL.

In other embodiments, a Bcl-xL selective inhibitor is a phenoxyl compound. An example of a phenoxyl compound that may be used as a selective Bcl-xL inhibitor is 2[[3-(2, 3-dichlorophenoxy) propyl]amino]ethanol (2,3-DCPE) (see, Wu et al., Cancer Res. 64:1110-1113 (2004)). In certain embodiments, the methods described herein comprise use of 2,3-DCPE for selectively killing senescent cells.

In still another embodiment, an inhibitor of a Bcl-2 anti-apoptotic family member that inhibits at least Bcl-xL is described in U.S. Pat. No. 8,232,273. In a particular embodiment, the inhibitor is a Bcl-xL selective inhibitor called A-1155463 (see, e.g., Tao et al., *ACS Med. Chem. Lett.*, 2014, 5(10): 1088-1093).

In other embodiments, a senolytic agent of interest inhibits other Bcl-2 anti-apoptotic family members in addition to Bcl-xL. For example, methods described herein comprise use of Bcl-xL/Bcl-2 inhibitors, Bcl-xL/Bcl-2/Bcl-w inhibitors, and Bcl-xL/Bcl-w inhibitors and analogs thereof. In certain embodiments, the inhibitors include compounds that inhibit Bcl-2 and Bcl-xL, which inhibitors may also inhibit Bcl-w. Examples of these inhibitors include ABT-263 (4-[4-[[2-(4-chlorophenyl)-5,5-dimethylcyclohexen-1-yl]methyl]piperazin-1-yl]-N-[4-[[(2R)-4-morpholin-4-yl-1-phenylsulfanylbutan-2-yl]amino]-3-(trifluoromethylsulfonyl)phenyl]sulfonylbenzamide or IUPAC, (R)-4-(4-((4'-chloro-4,4-dimethyl-3,4,5,6-tetrahydro-[1,1'-biphenyl]-2-yl)methyl)piperazin-1-yl)-N-((4-((4-morpholino-1-(phenylthio)butan-2-yl)amino)-3-((trifluoromethyl)sulfonyl)phenyl)sulfonyl)benzamide) (see, e.g., Park et al., 2008, J. Med. Chem. 51:6902; Tse et al., Cancer Res., 2008, 68:3421; Int'l Patent Appl. Pub. No. WO 2009/155386; U.S. Pat. Nos. 7,390,799, 7,709,467, 7,906,505, 8,624,027) and ABT-737 (4-[4-[(4'-Chloro[1,1'-biphenyl]-2-yl)methyl]-1-piperazinyl]-N-[[4-[[[(1R)-3-(dimethylamino)-1-[(phenylthio)methyl]propyl]amino]-3-nitrophenyl]sulfonyl]benzamide, 4-[4-[(4'-chloro[1,1'-biphenyl]-2-yl)methyl]-1-piperazinyl]-N-[[4-[[[(1R)-3-(dimethylamino)-1-[(phenylthio)methyl]propyl]amino]-3-nitrophenyl]sulfonyl]- or 4-[4-[[2-(4-chlorophenyl)phenyl]methyl]piperazin-1-yl]-N-[4-[[(2R)-4-(dimethylamino)-1-phenylsulfanylbutan-2-yl]amino]-3-nitrophenyl]sulfonylbenzamide) (see, e.g., Oltersdorf et al., Nature, 2005, 435:677; U.S. Pat. No. 7,973,161; U.S. Pat. No. 7,642,260). In other embodiments, the Bcl-2 antiapoptotic protein inhibitor is a quinazoline sulfonamide compound (see, e.g., Sleebs et al., 2011, J. Med. Chem. 54:1914). In still another embodiment, the Bcl-2 anti-apoptotic protein inhibitor is a small molecule compound as described in Zhou et al., J. Med. Chem., 2012, 55:4664 (see, e.g., Compound 21 (R)-4-(4-chlorophenyl)-3-(3-(4-(4-(4-((4-(dimethylthio)-1-(phenylthio)butan-2-yl)amino)-3-nitrophenylsulfonamido)phenyl)piperazin-1-yl)phenyl)-5-ethyl-1-methyl-1H-pyrrole-2-carboxylic acid) and Zhou et al., J. Med. Chem., 2012, 55:6149 (see, e.g., Compound 14 (R)-5-(4-Chlorophenyl)-4-(3-(4-(4-(4-((4-(dimethylamino)-1-(phenylthio)butan-2-yl)amino)-3-nitrophenylsulfonamido)phenyl)piperazin-1-yl)phenyl)-1-ethyl-2-methyl-1H-pyrrole-3-carboxylic acid; Compound 15 (R)-5-(4-Chlorophenyl)-4-(3-(4-(4-(4-((4-(dimethylamino)-1-(phenylthio)butan-2-yl)amino)-3-nitrophenylsulfonamido)phenyl)piperazin-1-yl)phenyl)-1-isopropyl-2-methyl-1H-pyrrole-3-carboxylic acid). In other embodiments, the Bcl-2 anti-apoptotic protein inhibitor is a Bcl-2/Bcl-xL inhibitor such as BM-1074 (see, e.g., Aguilar et al., 2013, J. Med. Chem. 56:3048); BM-957 (see, e.g., Chen et al., 2012, J. Med. Chem. 55:8502); BM-1197 (see, e.g., Bai et al., PLoS One 2014 Jun. 5; 9(6):e99404. Doi: 10.1371/journal.pone. 009904); U.S. Patent Appl. No. 2014/0199234; N-acylsufonamide compounds (see, e.g., Int'l Patent Appl. Pub. No. WO 2002/024636, Int'l Patent Appl. Pub. No. WO 2005/049593, Int'l Patent Appl. Pub. No. WO 2005/049594, U.S. Pat. No. 7,767,684, U.S. Pat. No. 7,906,505). In still another embodiment, the Bcl-2 anti-apoptotic protein inhibitor is a small molecule macrocyclic compound (see, e.g., Intl Patent Appl. Pub. No. WO 2006/127364, U.S. Pat. No. 7,777,076). In yet another embodiment, the Bcl-2 anti-apoptotic protein inhibitor is an isoxazolidine compound (see, e.g., Int'l Patent Appl. Pub. No. WO 2008/060569, U.S. Pat. No. 7,851,637, U.S. Pat. No. 7,842,815).

In certain embodiments, the senolytic agent is a compound that is an inhibitor of Bcl-2, Bcl-w, and Bcl-xL, such as ABT-263 or ABT-737. In certain specific embodiments, the senolytic agent is a compound or a pharmaceutically acceptable salt, stereoisomer, tautomer, or prodrug thereof as illustrated below, which depicts the structure of ABT-263 (Navitoclax)

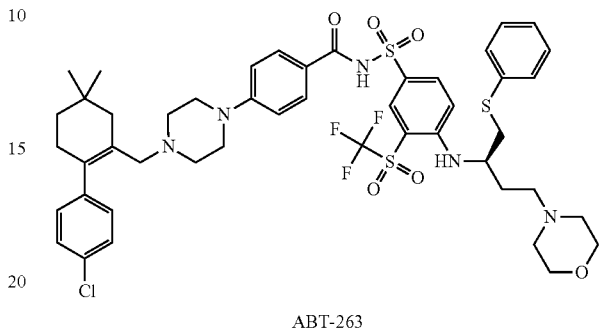

ABT-263

Akt Kinase Inhibitors

In certain embodiments the senolytic agent is an Akt Kinase inhibitor. For example, a senolytic agent can be a small molecule compound and analogs thereof that inhibits Akt. In some embodiments, the senolytic agent is a compound that selectively inhibits Akt1, Akt2, and Akt3, relative to other protein kinases.

Akt inhibitors (which may also be called Akt kinase inhibitors or AKT kinase inhibitors) can be divided into six major classes based on their mechanisms of action (see, e.g., Bhutani et al., *Infectious Agents and Cancer* 2013, 8:49 doi:10.1186/1750-9378-8-49). Akt is also called protein kinase B (PKB) in the art. The first class contains ATP competitive inhibitors of Akt and includes compounds such as CCT128930 and GDC-0068, which inhibit Akt2 and Akt1. This category also includes the pan-Akt kinase inhibitors such as GSK2110183 (afuresertib), GSK690693, and AT7867. The second class contains lipid-based Akt inhibitors that act by inhibiting the generation of PIP3 by PI3K. This mechanism is employed by phosphatidylinositol analogs such as Calbiochem Akt Inhibitors I, II and III or other PI3K inhibitors such as PX-866. This category also includes compounds such as Perifosine (KRX-0401) (Aeterna Zentaris/Keryx). The third class contains a group of compounds called pseudosubstrate inhibitors. These include compounds such as AKTide-2 T and FOXO3 hybrid. The fourth class consists of allosteric inhibitors of AKT kinase domain, and include compounds such as MK-2206 (8-[4-(1-aminocyclobutyl)phenyl]-9-phenyl-2H-[1,2,4]triazolo[3,4-f][1,6]naphthyridin-3-one;dihydrochloride) (Merck & Co.) (see, e.g., U.S. Pat. No. 7,576,209). The fifth class consists of antibodies and include molecules such as GST-anti-Akt1-MTS. The last class comprises compounds that interact with the PH domain of Akt, and includes Triciribine and PX-316. Other compounds described in the art that act as AKT inhibitors include, for example, GSK-2141795 (GlaxoSmithKline), VQD-002, miltefosine, AZD5363, GDC-0068, and API-1.

In a specific embodiment, the senolytic agent is a compound that is an Akt kinase inhibitor, which has the structure as shown below (also called MK-2206 herein and in the art), 8-[4-(1-aminocyclobutyl)phenyl]-9-phenyl-2H-[1,2,4]triazolo[3,4-f][1,6]naphthyridin-3-one); or a pharmaceutically acceptable salt, stereoisomer, tautomer, or prodrug thereof. The dihydrochloride salt is shown.

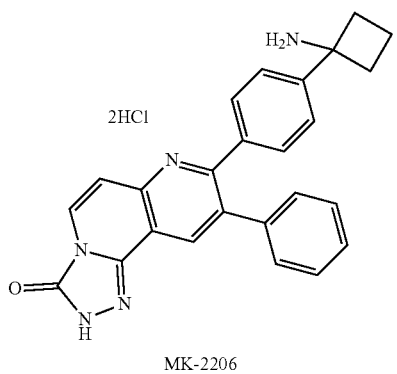 [SMILES: NC1(c2ccc(-c3nc4ccn5c(=O)[nH]nc5c4cc3-c3ccccc3)cc2)CCC1]

MK-2206

In certain embodiments, at least one senolytic agent may be administered with at least one other senolytic agent, which two or more senolytic agents act additively or synergistically to selectively kill senescent cells. In particular embodiments, methods are provided for using a senolytic agent wherein the senolytic agent alters either a cell survival signaling pathway or an inflammatory pathway or alters both the cell survival signaling pathway and the inflammatory pathway in a senescent cell. In other particular embodiments, methods comprise use of at least two senolytic agents wherein at least one senolytic agent and a second senolytic agent are each different and independently alter either one or both of a survival signaling pathway and an inflammatory pathway in a senescent cell. For convenience, when two or more senolytic agents are described herein as being used in combination, one senolytic agent will be called a first senolytic agent, another senolytic agent will be called the second senolytic agent, etc. In other certain embodiments, the methods described herein comprise administering at least three senolytic agents (a first senolytic agent, second senolytic agent, and third senolytic agent). The adjectives, first, second, third, and such, in this context are used for convenience only and are not to be construed as describing order or administration, preference, or level of senolytic activity or other parameter unless expressly described otherwise. In particular embodiments, when two or more senolytic agents are used in the methods described herein, each senolytic agent is a small molecule. In other certain embodiments, the methods described herein comprise administering at least three senolytic agents (a first senolytic agent, second senolytic agent, and third senolytic agent).

Salts and General Synthesis Procedures.

The small molecule compounds described herein as senolytic agents include physiologically acceptable salts (i.e., pharmaceutically acceptable salts), hydrates, solvates, polymorphs, metabolites, and prodrugs of the senolytic agents. Further information on metabolism may be obtained from The Pharmacological Basis of Therapeutics, 9th Edition, McGraw-Hill (1996). Metabolites of the compounds disclosed herein can be identified either by administration of compounds to a host and analysis of tissue samples from the host, or by incubation of compounds with hepatic cells in vitro and analysis of the resulting compounds. Both methods are well known in the art.

Compounds may sometimes be depicted as an anionic species. One of ordinary skill in the art will recognize that the compounds exist with an equimolar ratio of cation. For instance, the compounds described herein can exist in the fully protonated form, or in the form of a salt such as sodium, potassium, ammonium or in combination with any inorganic base as described above. When more than one anionic species is depicted, each anionic species may independently exist as either the protonated species or as the salt species. In some specific embodiments, the compounds described herein exist as the sodium salt. In other specific embodiments, the compounds described herein exist as the potassium salt.

Furthermore, some of the crystalline forms of any compound described herein may exist as polymorphs, which are also included and contemplated by the present disclosure. In addition, some of the compounds may form solvates with water or other organic solvents. Often crystallizations produce a solvate of the disclosed compounds. As used herein, the term "solvate" refers to an aggregate that comprises one or more molecules of any of the disclosed compounds with one or more molecules of solvent. The solvent may be water, in which case the solvate may be a hydrate. Alternatively, the solvent may be an organic solvent. Thus, the presently disclosed compounds may exist as a hydrate, including a monohydrate, dihydrate, hemihydrate, sesquihydrate, trihydrate, tetrahydrate and the like, as well as the corresponding solvated forms. Certain embodiments of the compounds may be true solvates, while in other instances, some embodiments of the compounds may merely retain adventitious water or be a mixture of water plus some adventitious solvent.

In general, the compounds used in the methods described herein may be made according to organic synthesis techniques known to those skilled in this art, starting from commercially available chemicals and/or from compounds described in the chemical literature. Specific and analogous reactants may also be identified through the indices of known chemicals prepared by the Chemical Abstract Service of the American Chemical Society, which are available in most public and university libraries, as well as through on-line databases (the American Chemical Society, Washington, D.C., may be contacted for more details). Chemicals that are known but not commercially available in catalogs may be prepared by custom chemical synthesis houses, where many of the standard chemical supply houses (e.g., those listed above) provide custom synthesis services. A reference for the preparation and selection of pharmaceutical salts of the present disclosure is P. H. Stahl & C. G. Wermuth "Handbook of Pharmaceutical Salts," Verlag Helvetica Chimica Acta, Zurich, 2002. Methods known to one of ordinary skill in the art may be identified through various reference books and databases. Suitable reference books and treatises detail the synthesis of reactants useful in the preparation of compounds described herein, or provide references to articles that describe the preparation.

Assays and techniques for identifying senolytic agents are described in greater detail herein. In addition, identifying and selecting small compounds as senolytic agents, a person skilled in the medicinal chemistry art may also consider other properties of the small molecule, such as solubility, bioavailability, pharmacokinetics, Lipinski Rule of 5, and the like.

Polypeptides, Antibodies, and Nucleic Acids

In other certain embodiments, a senolytic agent may be a polypeptide, peptide, antibody, antigen-binding fragment (i.e., peptides and polypeptides comprising at least one complementary determining region (CDR)), peptibody, recombinant viral vector, or a nucleic acid. In certain embodiments, a senolytic agent is an antisense oligonucleotide, siRNA, shRNA, or a peptide. For example, senolytic agents such as polypeptides, antibodies, nucleic acids, and the like, include, for example, MDM2 inhibitors, Bcl-2 family inhibitors, or Akt kinase inhibitors. In other embodiments, polypeptides, peptides, antibodies (including antigen-binding fragments thereof) that specifically bind to a ligand or target protein of a small molecule

EXAMPLES

Example 1

Determining Senolytic Activity of Nutlin-3a

Figure 16:
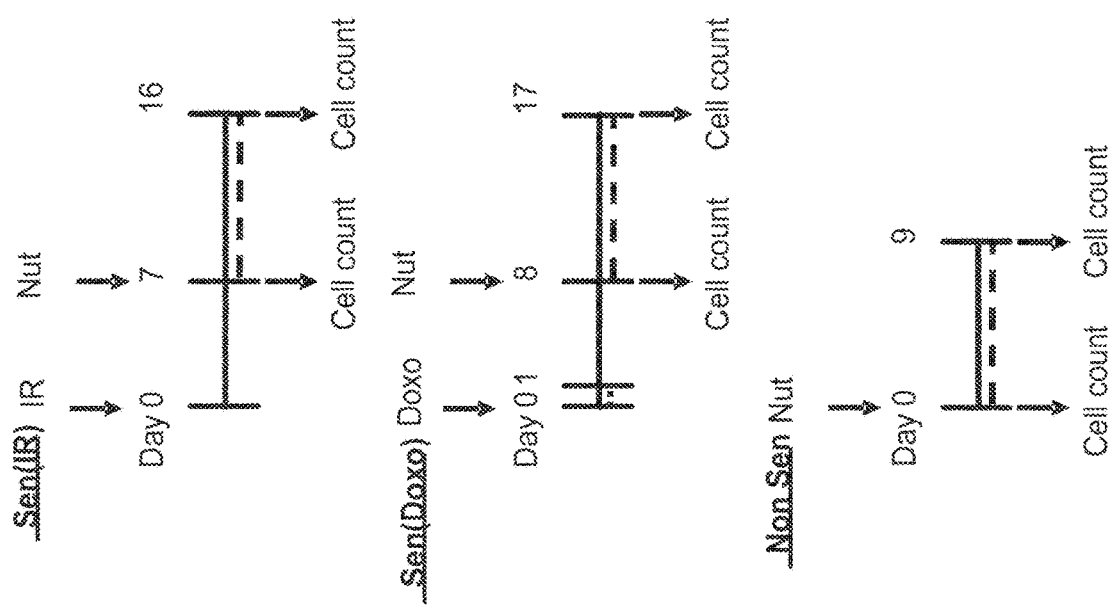
FIG. 16 provides a schematic of general timelines and procedures for treatment with Nutlin-3a (Nut) of (1) cells induced to senesce by irradiation (Sen(IR)); (2) cells induced to senesce by treatment with doxorubicin (Sen (Doxo)); and (3) non-senescent cells (Non Sen).
Figures 17A, 17B, 17C, 17D:
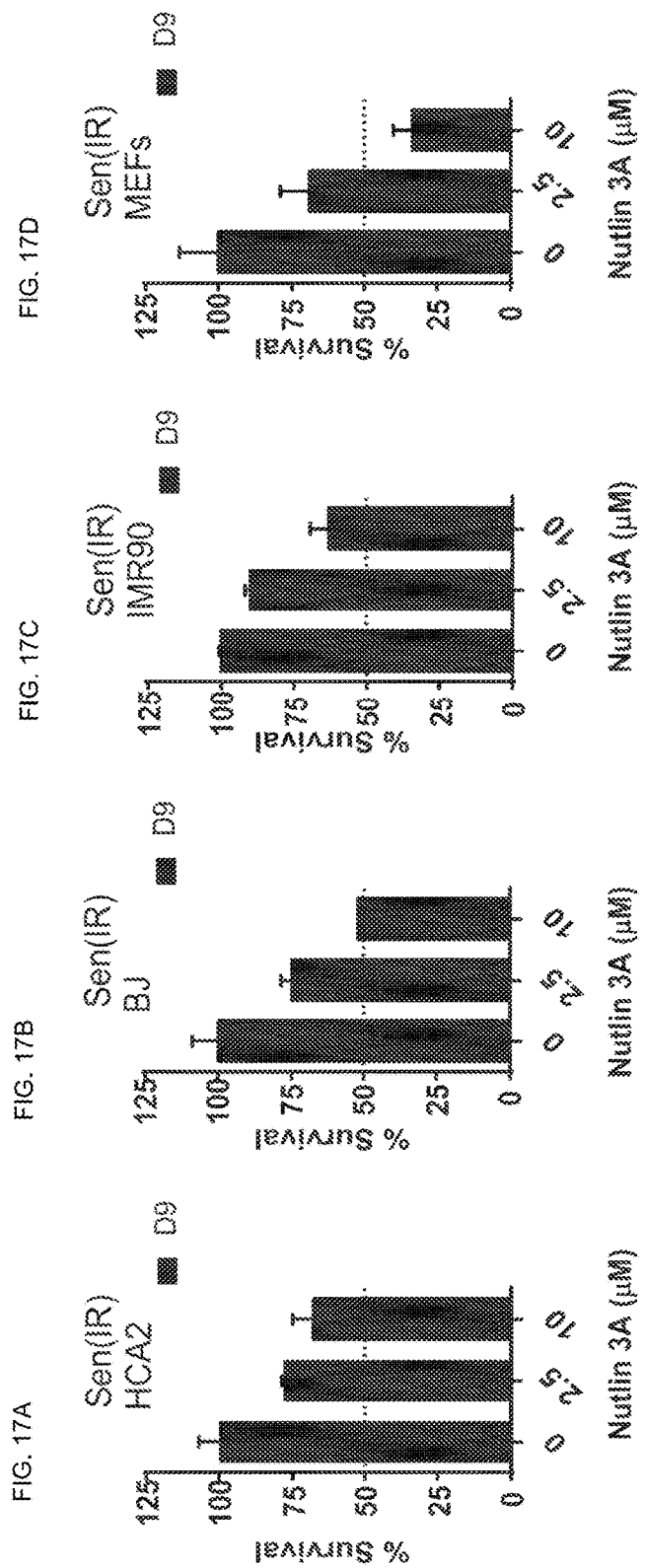
FIG. 17A-D show the effect of Nutlin-3a on survival of fibroblasts induced to senesce by irradiation.

Foreskin fibroblast cell lines HCA2 and BJ, lung fibroblast cell line IMR90, and mouse embryonic fibroblasts were seeded in six-well plates and induced to senesce with 10 Gy of ionizing radiation (IR) or a 24 hr treatment with doxorubicin (Doxo). Senescent phenotype was allowed to develop for at least 7 days, at which point a cell count was made to determine the baseline number of cells. Nutlin-3a treatment was then initiated for a period of at least 9 days. Media alone or media with drug as appropriate was refreshed at least every three days. At the end of the assay time period, cells are counted. Each condition was seeded in three plate wells and counted independently. Initial cell count serves as a control to determine the induction of senescence, as compared to the last day count without nutlin treatment. Initial non-senescent cell count serves as a proxy to determine Nutlin-3a toxicity. FIG. 16 shows a schematic of the experiment design.

Foreskin fibroblast cell lines HCA2 and BJ, lung fibroblast cell line IMR90, and mouse embryonic fibroblasts were exposed to 10 Gy of ionizing radiation (IR) to induce senescence. Seven days following irradiation, the cell were treated with varying concentrations of Nutlin-3a (0, 2.5 µM, and 10 µM) for a period of 9 days, with the drug refreshed at least every 3 days. Percent survival was calculated as [cell count on day 9 of Nutlin-3a treatment/initial cell count on first day of Nutlin-3a treatment]. The results are shown in FIGS. 17A-D, which show that Nutlin-3a reduced cell survival of senescent foreskin fibroblasts (HCA2 and BJ), lung fibroblasts (IMR90), and mouse embryonic fibroblasts (MEF), indicating Nutlin-3a is a senolytic agent.

Figure 18A:
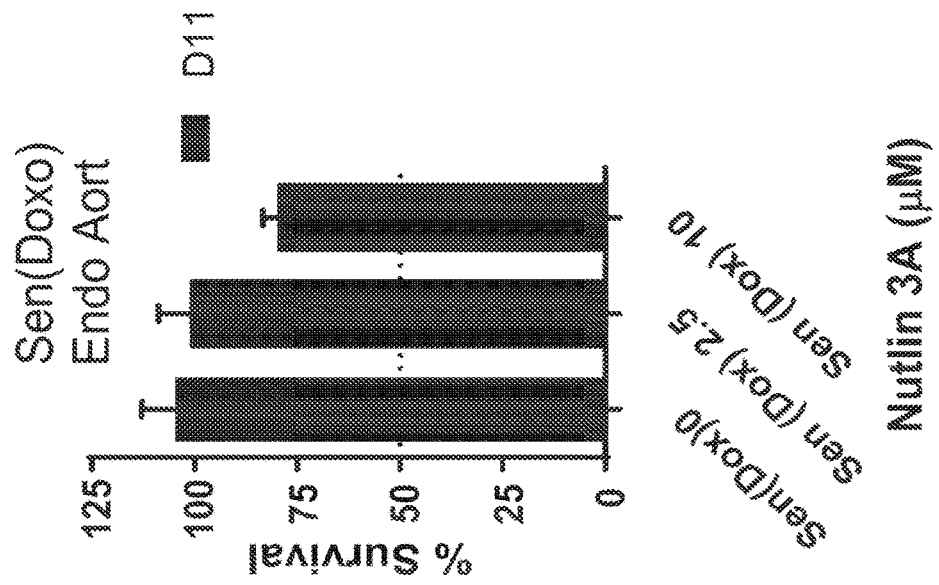
FIG. 18A-B illustrate the effect of Nutlin-3a on survival of cells induced to senesce by treatment with doxorubicin. HCA2 cells were treated with Nutlin-3a for 9 days (D9), and aortic endothelial cells were treated with Nutlin-3a for 11 days (D11), and then percent survival was determined.
Figure 18B:
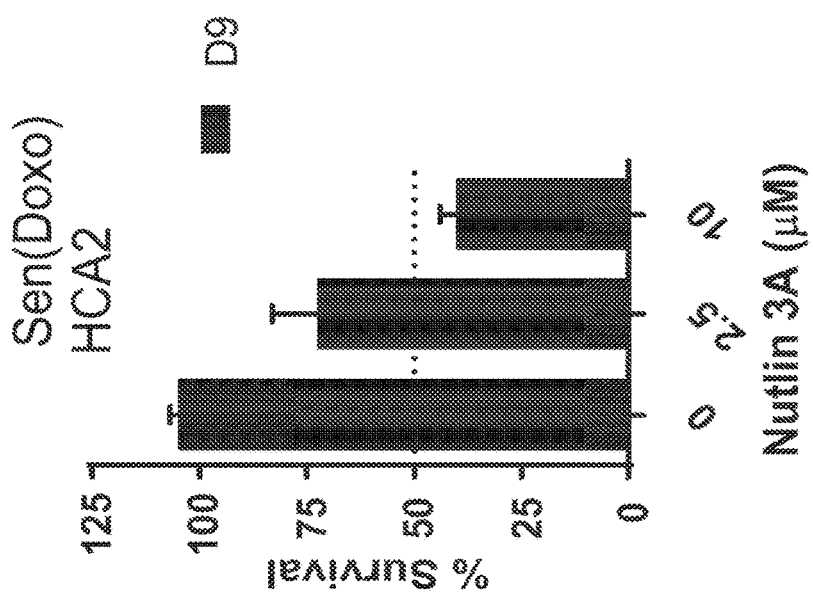

Foreskin fibroblasts (HCA2) and aortic endothelial cells (Endo Aort) were treated with doxorubicin (250 nM) for one day (24 hours) to induce senescence (see FIG. 16). Eight days following doxorubicin treatment, Nutlin-3a treatment was initiated. HCA2 cells were exposed to Nutlin-3a for 9 days, and aortic endothelial cells were exposed to Nutlin-3a for 11 days. Media containing the compound or control media was refreshed at least every 3 days. Percent survival was calculated as [cell count on the last day of Nutlin-3a treatment/initial cell count on first day of Nutlin-3a treatment]. The results are shown in FIGS. 18A-B, which show that doxorubicin-induced senescent cells are sensitive to Nutlin-3a.

Non-senescent foreskin fibroblasts (HCA2), lung fibroblasts (IMR90), and mouse embryonic fibroblasts (MEF) were treated with varying concentrations (0, 2.5 µM, and 10 µM) of Nutlin-3a for a period of 9 days to assess Nutlin-3a toxicity. Cell counts were taken at the start (NS start) and end of Nutlin-3a treatment. The difference between counts of cells not treated with Nutlin-3a on day 9 (NS 0) and cell counts determined at day zero (NS start) reflects the cell growth over the indicated time period. The results are shown in FIGS. 19A-C, which show that Nutlin-3a treatment reduces proliferation but is non-toxic to non-senescent cells. Nutlin-3a treatment did not decrease the number of cells below the starting level, indicating an absence of toxicity. Decrease in apparent survival between NS 0 and NS 2.5 and between NS 0 and NS 10 reflects a decrease in cell growth. Without wishing to be bound by theory, Nutlin-3a may stabilize p53, leading to cell cycle growth arrest.

Figure 20B:
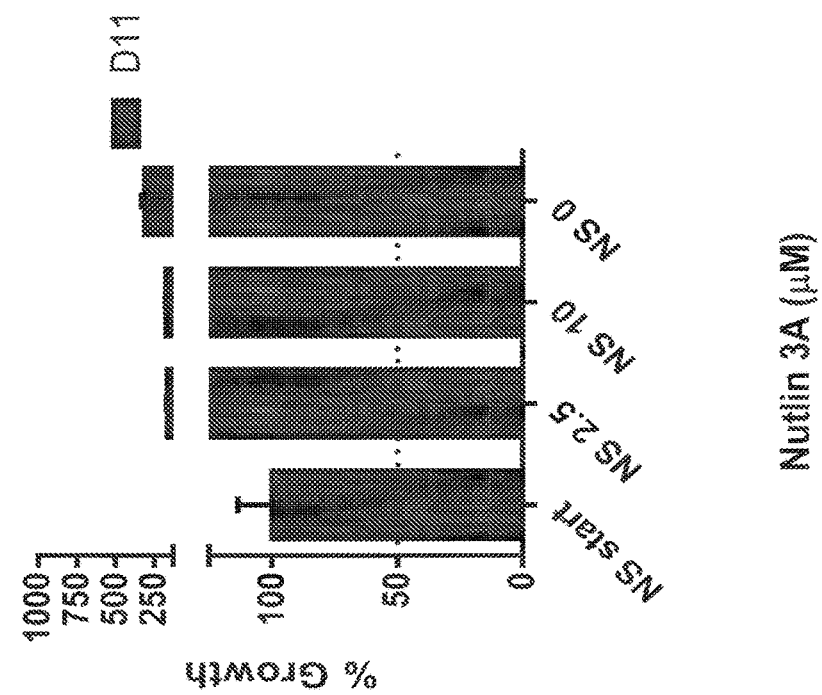
FIGS. 20A-B illustrate percent growth of non-senescent aortic endothelial cells and non-senescent pre-adipocytes treated with Nutlin-3a. Cells were treated with Nutlin-3a for 11 days and percent growth determined (D11).
Figure 20A:
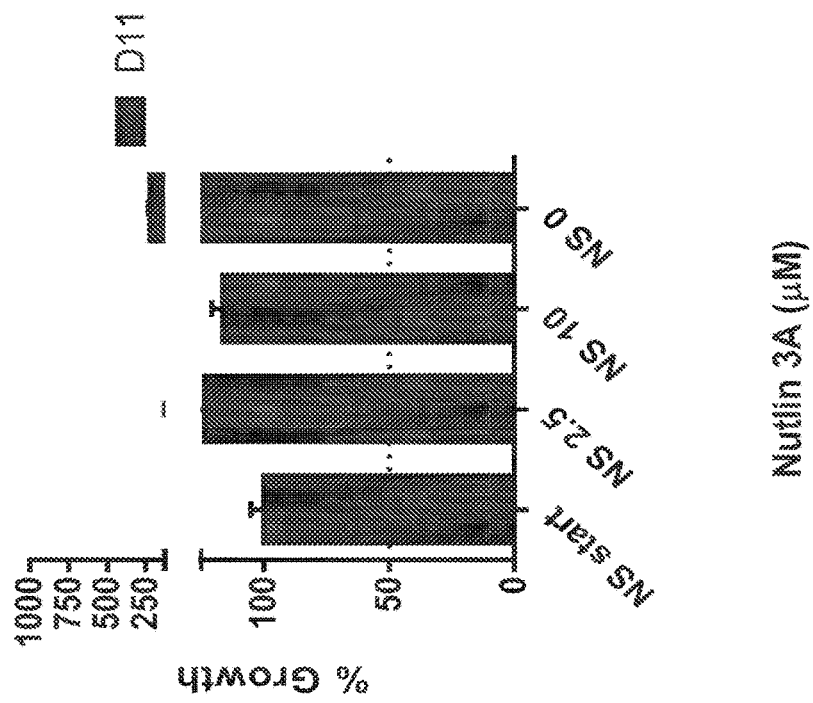
Figures 23A, 23B, 23C, 23D:
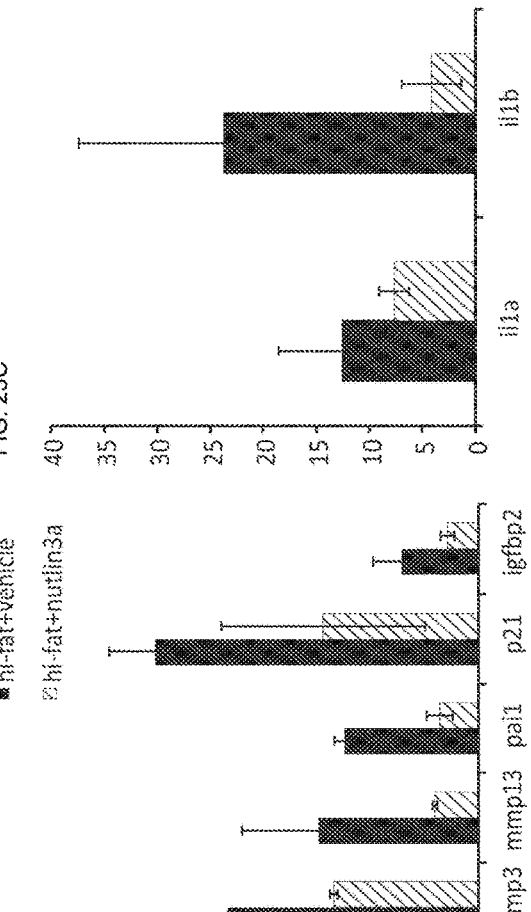
FIGS. 23A-D illustrate RT-PCR analysis of SASP factors and senescence markers in aortic arches of LDLR−/− mice fed a HFD after one treatment cycle of Nutlin-3A or vehicle.

Non-senescent aortic endothelial (Endo Aort) cells and pre-adipocytes (Pread) were also treated with varying concentrations (0, 2.5 µM, and 10 µM) of Nutlin-3a for a period of 11 days to assess Nutlin-3a toxicity, as described above. Cell counts were taken at the start at Day 0 (NS start) and at the end of Nutlin-3a treatment (NS 0). The difference between counts of cells not treated with Nutlin-3a on day 11 (NS 0) and cell counts from NS start reflects the cell growth over the indicated time period. The results are shown in FIGS. 20A-B, illustrating that Nutlin-3a treatment reduces proliferation but is non-toxic to non-senescent cells. As observed with fibroblasts, Nutlin-3a treatment does not decrease the number of cells below the starting level, indicating an absence of toxicity. Decrease in apparent survival between NS 0 and NS 2.5 and between NS 0 and NS 10 reflects a decrease in cell growth.

Example 2

Effect of Removal of Senescent Cells in Animal Models of Atherosclerosis

Schematics of two atherosclerosis mouse models are presented in FIGS. 21A-B. The study illustrated in FIG. 21A assessed the extent to which clearance of senescent cells from plaques in LDLR-/- mice with Nutlin-3A reduces plaque load. Two groups of LDLR-/- mice (10 weeks) are fed a high fat diet (HFD) (Harlan Teklad TD.88137) having 42% calories from fat, beginning at Week 0 and throughout the study. Two groups of LDLR-/- mice (10 weeks) are fed normal chow (-HFD). From weeks 0-2, one group of HFD mice and HFD mice are treated with Nutlin-3A (25 mg/kg, intraperitoneally). One treatment cycle is 14 days treatment, 14 days off. Vehicle is administered to one group of HFD mice and one group of HFD mice. At week 4 (time point 1), one group of mice are sacrificed and to assess presence of senescent cells in the plaques. For the some of the remaining mice, Nutlin-3A and vehicle administration is repeated from weeks 4-6. At week 8 (time point 2), the mice are sacrificed and to assess presence of senescent cells in the plaques. The remaining mice are treated with Nutlin-3A or vehicle from weeks 8-10. At week 12 (time point 3), the mice are sacrificed and to assess the level of plaque and the number of senescent cells in the plaques.

Plasma lipid levels were measured in LDLR-/- mice fed a HFD and treated with Nutlin-3A or vehicle at time point 1 as compared with mice fed a -HFD (n=3 per group). Plasma was collected mid-afternoon and analyzed for circulating lipids and lipoproteins. The data are shown in FIGS. 22A-D.

At the end of time point 1, LDLR-/- mice fed a HFD and treated with Nutlin-3A or vehicle were sacrificed (n=3, all groups), and the aortic arches were dissected for RT-PCR analysis of SASP factors and senescent cell markers. Values were normalized to GAPDH and expressed as fold-change versus age-matched, vehicle-treated LDLR-/- mice on a normal diet. The data show that clearance of senescent cells with Nutlin-3A in LDLR-/- mice fed a HFD reduced expression of several SASP factors and senescent cell markers, MMP3, MMP13, PAIL, p21, IGFBP2, IL-1A, and IL-1B after 1 treatment cycle (see FIGS. 23A-D).

At the end of time point 2, LDLR−/− mice fed a HFD and treated with Nutlin-3A or vehicle (n=3 for all groups) were sacrificed, and aortic arches were dissected for RT-PCR analysis of SASP factors and senescent cell markers. Values were normalized to GAPDH and expressed as fold-change versus age-matched, vehicle-treated LDLR−/− mice on a normal diet. The data show expression of some SASP factors and senescent cell markers in the aortic arch within HFD mice (FIGS. 24A-C). Clearance of senescent cells with multiple treatment cycles of Nutlin-3A in LDLR−/− mice fed a HFD reduced expression of most markers (FIGS. 24A-B).

Figure 26A:
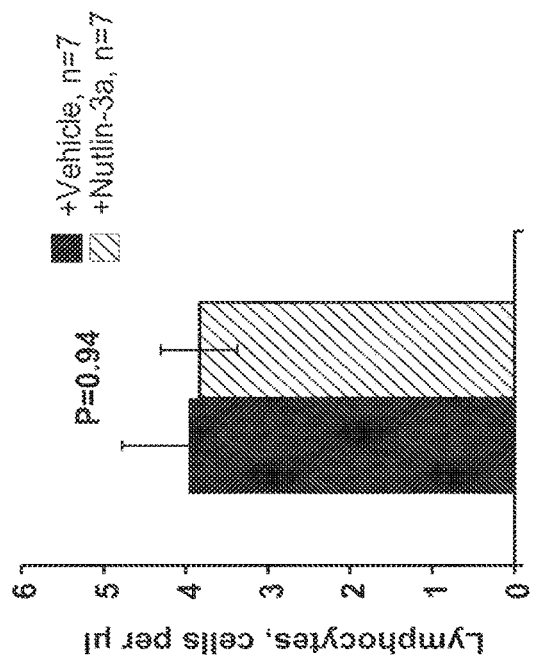
FIGS. 26A-B depict plots of platelet (FIG. 26A) and lymphocyte counts (FIG. 26B) from LDLR$^{-/-}$ mice fed a HFD after three treatment cycles of Nutlin-3A or vehicle.
Figure 26B:
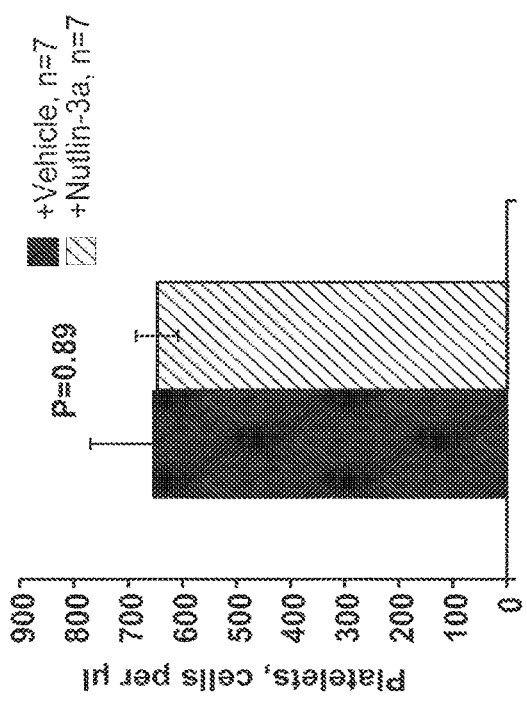
Figure 27A:
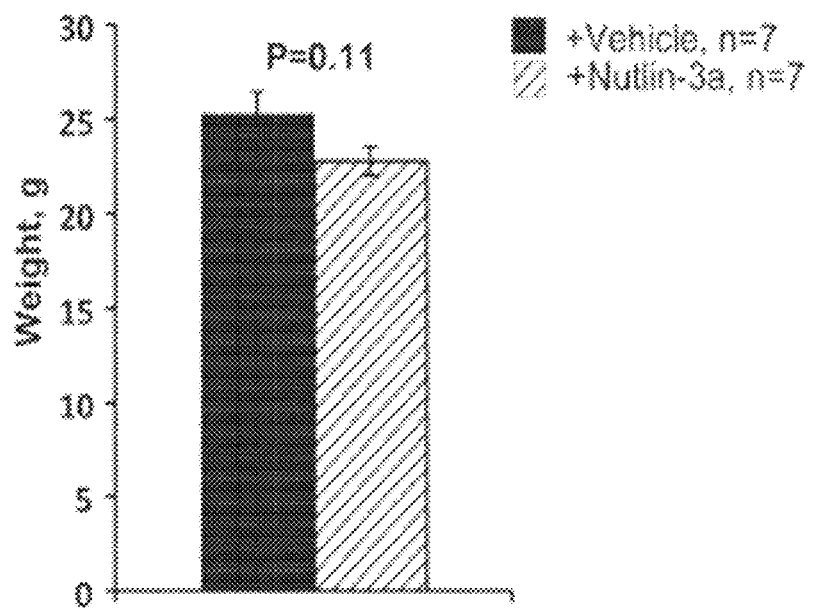
FIGS. 27A-B depict plots of weight and body fat/lean tissue composition (%), respectively, of LDLR−/− mice fed a HFD after three treatment cycles of Nutlin-3A or vehicle.
Figure 27B:
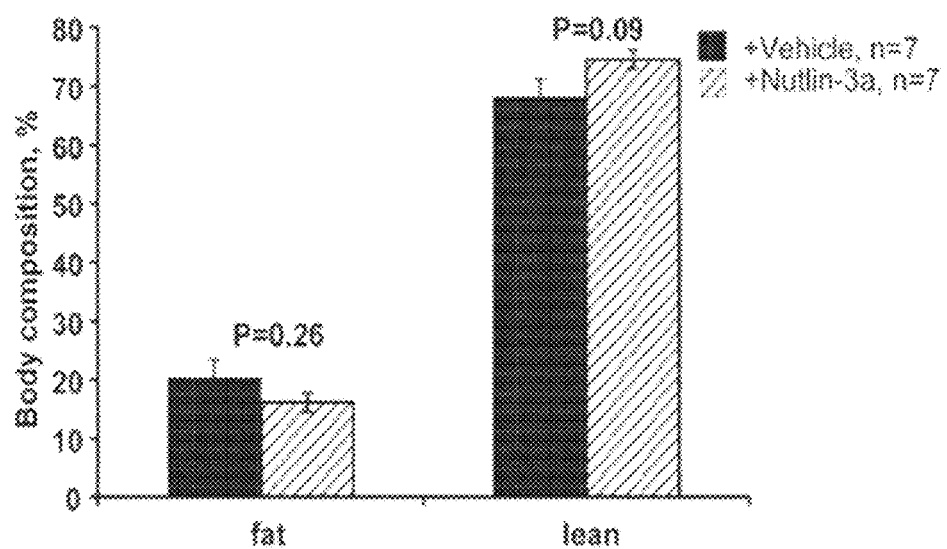

At the end of time point 3, LDLR−/− mice fed a HFD and treated with Nutlin-3A or vehicle (n=3 for all groups) were sacrificed, and aortas were dissected and stained with Sudan IV to detect the presence of lipid. Body composition of the mice was analyzed by MRI, and circulating blood cells were counted by Hemavet. The data show that treatment with Nutlin-3A reduces plaques in the descending aorta by ~45% (FIGS. 25A-C). As shown in FIGS. 26A-B, the platelet and lymphocyte counts were equivalent between the Nutlin-3A and vehicle treated mice. As shown in FIGS. 27A-B, treatment with Nutlin-3A also decreased mass and body fat composition in mice fed a HFD.

Figure 28:
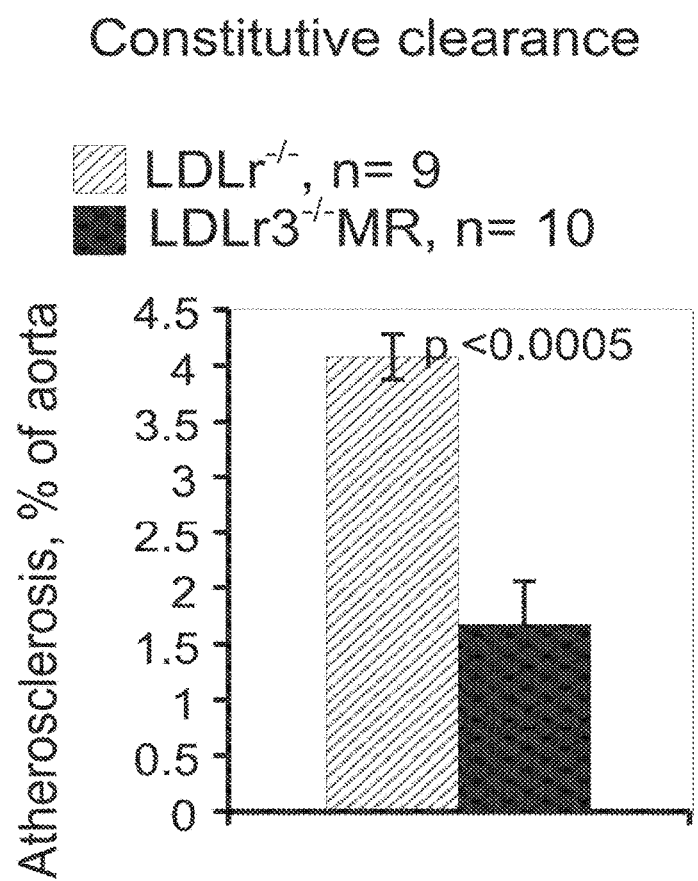
FIG. 28 depicts a graph of the effect of clearance of senescent cells with ganciclovir in LDLR−/− and LDLR−/−/3MR mice fed a HFD, as measured by the % of the aorta covered in plaques.
Figure 29:
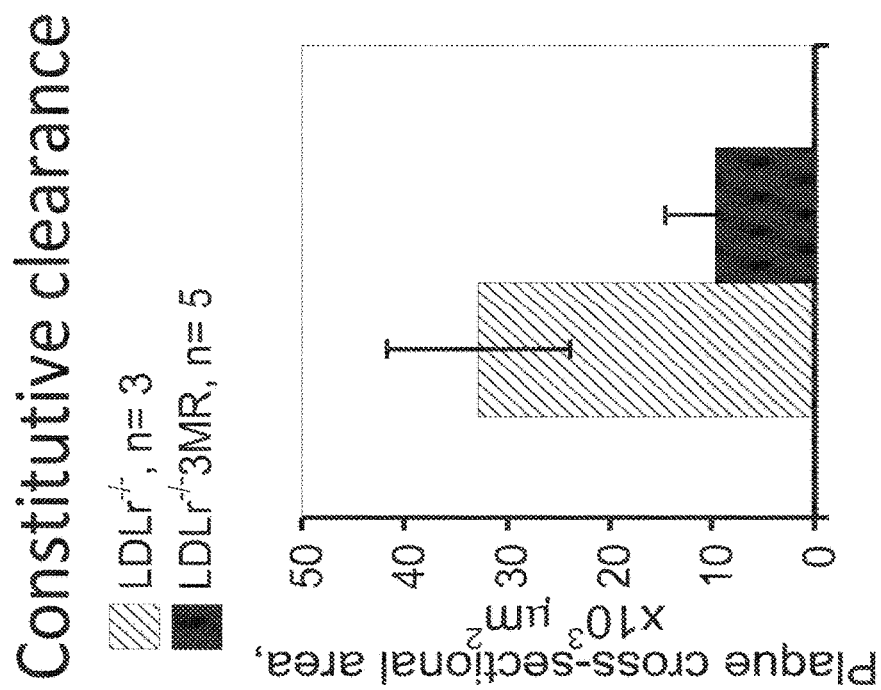
FIG. 29 depicts a graph of the effect of clearance of senescent cells with ganciclovir in LDLR−/− and LDLR−/−/3MR mice fed a HFD, as measured by the plaque cross-sectional area of the aorta.

The study illustrated in FIG. 21B assessed the extent to which acyclovir based clearance of senescent cells from LDLR−/−/3MR double transgenic mice improves pre-existing atherogenic disease. LDLR−/−/3MR double transgenic mice (10 weeks) and LDLR−/− single transgenic mice (10 weeks) are fed a high fat diet beginning at Week 0 until Week 12. Gancyclovir is administered to both groups of mice (25 mg/kg intraperitoneally) from weeks 12-13 and weeks 14-15. At week 16, the level of plaque and the number of senescent cells in the plaques are determined. As shown in FIG. 28, clearance of senescent cells with GCV in LDLR−/−/3MR double transgenic mice fed a HFD (n=10) reduces the % of the aorta covered with plaque as compared to LDLR−/− mice/HFD controls (n=9). As shown in FIG. 29, clearance of senescent cells with GCV also reduced the plaque cross-sectional area in in LDLR−/−/3MR double transgenic mice fed a HFD (n=3) as compared to LDLR$^{-/-}$ mice/HFD controls (n=5).

Example 3

Clearance of Senescent Cells Ameliorates Atherosclerosis in LDLR−/−/3MR Mice

The impact of clearance of senescent cells on the stability and size of mature atherosclerotic plaques was studied in LDLR−/−/3MR double transgenic mice. From 10 weeks of age, LDLR−/−/3MR double transgenic mice (10 weeks) and LDLR−/− single transgenic mice (control) were fed a high fat diet (Harlan Teklad TD.88137) having 42% calories from fat beginning at Week 0 until Week 12.5, when the mice were switched to normal chow diet. Both groups of mice were treated with ganciclovir from week 12.5 over the next 100 days, with each treatment cycle comprising 5 days of ganciclovir (25 mg/kg intraperitoneally daily) and 14 days off. At the end of the 100 day treatment period, the mice were sacrificed, plasma and tissues were collected, and atherosclerosis was quantitated.

Figure 30C:
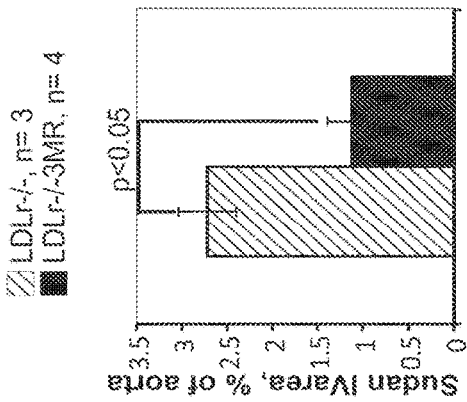
FIGS. 30A-C illustrate staining analysis for aortic plaques in LDLR−/−/3MR double transgenic mice and LDLR−/− control mice fed a HFD after a 100 day treatment period with ganciclovir.
Figure 30B:
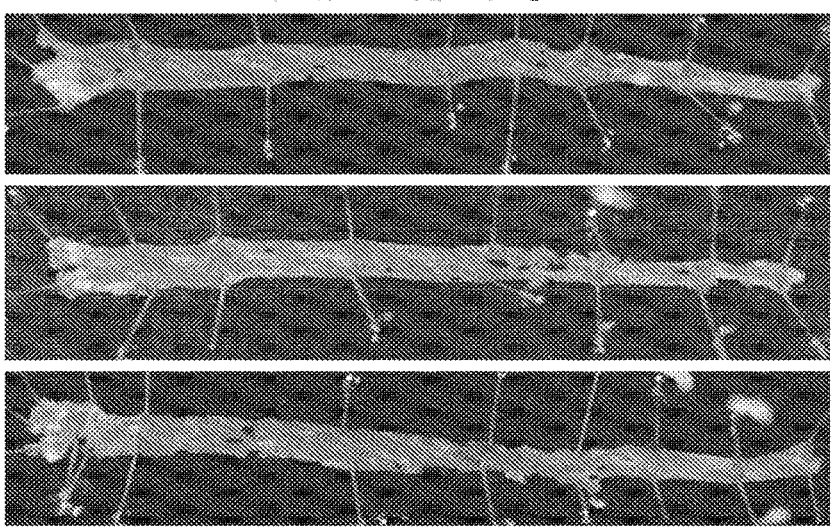
Figure 30A:
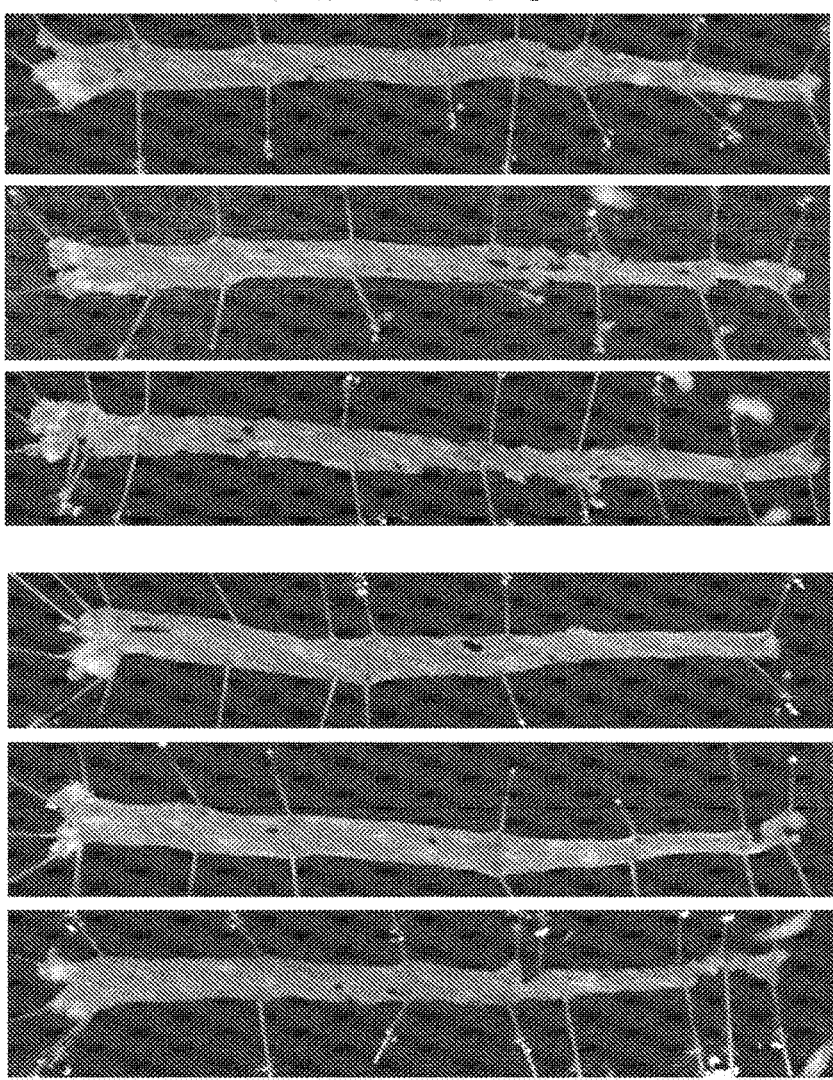

Descending aortas were dissected and stained with Sudan IV to visualize the plaque lipids. As shown in FIGS. 30A-B, ganciclovir-treated LDLR−/−/3MR double transgenic mice had fewer atherosclerotic plaques with less intense staining than the LDLR−/− control mice fed a HFD. The % of the aorta covered in plaques as measured by area of Sudan IV staining was also significantly lower in the ganciclovir-treated LDLR−/−/3MR mice as compared to the LDLR−/− control mice (see FIG. 30C).

Plaques from ganciclovir-treated LDLR−/− control and LDLR−/−/3MR mice (see dashed circled plaques in FIGS. 31A-B, respectively) were harvested and cut into cross-sections and stained with to characterize the general architecture of the atherosclerotic plaques. "#" indicates fat located on the outside of the aorta (see FIG. 31A). The plaques marked with an "*" and "**" in FIGS. 31A and B, respectively, are shown as stained cross-sections in FIGS. 31B and D, respectively. As illustrated in FIGS. 31B and D, clearance of senescent cells in ganciclovir-treated LDLR−/−/3MR mice has an effect on plaque morphology as compared to LDLR−/− control mice. The plaque from the control mice has identifiable "lipid pockets" accumulating within. The plaque from the ganciclovir treated LDLR−/−/ 3MR mice shows the presence of a thick fibrin cap and the absence of lipid pockets. Disruption or tear in the cap of a lipid-rich plaque is a trigger for coronary events through exposure of plaque thrombogenic components to platelets and clotting components of the blood. Plaques that grow more rapidly as a result of rapid lipid deposition and have thin fibrin caps are prone to rupture. Slowly growing plaques with mature fibrin caps tend to stabilize and are not prone to rupture. Taken together, these experiments indicate that removal of senescent cells may affect atherosclerotic plaque architecture and have a stabilizing effect.

Figure 32:
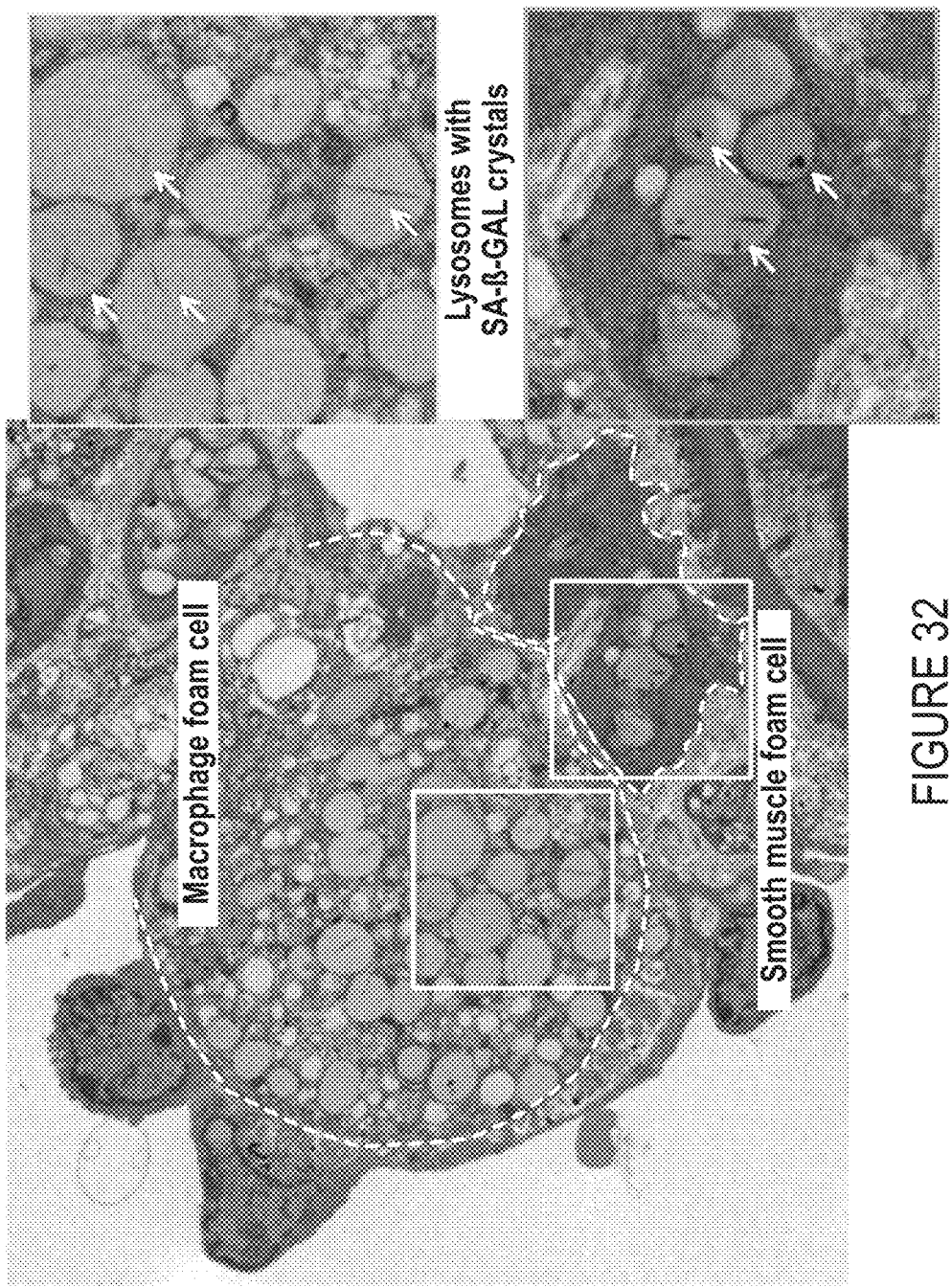
FIG. 32 shows that SA-β-GAL crystals localize to lipid-bearing foam cells from an atherosclerotic artery of a mouse fed a high-fat diet. The macrophage foam cell is shown by a white dotted outline and adjacent to the macrophage foam cell is a smooth muscle foam cell. The left boxed area in the macrophage foam cell is magnified and shown on the upper right to illustrate lysosomes with SA-β-GAL crystals. The boxed area within the smooth muscle foam cell is magnified and shown on the lower right side of the figure.
Figure 33:
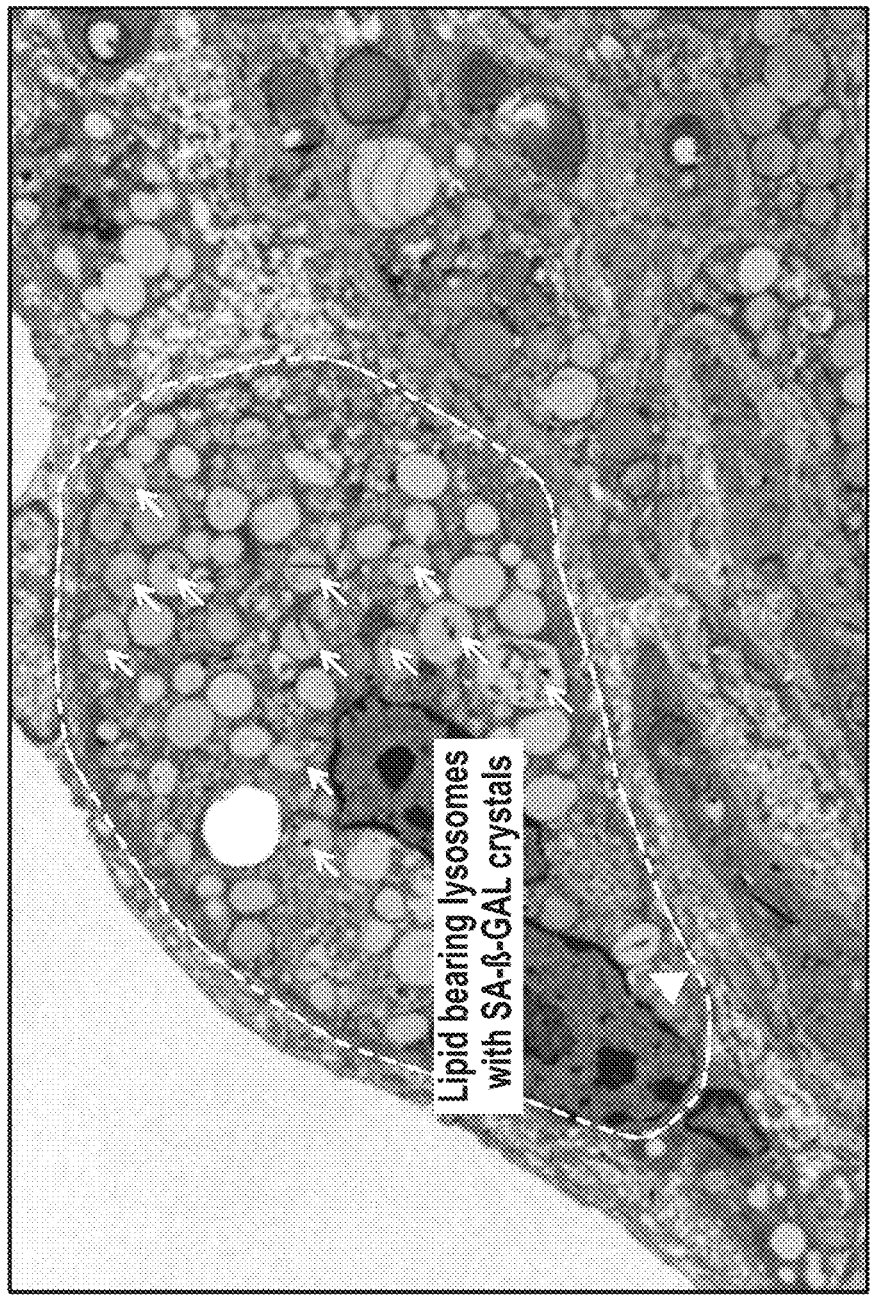
FIG. 33 presents a macrophage foam cell from an atherosclerotic artery of a mouse fed a high-fat diet. Lipid-bearing lysosomes containing SA-β-GAL crystals are noted by the arrows.
Figure 34:
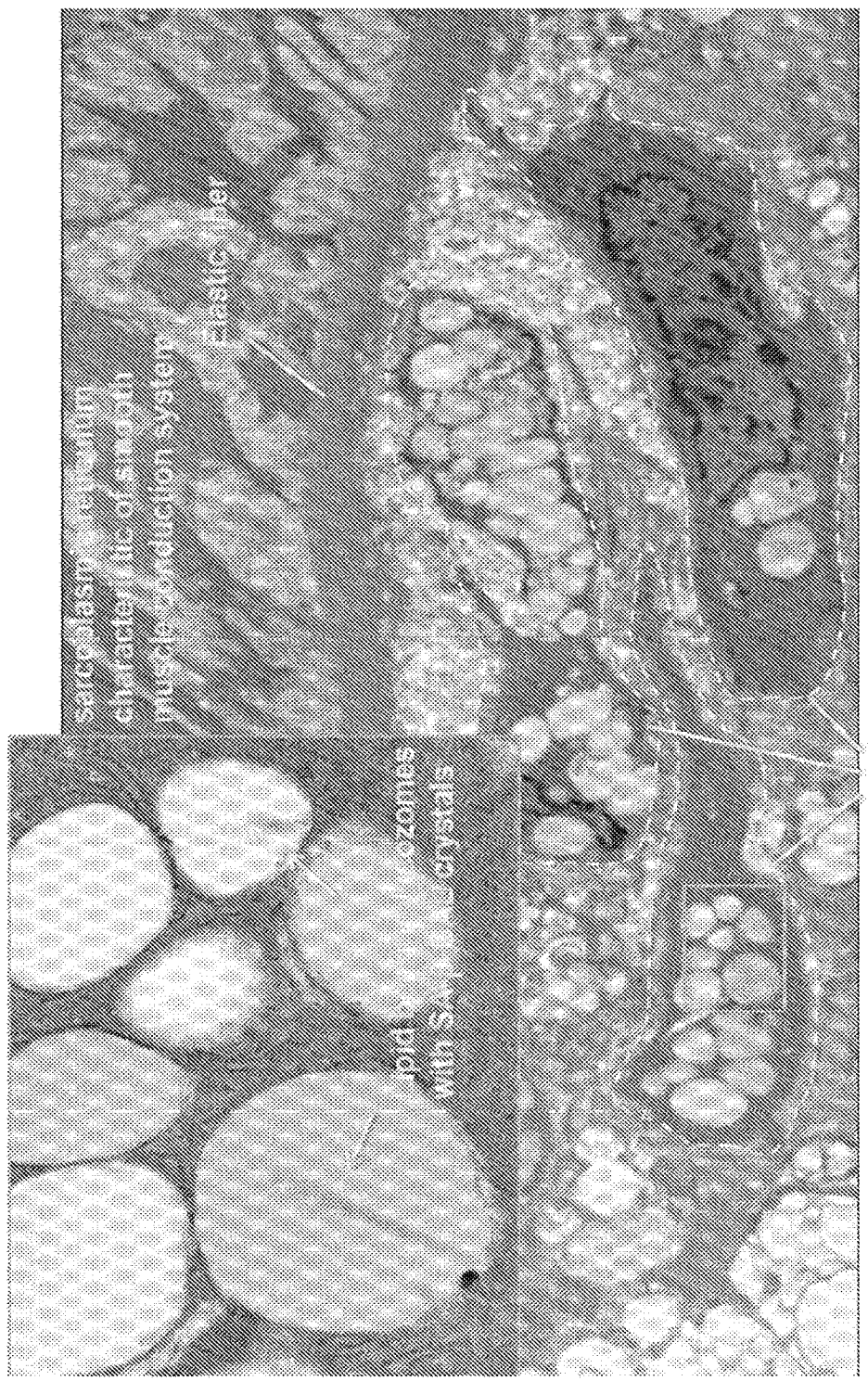
FIG. 34 shows that SA-β-GAL crystals localize in the lysozomes of smooth muscle foam cells in an atherosclerotic artery of a mouse fed a high-fat diet. The boxed area in the lower left portion of the illustration is magnified and shown in the insert at the top left.

Tissue sections of atherosclerotic aortas were prepared and stained to detect SA-β-GAL. X-GAL crystals were located in the lysosomes of lipid-bearing macrophage foam cells and smooth muscle foam cells (see FIGS. 32-34).

REFERENCES

1. Z. Cui, M. C. Willingham, The effect of aging on cellular immunity against cancer in SR/CR mice. *Cancer immunology, immunotherapy: CII* 53, 473-478 (2004).
2. I. Tabas, G. Garcia-Cardena, G. K. Owens, Recent insights into the cellular biology of atherosclerosis. *J Cell Biol* 209, 13-22 (2015).
3. C. Weber, H. Noels, Atherosclerosis: current pathogenesis and therapeutic options. *Nat Med* 17, 1410-1422 (2011).
4. C. E. Myers, N. N. Mirza, J. Lustgarten, Immunity, cancer and aging: lessons from mouse models. *Aging and disease* 2, 512-523 (2011).
5. K. Sakakura et al., Pathophysiology of atherosclerosis plaque progression. *Heart, lung & circulation* 22, 399-411 (2013).
6. I. Gorenne, M. Kavurma, S. Scott, M. Bennett, Vascular smooth muscle cell senescence in atherosclerosis. *Cardiovascular research* 72, 9-17 (2006).
7. T. Minamino et al., Endothelial cell senescence in human atherosclerosis: role of telomere in endothelial dysfunction. *Circulation* 105, 1541-1544 (2002).
8. J. C. Wang, M. Bennett, Aging and atherosclerosis: mechanisms, functional consequences, and potential therapeutics for cellular senescence. *Circ Res* 111, 245-259 (2012).
9. D. Munoz-Espin, M. Serrano, Cellular senescence: from physiology to pathology. *Nat Rev Mol Cell Biol* 15, 482-496 (2014).

10. J. Wang et al., Vascular Smooth Muscle Cell Senescence Promotes Atherosclerosis and Features of Plaque Vulnerability. *Circulation* 132, 1909-1919 (2015).
11. A. K Khanna, Enhanced susceptibility of cyclin kinase inhibitor p21 knockout mice to high fat diet induced atherosclerosis. *J Biomed Sci* 16, 66 (2009).
12. J. Mercer, N. Figg, V. Stoneman, D. Braganza, M. R. Bennett, Endogenous p53 protects vascular smooth muscle cells from apoptosis and reduces atherosclerosis in ApoE knockout mice. *Circ Res* 96, 667-674 (2005).
13. H. Gonzalez-Navarro et al., p19(ARF) deficiency reduces macrophage and vascular smooth muscle cell apoptosis and aggravates atherosclerosis. *J Am Coll Cardiol* 55, 2258-2268 (2010).
14. K. Wouters et al., Bone marrow p16$^{Ink4a}$-deficiency does not modulate obesity, glucose homeostasis or atherosclerosis development. *PLoS One* 7, e32440 (2012).
15. C. L. Kuo et al., Cdkn2a is an atherosclerosis modifier locus that regulates monocyte/macrophage proliferation. *Arterioscler Thromb Vasc Biol* 31, 2483-2492 (2011).
16. M. Demaria et al., An Essential Role for Senescent Cells in Optimal Wound Healing through Secretion of PDGF-AA. *Dev Cell* 31, 722-733 (2014).
17. H. Williams, J. L. Johnson, K. G. Carson, C. L. Jackson, Characteristics of intact and ruptured atherosclerotic plaques in brachiocephalic arteries of apolipoprotein E knockout mice. *Arterioscler Thromb Vasc Biol* 22, 788-792 (2002).
18. D. J. Baker et al., Clearance of p16$^{Ink4a}$-positive senescent cells delays ageing-associated disorders. *Nature* 479, 232-236 (2011).
19. D. J. Baker et al., Naturally occurring p16(Ink4a)-positive cells shorten healthy lifespan. *Nature* 530, 184-189 (2016).
20. J. Chang et al., Clearance of senescent cells by ABT263 rejuvenates aged hematopoietic stem cells in mice. *Nat Med* 22, 78-83 (2016).
21. Y. Nakashima, E. W. Raines, A. S. Plump, J. L. Breslow, R. Ross, Upregulation of VCAM-1 and ICAM-1 at atherosclerosis-prone sites on the endothelium in the ApoE-deficient mouse. *Arterioscler Thromb Vasc Biol* 18, 842-851 (1998).
22. J. L. Johnson, C. L. Jackson, Atherosclerotic plaque rupture in the apolipoprotein E knockout mouse. *Atherosclerosis* 154, 399-406 (2001).
23. M. C. Clarke et al., Apoptosis of vascular smooth muscle cells induces features of plaque vulnerability in atherosclerosis. *Nat Med* 12, 1075-1080 (2006).
24. N. Maldonado et al., A mechanistic analysis of the role of microcalcifications in atherosclerotic plaque stability: potential implications for plaque rupture. *American journal of physiology. Heart and circulatory physiology* 303, H619-628 (2012).
25. C. Silvestre-Roig et al., Atherosclerotic plaque destabilization: mechanisms, models, and therapeutic strategies. *Circ Res* 114, 214-226 (2014).
26. S. M. Ghaderian, R. Akbarzadeh Najar, A. S. Tabatabaei Panah, Genetic polymorphisms and plasma levels of matrix metalloproteinases and their relationships with developing acute myocardial infarction. *Coronary artery disease* 21, 330-335 (2010).
27. A. V. Finn, M. Nakano, J. Narula, F. D. Kolodgie, R. Virmani, Concept of vulnerable/unstable plaque. *Arterioscler Thromb Vasc Biol* 30, 1282-1292 (2010).
28. K. Inoue et al., Serial coronary CT angiography-verified changes in plaque characteristics as an end point: evaluation of effect of statin intervention. *JACC. Cardiovascular imaging* 3, 691-698 (2010).
29. D. J. Baker et al., Naturally occurring p16-positive cells shorten healthy lifespan. *Nature*, (2016).
30. S. Curado, D. Y. Stainier, R. M. Anderson, Nitroreductase-mediated cell/tissue ablation in zebrafish: a spatially and temporally controlled ablation method with applications in developmental and regeneration studies. *Nature protocols* 3, 948-954 (2008).
31. D. J. Baker et al., BubR1 insufficiency causes early onset of aging-associated phenotypes and infertility in mice. *Nat Genet* 36, 744-749 (2004).
32. C. A. Conover et al., Transgenic overexpression of pregnancy-associated plasma protein-A in murine arterial smooth muscle accelerates atherosclerotic lesion development. *American journal of physiology. Heart and circulatory physiology* 299, H284-291 (2010).

The invention claimed is:
1. A method of inhibiting progression of atherosclerosis in a subject, comprising treating the subject with a course of therapy using a pharmaceutical composition that contains a senolytic compound in an amount and in a formulation that is effective in eliminating p 16 positive senescent cells from a plurality of atherosclerotic plaques in the subject,
   wherein the senolytic compound constitutes a means for selectively inhibiting mouse double minute 2 homolog (MDM2),
   wherein the course of therapy includes:
   (1) a treatment period during which the composition is administered systemically to the subject such that the compound contacts and selectively removes senescent cells from the atherosclerotic plaques; followed by
   (2) a therapeutic period of at least two weeks, during which the composition is not administered to the subject, and progression of the atherosclerosis is inhibited as a result of administration of the composition to the subject during the treatment period.
2. The method of claim 1, wherein the compound is (4-[(4S,5R)-4,5 bis(4-chlorophenyl)-4,5-dihydro-2-[4-methoxy-2-(1-methylethoxy)phenyl]-1H-imidazol-1-yl]carbonyl]-2-piperazinone)(Nutlin-3A), or a pharmaceutically acceptable salt thereof.
3. The method of claim 1, wherein the compound is selected from Nutlin-1, Nutlin-2, RG-7112, RG7388, DS-3032b, MI-63, MI-126, MI-122, MI-142, MI-147, MI-219, MI-220, MI-221, MI-773, 3-(4-chlorophenyl)-3-((1-(hydroxymethyl)cyclopropyl)methoxy)-2-(4-nitrobenzyl)isoindolin-1-one, Serdemetan, AM-8553, CGM097, RO-2443, RO-5963, 5-[(3S)-3-(4-chlorophenyl)-4-[(R)-1-(4-chlorophenyl)ethyl]-2,5-dioxo-7-phenyl-1,4-diazepin-1-yl]valeric acid, 5-[(3S)-7-(2-bromophenyl)-3-(4-chlorophenyl)-4-[(R)-1-(4-chlorophenypethyl]-2,5-dioxo-1,4-diazepin-1-yl]valeric acid, TDP521252, TDP665759, NSC279287, and phannaceutically acceptable salts thereof.
4. The method of claim 1, wherein the senescent cells are senescent foam cell macrophages.
5. The method of claim 1, wherein the amount of the compound, the formulation of the composition, and the length of the treatment period are effective in delaying coat thinning of the atherosclerotic plaques during the therapeutic period.
6. The method of claim 1, wherein the amount of the compound, the formulation of the composition, and the length of the treatment period are effective in stabilizing the atherosclerotic plaques, thereby reducing the risk that the plaques will rupture during the therapeutic period.

7. A method of removing senescent foam cell macrophages from the vasculature of a subject in need thereof, the method comprising:
treating the subject with a course of therapy using a pharmaceutical composition that contains a senolytic compound in an amount and in a formulation that is effective in eliminating senescent foam macrophages from the vasculature of the subject,
wherein the senolytic compound constitutes a means for selectively inhibiting mouse double minute 2 homolog (MDM2),
wherein the course of therapy includes:
(1) a treatment period during which the composition is administered systemically to the subject such that the compound selectively removes senescent foam macrophages from the vasculature of the subject; followed by
(2) a therapeutic period of at least two weeks, during which the composition is not administered to the subject, and occlusion of the vasculature by plaque distribution or rupture is inhibited as a result of administration of the composition to the subject during the treatment period.

8. The method of claim 7, wherein the compound is (4-[(4S,5R)-4,5bis(4-chlorophenyl)-4,5-dihydro-2-[4-methoxy-2-(1-methylethoxy)phenyl]-1H-imidazol-1-yl]carbonyl]-2-piperazinone)(Nutlin-3A), or a pharmaceutically acceptable salt thereof.

9. The method of claim 7, wherein the compound is selected from Nutlin-1, Nutlin-2, RG-7112, RG7388, DS-3032b, MI-63, MI-126, MI-122, MI-142, MI-147, MI-219, MI-220, MI-221, MI-773, 3-(4-chlorophenyl)-3-((1-(hydroxymethyl)cyclopropyl)methoxy)-2-(4-nitrobenzyl)isoindolin-1-one, Serdemetan, AM-8553, CGM097, RO-2443, RO-5963, 5-[(3S)-3-(4-chlorophenyl)-4-[(R)-1-(4-chlorophenyl)ethyl]-2,5-dioxo-7-phenyl-1,4-diazepin-1-yl]valeric acid, 5-[(3S)-7-(2-bromophenyl)-3-(4-chlorophenyl)-4-[(R)-1-(4-chlorophenyl)ethyl]-2,5-dioxo-1,4-diazepin-1-yl]valeric acid, TDP521252, TDP665759, NSC279287, and pharmaceutically acceptable salts thereof.

10. The method of claim 7, wherein the senescent foam cell macrophages are positive for p 16.

11. The method of claim 7, wherein the amount of the compound, the formulation of the composition, and the length of the treatment period are effective in inhibiting formation of new atherosclerotic plaques in the subject during the therapeutic period.

12. The method of claim 7, wherein the amount of the compound, the formulation of the composition, and the length of the treatment period are effective in stabilizing atherosclerotic plaques in the subject, thereby reducing the risk that the plaques will rupture during the therapeutic period.

* * * * *